United States Patent
Zhong

(10) Patent No.: US 11,919,899 B2
(45) Date of Patent: Mar. 5, 2024

(54) SUBSTITUTED 1-(3,3-DIFLUOROPIPERIDIN-4-YL)-IMIDAZO[4,5-C] QUINOLIN-2-ONE COMPOUNDS WITH BLOOD-BRAIN BARRIER PENETRABLE CAPABILITY

(71) Applicant: Wei Zhong, Corona, CA (US)

(72) Inventor: Wei Zhong, Corona, CA (US)

( * ) Notice: Subject to any disclaimer, the term of this patent is extended or adjusted under 35 U.S.C. 154(b) by 0 days.

(21) Appl. No.: 18/002,717

(22) PCT Filed: Sep. 21, 2020

(86) PCT No.: PCT/US2020/051833
§ 371 (c)(1),
(2) Date: Dec. 21, 2022

(87) PCT Pub. No.: WO2022/060377
PCT Pub. Date: Mar. 24, 2022

(65) Prior Publication Data
US 2023/0242525 A1  Aug. 3, 2023

(51) Int. Cl.
C07D 471/04 (2006.01)
A61P 35/00 (2006.01)
C07D 519/00 (2006.01)

(52) U.S. Cl.
CPC ............ C07D 471/04 (2013.01); A61P 35/00 (2018.01); C07D 519/00 (2013.01); *C07B 2200/05* (2013.01)

(58) Field of Classification Search
CPC .. C07D 471/04; C07D 519/00; C07D 487/04; A61P 35/00; A61P 35/04; C07B 2200/05; A61K 45/06; A61K 31/4545
See application file for complete search history.

(56) References Cited

U.S. PATENT DOCUMENTS

| | | | |
|---|---|---|---|
| 2011/0251202 A1 | 10/2011 | Garcia-Echeverria et al. | |
| 2013/0237562 A1 | 9/2013 | Barda et al. | |
| 2014/0005163 A1 | 1/2014 | Furet et al. | |
| 2018/0318287 A1 | 11/2018 | Pike et al. | |
| 2019/0211013 A1 | 7/2019 | Fuchss et al. | |

FOREIGN PATENT DOCUMENTS

| | | |
|---|---|---|
| CN | 102372711 B | 9/2014 |
| EP | 3072893 A1 | 9/2016 |
| WO | 2017153578 A1 | 9/2017 |
| WO | 20170153578 A1 | 9/2017 |
| WO | WO-2018167203 A1 * | 9/2018 ........... A61K 31/437 |

OTHER PUBLICATIONS

PCT/US2020/051833—International Preliminary Report on Patentability, dated Mar. 30, 2023, 8 pages.
PCT/US2020/051833—International Search Report and Written Opinion, dated Feb. 2, 2021, 27 pages.
Pubchem. CID 134163712. Retrieved from the Internet <URL: https://pul,d1 m.ncbi.nlm.nlh.gov/compound/134163/12>; p. 2, Jun. 22, 2018, pp. 1-11.
EP20954302.4—Extended European Search Report dated May 23, 2023, 47 pages.

* cited by examiner

*Primary Examiner* — John M Mauro
(74) *Attorney, Agent, or Firm* — Getech Law LLC; Jun Ye

(57) ABSTRACT

The present invention discloses substituted 1-(3,3-difluoropiperidin-4-yl)-8-(pyridin-3-yl)-1,3-dihydro-2H-imidazo [4,5-c]quinolin-2-one compounds having a capacity to cross the blood-brain barrier; the compound has the structural formula represented by formula (I):

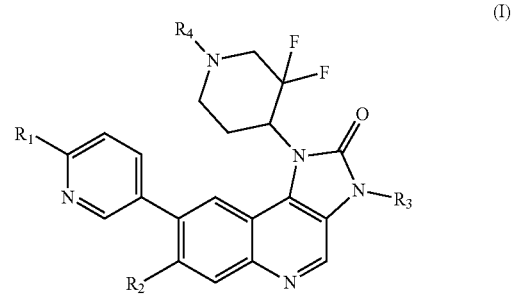

(I)

The substituted 1-(3,3-difluoropiperidin-4-yl)-8-(pyridin-3-yl)-1,3-dihydro-2H-imidazo[4,5-c]quinolin-2-one compounds, derivatives and pharmaceutically acceptable salts thereof of the present invention have the ability to cross the blood-brain barrier and are capable of acting as a drug characteristic of a protein kinase inhibitor, in particular for the expression of a protein through an Ataxia-telangiectasia mutated kinase (ATM) and can be used to treat or prevent disorders associated with abnormal protein kinase activity, such as cancer, cancer with brain metastases, cancer with meningeal metastases, glioma, glioblastoma, DIPG, and the like either as monotherapy or combination with other treatment.

10 Claims, 12 Drawing Sheets

SUBSTITUTED 1-(3,3-DIFLUOROPIPERIDIN-4-YL)-IMIDAZO[4,5-C] QUINOLIN-2-ONE COMPOUNDS WITH BLOOD-BRAIN BARRIER PENETRABLE CAPABILITY

CROSS-REFERENCE TO RELATED APPLICATION

This application is a 371 of international Patent Application No. PCT/US2020/051833, filed Sep. 21, 2020, the content of which application is hereby expressly incorporated herein by reference in its entirety.

TECHNICAL FIELD

The present invention relates to novel 1-(3,3-difluoropiperidin-4-yl)-imidazo[4,5-c]quinolin-2-one derivatives, salts, hydrates thereof and polymorphs thereof, and in particular to a substituted 1-(3,3-difluoropiperidin-4-yl)-imidazo[4,5-c] quinolin-2-one compound having a capacity to penetrate the blood-brain barrier and selectively modulate ataxia telangiectasia mutated (ATM) kinase, and the specification therefore also relates to the use of such compounds and salts thereof to treat or prevent ATM kinase mediated disease, including cancer, especially when combination with radiotherapy or DNA double strand breaks agent for glioma, glioblastoma, diffuse intrinsic pontine glioma and cancers with central nervous system metastasis.

BACKGROUND TECHNIQUE

ATM (Ataxia-telangiectasia mutated) kinase, a member of the phosphatidylinositol 3-kinaserelated kinase (PIKK) family of serine/threonine protein kinases located on human chromosome 11 (11q22.3) and made up of 69 exons spread across 150 kb of genomic DNA, comprises DNA-dependent protein kinase catalytic subunit (DNA-PKcs/PRKDC), mammalian target of rapamycin (MTOR/FRAP) and suppressor of morphogenesis in genitalia (SMG1). The cellular functions of ATM kinase range from regulation of the DNA damage response (DDR) to cell survival, proliferation, metabolism, differentiation, motility and nonsense-mediated mRNA decay (S. P. Jackson, J. Bartek, Nature, 461 (2010), pp. 1071-1078, A. Ciccia, S. J. Elledge Mol Cell, 40 (2011), pp. 179-204).

ATM kinase plays a crucial role in the activation of the G1/S cell cycle checkpoint, which prevents cells with damaged DNA from entering S-phase. ATM-defective cells are sensitive to DNA double strand break-inducing agents, such as ionizing radiation and topoisomerase-II inhibitors (doxorubicin, etoposide, etoposide, teniposide, doxorubicin, idarubicin, epirubicin, and mitoxantrone) and single strand break to double strand break conversion during replication agents such as topoisomerase-I inhibitors (irinotecan and topotecan etc.) making ATM an attractive target for anticancer chemo- and radio-sensitization, and as a result ATM kinase inhibitors are expected to be of use in the treatment of cancer as rational combination partners for existing therapies.

In its inactive state, ATM forms homodimers or higher order multimers which dissociate into active monomers following rapid intermolecular autophosphorylation of serine 1981, a direct pharmacodynamic and patient selection biomarker for tumor pathway dependency upon ATM activation. The recruitment of ATM to sites of DNA DSBs is mediated via the MRE11-RAD50-NBS1 (MRN) complex. The MRN complex quickly assembles at sites of DNA DSBs, where it acts as a damage sensor that can also form a physical bridge spanning the DSB (T. H. Stracker, J. H. J. Petrini, Nat Rev Mol Cell Biol, 12 (2011), pp. 90-103).

ATM recruitment has been shown to require its binding to the C-terminus of NBS1, an interaction that also enhances the kinase activity of ATM (Z. You, C. Chahwan, J. Bailis, T. Hunter, P. Russell, Mol Cell Biol, 25 (2005), pp. 5363-5379). Immediately following its recruitment to sites of DNA DSBs, ATM contributes to the phosphorylation of the histone variant H2AX on Serine 139 (S. Burma, B. P. Chen, M. Murphy, A. Kurimasa, D. J. Chen, Biol Chem, 276 (2001), pp. 42462-42467), which initiates a cascade that assembles DDR components at the breakage site (T. T. Paull, E. P. Rogakou, V. Yamazaki, C. U. Kirchgessner, M. Gellert, W. M. Bonner, Curr Biol, 10 (2000), pp. 886-895).

The downstream targets of ATM include tumor suppressor protein p53 and checkpoint kinase 2 (CHK2) at G1/S cell cycle. ATM also contributes to the activation of an intra-S-phase checkpoint, as cells deficient in ATM do not reduce DNA synthesis following induction of DNA DSBs, a phenotype referred to as radioresistant DNA synthesis. The S-phase checkpoint functions of ATM in response to IR are partly mediated through phosphorylation of NBS1 and SMC1. Additional enforcement of the intra-S-phase checkpoint by ATM is mediated through its activation of CHK2, which induces ubiquitinoylation and degradation of the S-phase-promoting phosphatase Cdc25A that promotes S-phase progression through activation of the cyclin-dependent kinase 2 (Cdk2), which is needed for DNA synthesis. In response to IR, hundreds of substrates are phosphorylated in an ATM-dependent manner while ATM functions in the regulation of signaling pathways involved in maintaining cellular homeostasis, including cellular metabolism, responses to hypoxia and oxidative stress via DDR-independent roles.

Glioblastoma, or glioblastoma multiforme, (GBM) are the advanced malignant WHO Grade IV brain tumors. Due to the presence of the blood-brain barrier (BBB), no target therapies that can achieve effective amount in the brain, have been approved for the treatment of GBM or DIPG patients. Radiation therapy and surgery along with Temozolomide are still the main means of treatment, but the treatment effect is limited. Especially for DIPG patients, radiation is the only treatment option with recurrence within 5.5 months. See, for example, Hamer et al., Neuro-Oncology 12(3):304-316, 2010. GBM is a whole-brain disease and all GBM have clinically significant regions of tumor with an intact BBB. Failure to deliver an effective therapy to all regions of GBM will result in treatment failure and recurrence is inevitable (Sarkaria et al. Neuro-Oncology 20(2): 184-191, 2018). The role of ATM in radiation sensitivity and the potential use of brain penetrable ATM inhibitors as radiosensitizers might be very useful for the treatment of brain cancers or cancers with central nervous system metastasis, especially for the indications that radiation is the only treatment option such as DIPG.

The Contents of the Invention

In view of the importance of the above-mentioned brain cancers, especially glioblastoma, DIPG and cancers with central nervous system metastases resistance by radiation, ATM inhibitors that can penetrate the blood-brain barrier and reach an effective amount in intracranial for the treatment or prevention of cancer is particularly useful. It is an object of the present invention to provide substituted 1-(3, 3-difluoropiperidin-4-yl)-imidazo[4,5-c] quinolin-2-one compounds having a desired ability to penetrate the blood-brain barrier and having a drug characteristic of an ATM protein kinase inhibitor and its use.

The present invention exhibits a number of compounds having favorable physical and chemical properties (e.g. high permeability, and low efflux rates), and/or advantageous toxicity characteristics (e.g., reduction of hERG and low drug-drug interaction liability) and/or other more favorable metabolic curves (non-aldehyde oxidase substrate). Thus, such compounds have an effective amount in intracranial through penetrating the blood-brain barrier for the treatment and/or prevention of central nervous system metastases and brain cancers when combination with radiation therapy or other DNA double strand breaks agents.

The object of the present invention is achieved by the following technical scheme:

The present invention relates to a compound comprising a structure of formula (I), (II) and (III), said compound being:

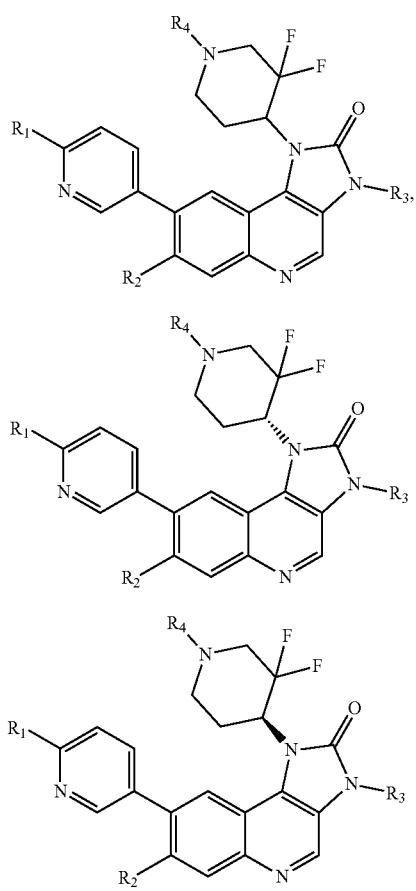

Wherein R1 is independently selected from OC1-3 alkyl, OC3-5 cycloalkyl, OC1-C3 deuterated alkyl, dialkyl amine, substituted C4-C6 cycloamine or diazabicyclo amine;

R2 is independently selected from hydrogen or fluoro;

R3 is independently selected from methyl or deuterated methyl;

R4 is independently selected from C1-C3 alkyl or C1-C3 deuterated alkyl.

Preferably, in the formula (I), (II) and (III)

R1 is independently selected from methoxy, ethoxy, iso-propoxy, cyclopropoxy, deuterated methoxy, dimethyl amine, N,N-dimethylazetidine-3-amine or 2-methyl-2,6-diazabicyclo[3.2.0]heptane;

R2 is independently selected from hydrogen or fluoro;

R3 is independently selected from methyl or deuterated methyl;

R4 is independently selected from methyl, ethyl, isopropyl or deuterated methyl.

The present invention also relates to a pharmaceutical composition comprising a compound of the foregoing, a salt thereof, a solvate thereof, a hydrate thereof or a polymorph thereof, and a pharmaceutically acceptable accepted excipients or adjunct ingredients.

The present invention also relates to an ATM inhibitor, said inhibitor being an active ingredient with the aforementioned compound; said inhibitor being capable of penetrating blood-brain barrier.

The present invention also relates to the use of a compound of the foregoing, or the aforementioned pharmaceutical composition, or the aforementioned inhibitor in the manufacture of a medicament for the treatment or prevention of diseases mediated by ATM kinase.

Preferably, the protein is a kinase with the activated ATM.

Preferably, the disease is a central nervous metastatic disease of cancer, a proliferative disease, a brain cancer, a central nervous system disease, or a cancer.

Preferred central nervous metastases of the cancer include brain metastases of cancer, meningeal metastasis of cancer, glioma, DIPG and glioblastoma.

The preferred diseases are brain cancer, lung cancer, colon cancer, breast cancer, prostate cancer, liver cancer, membranous adenocarcinoma, kidney cancer, lymphoma, ovarian cancer, gastric cancer, skin cancer, bone cancer, glioma, neuroblastoma, hepatocellular carcinoma, papillary renal cell carcinoma or squamous cell carcinoma of the head and neck.

Preferably, the disease is non-small cell lung cancer (NSCLC).

Preferably, the disease is non-small cell lung cancer (NSCLC) with brain metastases.

Preferably, the disease is non-small cell lung cancer (NSCLC) with leptomeningeal metastases.

Preferably, the disease is glioma.

Preferably, the disease is glioblastoma.

Preferably, the disease is DIPG.

In another aspect, the present invention relates to a method of treating a disease or disease symptom in a subject in need thereof comprising administering to the subject an effective amount of any compound of the general formula herein, or a pharmaceutically acceptable salt, solvate or hydrate thereof (or a combination thereof). The disease or disease symptoms may be any of those diseases regulated by ATM protein kinases for the DNA damage response pathway, especially the reparation of DNA double strand breaks caused by radiation or other agents. These disease or disease symptoms may be, for example, cancer or proliferative diseases or disorders (e.g., including those described herein).

Compared with the prior art, the invention has the following beneficial effects:

1) The 1-(3,3-difluoropiperidin-4-yl)-imidazo[4,5-c] quinolin-2-one derivatives of the present invention and their pharmaceutically acceptable salts have the ability to penetrate the blood-brain barrier and are capable of acting as a drug characteristic of a protein kinase inhibitor, in particular for a protein that expresses through an ATM and can be used to treat or prevent disorders associated with abnormal protein kinase activity such as cancer, cancer with brain metastases, cancer with meningeal metastases, glioma, glioblastoma and DIPG.

2) The 1-(3,3-difluoropiperidin-4-yl)-imidazo[4,5-c] quinolin-2-one derivatives of the present invention and their pharmaceutically acceptable salts have a low effluent rate, which is not a human P-glycoprotein and breast cancer resistance protein efflux substrate, which reduces resistance to efflux enzymes.

3) The 1-(3,3-difluoropiperidin-4-yl)-imidazo[4,5-c] quinolin-2-one derivative and the pharmaceutically acceptable salt thereof have good pharmacokinetic (Non aldehyde oxidase substrate) and high biological activity and selectivity over other PIKKs such as ATR, DNA-PK, which can minimize potential toxicity, reduce the burden of the tablets and improve the tablet's ingestion compliance.

4) The 1-(3,3-difluoropiperidin-4-yl)-imidazo[4,5-c] quinolin-2-one derivative and the pharmaceutically acceptable salt thereof have low risks for inhibition of ion channel such as hERG with good safety profile and good combinability properties with other agent with low risks for potential drug-drug interaction liability and time-dependent inhibition liability.

DETAILED DESCRIPTION

Figure 1A:
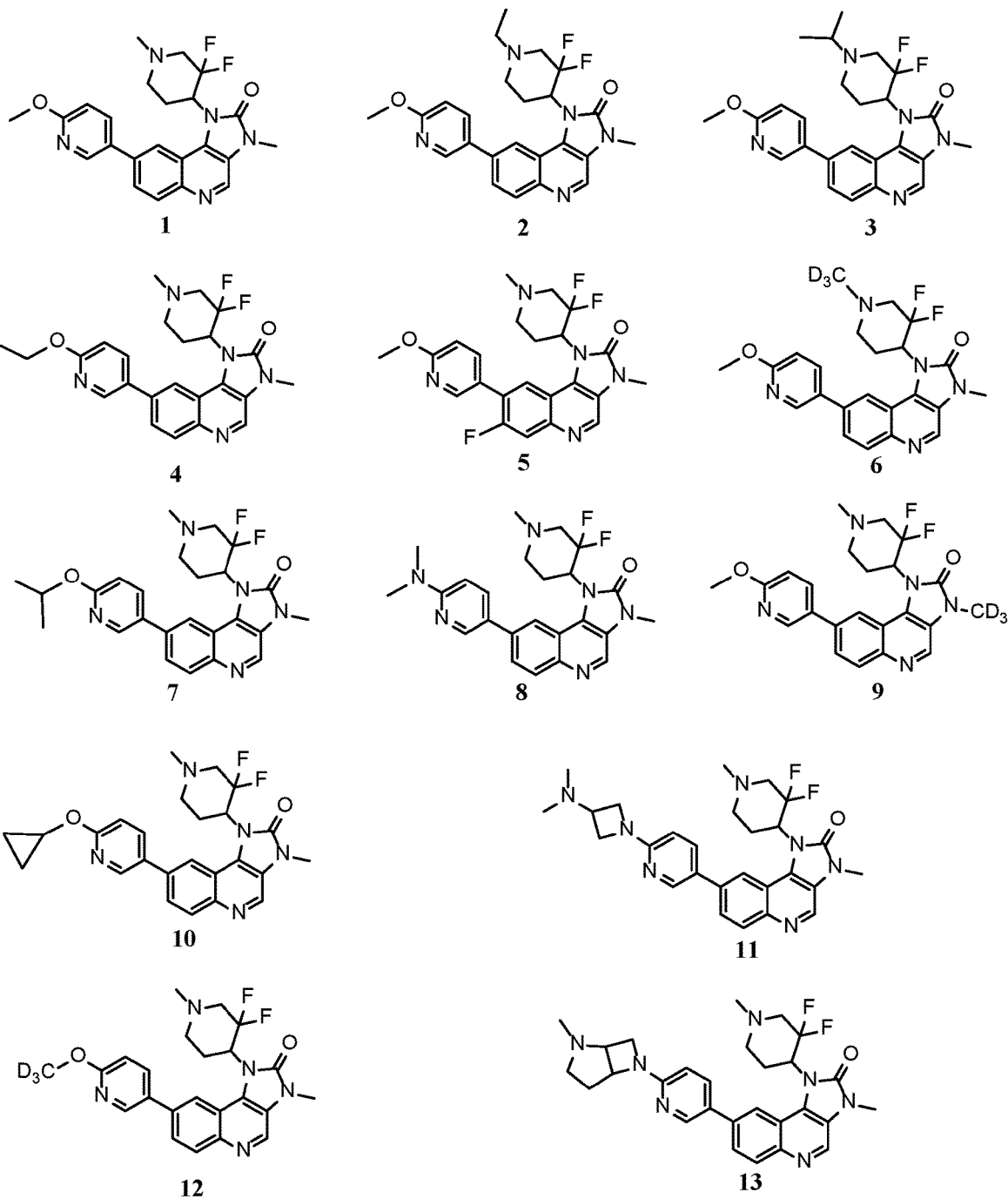
FIG. 1A-C shows the chemical structures of (R/S)-1-(3,3-difluoro-1-methylpiperidin-4-yl)-8-(6-methoxypyridin-3-yl)-3-methyl-1,3-dihydro-2H-imidazo[4,5-c]quinolin-2-one (1); (R/S)-1-(1-ethyl-3,3-difluoropiperidin-4-yl)-8-(6-methoxypyridin-3-yl)-3-methyl-1,3-dihydro-2H-imidazo[4,5-c]quinolin-2-one (2); (R/S)-1-(3,3-difluoro-1-isopropylpiperidin-4-yl)-8-(6-methoxypyridin-3-yl)-3-methyl-1,3-dihydro-2H-imidazo[4,5-c]quinolin-2-one (3); (R/S)-1-(3,3-difluoro-1-methylpiperidin-4-yl)-8-(6-ethoxypyridin-3-yl)-3-methyl-1,3-dihydro-2H-imidazo[4,5-c]quinolin-2-one (4); (R/S)-1-(3,3-difluoro-1-methylpiperidin-4-yl)-7-fluoro-8-(6-methoxypyridin-3-yl)-3-methyl-1,3-dihydro-2H-imidazo[4,5-c]quinolin-2-one (5); (R/S)-1-(3,3-difluoro-1-(methyl-d3)piperidin-4-yl)-8-(6-methoxypyridin-3-yl)-3-methyl-1,3-dihydro-2H-imidazo[4,5-c]quinolin-2-one (6); (R/S)-1-(3,3-difluoro-1-methylpiperidin-4-yl)-8-(6-isopropoxypyridin-3-yl)-3-methyl-1,3-dihydro-2H-imidazo[4,5-c]quinolin-2-one (7); (R/S)-1-(3,3-difluoro-1-methylpiperidin-4-yl)-8-(6-(dimethylamino)pyridin-3-yl)-3-methyl-1,3-dihydro-2H-imidazo[4,5-c]quinolin-2-one (8); (R/S)-1-(3,3-difluoro-1-methylpiperidin-4-yl)-8-(6-methoxypyridin-3-yl)-3-(methyl-d3)-1,3-dihydro-2H-imidazo[4,5-c]quinolin-2-one (9); (R/S)-8-(6-cyclopropoxypyridin-3-yl)-1-(3,3-difluoro-1-methylpiperidin-4-yl)-3-methyl-1,3-dihydro-2H-imidazo[4,5-c]quinolin-2-one (10); (R/S)-1-(3,3-difluoro-1-methylpiperidin-4-yl)-8-(6-(3-(dimethylamino)azetidin-1-yl)pyridin-3-yl)-3-methyl-1,3-dihydro-2H-imidazo[4,5-c]quinolin-2-one (11); (R/S)-1-(3,3-difluoro-1-methylpiperidin-4-yl)-8-(6-(methoxy-d3)pyridin-3-yl)-3-methyl-1,3-dihydro-2H-imidazo[4,5-c]quinolin-2-one (12); (R/S)-1-(3,3-difluoro-1-methylpiperidin-4-yl)-3-methyl-8-(6-((1R,5R/1S,5S)-(2-methyl-2,6-diazabicyclo[3.2.0]heptan-6-yl)pyridin-3-yl)-1,3-dihydro-2H-imidazo[4,5-c]quinolin-2-one (13); (R)-1-(3,3-difluoro-1-methylpiperidin-4-yl)-8-(6-methoxypyridin-3-yl)-3-methyl-1,3-dihydro-2H-imidazo[4,5-c]quinolin-2-one (14); (R)-1-(1-ethyl-3,3-difluoropiperidin-4-yl)-8-(6-methoxypyridin-3-yl)-3-methyl-1,3-dihydro-2H-imidazo[4,5-c]quinolin-2-one (15); (R)-1-(3,3-difluoro-1-isopropylpiperidin-4-yl)-8-(6-methoxypyridin-3-yl)-3-methyl-1,3-dihydro-2H-imidazo[4,5-c]quinolin-2-one (16); (R)-1-(3,3-difluoro-1-methylpiperidin-4-yl)-8-(6-ethoxypyridin-3-yl)-3-methyl-1,3-dihydro-2H-imidazo[4,5-c]quinolin-2-one (17); (R)-1-(3,3-difluoro-1-methylpiperidin-4-yl)-7-fluoro-8-(6-methoxypyridin-3-yl)-3-methyl-1,3-dihydro-2H-imidazo[4,5-c]quinolin-2-one (18); (R)-1-(3,3-difluoro-1-(methyl-d3)piperidin-4-yl)-8-(6-methoxypyridin-3-yl)-3-methyl-1,3-dihydro-2H-imidazo[4,5-c]quinolin-2-one (19); (R)-1-(3,3-difluoro-1-methylpiperidin-4-yl)-8-(6-isopropoxypyridin-3-yl)-3-methyl-1,3-dihydro-2H-imidazo[4,5-c]quinolin-2-one (20); (R)-1-(3,3-difluoro-1-methylpiperidin-4-yl)-8-(6-(dimethylamino)pyridin-3-yl)-3-methyl-1,3-dihydro-2H-imidazo[4,5-c]quinolin-2-one (21); (R)-1-(3,3-difluoro-1-methylpiperidin-4-yl)-8-(6-methoxypyridin-3-yl)-3-(methyl-d3)-1,3-dihydro-2H-imidazo[4,5-c]quinolin-2-one (22); (R)-8-(6-cyclopropoxypyridin-3-yl)-1-(3,3-difluoro-1-methylpiperidin-4-yl)-3-methyl-1,3-dihydro-2H-imidazo[4,5-c]quinolin-2-one (23); (R)-1-(3,3-difluoro-1-methylpiperidin-4-yl)-8-(6-(3-(dimethylamino)azetidin-1-yl)pyridin-3-yl)-3-methyl-1,3-dihydro-2H-imidazo[4,5-c]quinolin-2-one (24); (R)-1-(3,3-difluoro-1-methylpiperidin-4-yl)-8-(6-(methoxy-d3)pyridin-3-yl)-3-methyl-1,3-dihydro-2H-imidazo[4,5-c]quinolin-2-one (25); (R)-1-(3,3-difluoro-1-methylpiperidin-4-yl)-3-methyl-8-(6-((1R,5R)-(2-methyl-2,6-diazabicyclo[3.2.0]heptan-6-yl)pyridin-3-yl)-1,3-dihydro-2H-imidazo[4,5-c]quinolin-2-one (26); (R)-1-(3,3-difluoro-1-methylpiperidin-4-yl)-3-methyl-8-(6-((1S,5S)-(2-methyl-2,6-diazabicyclo[3.2.0]heptan-6-yl)pyridin-3-yl)-1,3-dihydro-2H-imidazo[4,5-c]quinolin-2-one (27); (S)-1-(3,3-difluoro-1-methylpiperidin-4-yl)-8-(6-methoxypyridin-3-yl)-3-methyl-1,3-dihydro-2H-imidazo[4,5-c]quinolin-2-one (28); (S)-1-(1-ethyl-3,3-difluoropiperidin-4-yl)-8-(6-methoxypyridin-3-yl)-3-methyl-1,3-dihydro-2H-imidazo[4,5-c]quinolin-2-one (29); (S)-1-(3,3-difluoro-1-isopropylpiperidin-4-yl)-8-(6-methoxypyridin-3-yl)-3-methyl-1,3-dihydro-2H-imidazo[4,5-c]quinolin-2-one (30); (S)-1-(3,3-difluoro-1-methylpiperidin-4-yl)-8-(6-ethoxypyridin-3-yl)-3-methyl-1,3-dihydro-2H-imidazo[4,5-c]quinolin-2-one (31); (S)-1-(3,3-difluoro-1-methylpiperidin-4-yl)-7-fluoro-8-(6-methoxypyridin-3-yl)-3-methyl-1,3-dihydro-2H-imidazo[4,5-c]quinolin-2-one (32); (S)-1-(3,3-difluoro-1-(methyl-d3)piperidin-4-yl)-8-(6-methoxypyridin-3-yl)-3-methyl-1,3-dihydro-2H-imidazo[4,5-c]quinolin-2-one (33); (S)-1-(3,3-difluoro-1-methylpiperidin-4-yl)-8-(6-isopropoxypyridin-3-yl)-3-methyl-1,3-dihydro-2H-imidazo[4,5-c]quinolin-2-one (34); (S)-1-(3,3-difluoro-1-methylpiperidin-4-yl)-8-(6-(dimethylamino)pyridin-3-yl)-3-methyl-1,3-dihydro-2H-imidazo[4,5-c]quinolin-2-one (35); (S)-1-(3,3-difluoro-1-methylpiperidin-4-yl)-8-(6-methoxypyridin-3-yl)-3-(methyl-d3)-1,3-dihydro-2H-imidazo[4,5-c]quinolin-2-one (36); (S)-8-(6-cyclopropoxypyridin-3-yl)-1-(3,3-difluoro-1-methylpiperidin-4-yl)-3-methyl-1,3-dihydro-2H-imidazo[4,5-c]quinolin-2-one (37); (S)-1-(3,3-difluoro-1-methylpiperidin-4-yl)-8-(6-(3-(dimethylamino)azetidin-1-yl)pyridin-3-yl)-3-methyl-1,3-dihydro-2H-imidazo[4,5-c]quinolin-2-one (38); (S)-1-(3,3-difluoro-1-methylpiperidin-4-yl)-8-(6-(methoxy-d3)pyridin-3-yl)-3-methyl-1,3-dihydro-2H-imidazo[4,5-c]quinolin-2-one (39); (S)-1-(3,3-difluoro-1-methylpiperidin-4-yl)-3-methyl-8-(6-((1R,5R)-(2-methyl-2,6-diazabicyclo[3.2.0]heptan-6-yl)pyridin-3-yl)-1,3-dihydro-2H-imidazo[4,5-c]quinolin-2-one (40); (S)-1-(3,3-difluoro-1-methylpiperidin-4-yl)-3-methyl-8-(6-((1S,5S)-(2-methyl-2,6-diazabicyclo[3.2.0]heptan-6-yl)pyridin-3-yl)-1,3-dihydro-2H-imidazo[4,5-c]quinolin-2-one (41)

The terms of the present invention are explained as follows:

The terms "improving" and "treating" are used interchangeably to mean reducing, inhibiting, preventing or stabilizing the occurrence or progression of a disease (e.g., the disease or disorder described herein) In addition to, but not limited to, therapeutic benefits and/or prophylactic benefits.

"Disease" refers to any disorder or disorder that damages or interferes with the normal functioning of a cell, organ or tissue.

"marker" refers to any alteration associated with a disease or disorder. For example, any protein or polynucleic acid that has altered the expression level or activity associated with the disease or disorder.

In this context, "including", "containing" and "possessed" and similar terms have the meanings given to them in the patent law; "substantially consisting" or "essentially" has the same meaning as given in the patent law, and the term is open, allowing the presence of objects other than the cited object as long as the basis or new feature of the referenced object does not change due to the presence of an object other than the cited object, but does not include the implementation of the prior art.

The terms "antagonists" and "inhibitors" as used herein are used interchangeably and refer to the ability of a compound or agent to inhibit the biological function of a target protein or polypeptide, for example by inhibiting the activity or expression of a protein or polypeptide. Although some of the antagonists herein interact with specific target proteins or polypeptides (e.g., bind to ATM), the compounds also inhibit the biological activity of the target protein or polypeptide by interacting with other members of the signal transduction pathway that targets the protein or polypeptide Including within the definition, those that inhibit the development of tumors that develop, grow, or diffuse, or that are associated with unwanted immune responses exhibited by autoimmune diseases.

The term "anti-cancer agent", "antineoplastic agent" or "chemotherapeutic agent" as used herein refers to any agent useful in the treatment of a tumor disorder. A class of anticancer agents includes chemotherapeutic agents. "Chemotherapy" refers to one or more chemotherapeutic agents and/or other agents administered in a variety of ways, including intravenous, oral, subcutaneous, intramuscular, intraperitoneal, intravesical, transdermal, buccal, or inhaled way.

As used herein, the term "cell proliferation" refers to an increase in the number of cells as a result of cell division, as well as cell growth (e.g., increased size) that is consistent with the proliferation signal by the cell morphology.

As used herein, the term "co-administration" refers to the use of two or more drugs at the same time, as well as compositions that are present at the same time using two or more agents, as well as at different times administering or administering two or more drugs and/or their metabolites alone.

As used herein, the term "effective amount" or "effective therapeutic amount" means that the amount of the compound or pharmaceutical composition described herein is sufficient to achieve the intended use, including, but not limited to, treating the disease. In some embodiments, the amount is detected to be effective for killing or inhibiting the growth or spread of cancer cells; the size or number of tumors; or the severity level, stage and progression of cancer. The amount of effective treatment may vary depending on the intended application, such as in vitro or in vivo, condition and severity of the disease, subject age, weight, or mode of administration. The term also applies to dosages that will induce target cells, for example, to reduce cell migration by a specific response. The specific dosage will depend on, for example, the particular compound selected, the subject species and their age/existing health status or health status, the route of administration, the severity of the disease, the combination with other agents, The administration time, the tissue to which it is administered, and the administration device.

The term "therapeutic effect" as used herein includes therapeutic benefits and/or prophylactic benefits. The prophylactic effect includes delaying or eliminating the onset of a disease or condition, delaying or eliminating the onset of symptoms or disorders of the disease, slowing, stopping or reversing a disease or condition, or any combination thereof.

As used herein, the term "signal transduction" is the process by which a stimulus or suppression signal is sent to the cell to initiate an intracellular response. The "modulator" of the signal transduction pathway means that the compound modulates one or more activity of cellular proteins that are mediated by specific signal transduction pathways.

The "modulator" may increase (agonist) the activity of the signaling molecules or inhibit (antagonist) signaling molecules.

The term "selective inhibition" as used herein refers to the ability of a compound to selectively reduce the target signaling activity compared to the target activity for off-target, by direct interaction or indirect interaction. For example, the activity of a compound to selectively inhibit ATM is at least about 2 times, about 3 times, about 5 times, about 10 times, about 20 times, about 50 times, about 100 times or more for the activity of ATR.

As used herein, the term "radiation therapy" refers to a subject that is exposed to a radiation emitter, such as, but not limited to, alpha-particles emitting radioactive nuclear elements (e.g., actinium and thorium radioactive nuclear elements) (e.g., beta emitters), conversion electron emitters (e.g., strontium-89 and samarium 153-EDTMP), or high energy radiation including, but not limited to, X-rays, gamma rays, and neutrons.

The term "subject" as used herein includes, but is not limited to, humans (e.g., any age group, e.g., a male or female (e.g., infant, child, adolescent) or adult subject (e.g., young adult, middle-aged adult or senior adult)) and/or other primates (e.g., cynomolgus monkeys, rhesus monkeys); mammals, including commercial-related mammals such as cattle, sheep, goats, pigs, horses, cats and/or dogs; and/or birds, including commercial-related birds such as chickens, geese, quails, ducks and/or turkeys.

As used herein, the term "in vivo" refers to an activity occurring within the subject body. Incident in rodents, such as rats, mice, guinea pigs, and the like, are also included in the body.

As used herein, the term "in vitro" refers to an event that occurs outside a body. For example, in vitro test involves any detection that occurs outside the body. In vitro assays include cell determination based on live or dead cells, as well as cell-free assays that are used in cells that are not intact.

The term "compound" as used herein is also intended to include salts of the general formula herein. The term also includes any solvate, hydrate and polymorph of any of the foregoing. In certain aspects of the invention described in this application, specific references to "solvate", "hydrate" or "polymorph" should not be construed. In other aspects of the invention that use the term "compound" without reference to these other forms, it is not intended to exclude such forms.

The salts of the compounds of the present invention are formed between the acid and the basic group of the compound, for example, the amino functional group. According to another preferred embodiment, the compound is a pharmaceutically acceptable acid addition salt.

The term "pharmaceutically acceptable" as used herein refers to a pharmaceutical composition that is suitable for use in contact with humans and other mammalian tissues without reasonable toxicity, irritation, allergic reactions, etc., and has reasonable interest/risk than the components. "Pharmaceutically acceptable salt" refers to any non-toxic salt that, upon administration to a recipient, can provide the compound of the invention, either directly or indirectly.

The acids commonly used to form pharmaceutically acceptable salts include inorganic acids such as hydrochloric acid, hydrobromic acid, sulfuric acid, hydroiodic acid and phosphoric acid, and organic acids such as trifluoroacetic acid, citric acid, maleic acid, oxalic acid, picric acid Acetic acid, adipic acid, alginic acid, aspartic acid, sulfuric acid, boric acid, butyric acid, valeric acid, camphoric acid, camphorsyl thiocyanate, digluconic acid, dodecyl sulfate, pivalic acid, formic acid, fumaric acid, hydroiodic acid, benzoic acid, 2-hydroxy-ethanesulfonic acid, fumaric acid, stearic acid, lactobionic acid, propionic acid lauric acid, oleic acid, nicotinic acid, lactic acid cinnamic acid, amber acid, mandelic acid, malic acid, tartaric acid, tartaric acid, lactic acid, pyruvic acid, pectic acid, methanesulfonic acid, pamoate, benzenesulfonic acid, persulfuric acid, palmitic acid, malonic acid, glycerophosphoric acid, 2-naphthalenesulfonic acid, P-toluenesulfonic acid, salicylic acid, ascorbic acid, 3-phenylpropionic acid, gluconic acid, glucuronic acid, phosphoric acid, glutamic acid, ethanesulfonic acid, p-bromobenzenesulfonic acid and carbonic acid, and related inorganic and organic acid.

As used herein, the term "hydrate" refers to a compound that includes stoichiometric or non-stoichiometric amounts of water bound by noncovalent intermolecular forces. The term "solvate" as used herein refers to a compound comprising a stoichiometric or non-stoichiometric amount of a solvent that is bound by non-covalent intermolecular forces such as water, dichloromethane, 2-propanol, acetone, methanol, ethanol or the like. Pharmaceutically acceptable solvates and hydrates are complexes that may include, for example, 1 to about 100, or 1 to about 10, or 1 to about 4, about 3, or about 2, a solvent or water molecule. It is to be understood that the term "compound" as used herein includes solvates, hydrates, and mixtures thereof of the compounds and compounds described.

The term "polymorph" as used herein refers to a solid crystalline form of a compound or a complex thereof. Different polymorphs of the same compound can exhibit different physical, chemical and/or spectral properties. Different physical properties include, but are not limited to, stability (e.g., heat, light or moisture), density, hygroscopicity, solubility, compressibility and dissolution rate.

The term "isomer" as used herein is a different compound having the same molecular formula. "Stereoisomers" are isomers only in the arrangement of atoms in different ways. The term "isomer" as used herein includes any and all geometric isomers and stereoisomers. For example, "isomers" include geometrical double bonds of cis and trans isomers, also known as E- and Z-isomers; R- and S-enantiomers; diastereomers, (D) Isomers and (L) isomers, their racemic mixtures, and other mixtures thereof, are disclosed herein.

The double bond around the carbon-carbon substituent is designated as the "Z" or "E" configuration, where the terms "Z" and "E" are used according to the IUPAC standard. Unless otherwise indicated, the structure depicts both the "E" and "Z" isomers.

The substitutable substituents surrounding the carbon-carbon double bonds may be referred to as "cis" or "trans", where "cis" means substituents on the same side of the double bond, and "trans" represents substituents on both sides. The arrangement of the surrounding carbon rings of the substituents may also be designated as "cis" or "trans". The term "cis" means the same side substituents in the ring plane, and the term "trans" means the substituents on both sides of the ring plane. Wherein the mixture of substituents on the same and opposite side of the plane of the two rings is represented as "cis/trans".

The term "enantiomer" as used herein is a stereoisomer of a pair of non-overlapping mirrors that are mutually overlapping. A mixture of enantiomers in any proportion may be referred to as a "racemic" mixture. The term "(±)" is used to specify the racemic mixture as appropriate. "Diastereomer" refers to a mirror image having at least two asymmetric atoms but whose stereoisomers are not each other. Absolute stereochemistry is specified according to the Cahn-Ingold-Prelog R-S system. When the compound is enantiomer, the stereochemistry of each chiral carbon can be specified by R or S. The absolute configuration of the compound is unknown and can be specified (+) or (−), depending on their direction of rotation of the polarized light in the wavelength of the sodium D line (right or left). Some of the materials described herein contain one or more asymmetric centers, and thus can produce enantiomers, diastereomers, and other stereoisomeric forms can be defined, in absolute stereologies for each asymmetric atom (R)— or (S)—, the pharmaceutical compositions and methods include all of these possible isomers, including racemic mixtures, optically pure forms and intermediate mixtures. The optically active (R)— and (S)— may also be prepared using chiral synthetic methods or chiral reagents, or by conventional techniques.

The term "enantiomeric excess" as used herein can be calculated using the formula shown below. In the examples shown below, the composition contains 90% of one enantiomer, for example, the S enantiomer, and contains 10% of the other enantiomer, for example, the R enantiomer.

$$ee\ value=(90-10)/100=80\%.$$

Thus, a composition containing 90% of one enantiomer and 10% of the other enantiomer is said to have an enantiomeric excess of 80%. Some of the compositions described herein contain at least about 50% enantiomeric excess, about 75%, about 90%, about 95%, or about 99% of the S enantiomer. In other words, the composition comprises an enantiomeric excess of the S enantiomer in the R enantiomer. In other embodiments, some of the compositions described herein contain at least about 50% enantiomeric excess, about 75%, about 90%, about 95%, or about 99% of the R enantiomer. In other words, the composition comprises an enantiomeric excess of the R enantiomer in the S enantiomer. For example, an isomer/enantiomer may, in some embodiments, provide the ee value of the corresponding enantiomer, and may also be referred to as "optical enrichment", "enantiomerically enriched", "enantiomerically pure" and "non-racemic", which are used interchangeably herein. These terms mean that the weight percentage of one of the enantiomers is greater than the amount of the control mixture of the composition than the racemic composition in one enantiomer (e.g., greater than 1:1 by weight). For example, the enantiomerically enantiomer of the S enantiomer is present at about 75% by weight of the enantiomer of the enantiomer, e.g., greater than about 50% by weight of the compound, At least about 80% by weight. In some embodiments, the enrichment is greater than about 80% by weight, providing a "substantially enantiomerically enriched", "substantially enantiomerically pure" or "substantially nonracial" Means that the weight of the enantiomer has at least 85% of the composition, such as at least about 90% by weight of the formulation, and further, for example, at least about 95% by weight, relative to one of the other enantiomers. In certain embodiments, the compounds provided herein may be present in an amount of from about 90% by weight of at least one enantiomer. In other embodiments, the compound may be present in an amount of at least about 95%, about 98%, or about 100% by weight of an enantiomer. In some embodiments, the compounds are (S)- and (R)-racemic mixtures. In other embodiments, there is provided a process wherein the individual compound (S) of the mixture is predominantly a mixture of compounds or (R)— is a mixture of predominantly present compounds. For example, the compound mixture has greater than about 55%, about 60%, about 65%, about 70%, about 75%, about 80%, about 85%, about 90%, about 95%, about 96%, about 97%, about 98%, about 99%, about 99.5%, or more. In other embodiments, the mixture of compounds has a (S)-enantiomeric excess of greater than about 55% to about 99.5%, greater than about 60% to about 99.5%, greater than about 65% to about 99.5%, greater than about 70% To about 99.5%, greater than about 75% to about 99.5%, greater than about 80% to about 99.5%, greater than about 85% to about 99.5% Greater than about 96% to about 99.5%, greater than about 97% to about 99.5%, greater than about 98% to greater than about 99.5%, greater than about 99% to about 99.5%, or greater. In other embodiments, the compound mixture (R)-enantiomer purity has greater than about 55%, about 60%, about 65%, about 70%, about 75%, about 80%, about 85%, about 90% About 95%, about 96%, about 97%, about 98%, about 99%, about 99.5% or more. In other embodiments, the mixture of compounds has an (R)-enantiomeric excess of greater than about 55% to about 99.5%, greater than about 60% to about 99.5%, greater than about 65% to about 99.5%, greater than about 70% To about 99.5%, greater than about 75% to about 99.5%, greater than about 95% to about 99.5%, greater than about 85% to about 99.5% Greater than about 96% to about 99.5%, greater than about 97% to about 99.5%, greater than about 98% to greater than about 99.5%, greater than about 99% to about 99.5% or more.

In other embodiments, the compound mixture comprises, in addition to their stereochemical orientation, i.e., (S)— or (R)— the same chemical entity. For example, if there is a —CH(R)— unit in the compound, and R is not hydrogen, then —CH(R)— is the same chemical entity as the (S)- or (R)-stereochemistry orientation. In some embodiments, the (S)-isomer in the mixture of the same chemical entities is present in an (S)-enantiomeric excess of greater than about 55% to about 99.5%, greater than about 60% to about 99.5%, greater than about 65% to about 99.5%, greater than about 90% to about 99.5%, greater than about 90% to about 99.5%, greater than about 90% to about 99.5 % To about 99.5%, greater than about 95% to about 99.5%, greater than about 96% to about 99.5%, greater than about 97% to about 99.5%, greater than about 98% to greater than about 99.5%, greater than about 99% to about 99.5% or more.

In another embodiment, the (R)-isomer is present in the same chemical entity (except for its stereochemical orientation) relative to the (S)-isomer, at about 55%, about 60%, about 65 About 90%, about 95%, about 85%, about 90%, about 95%, about 96%, about 97%, about 98%, about 99%, about 99.5% or greater. In some embodiments, the (R)-enantiomeric excess in the mixture of the same chemical entity (except its stereochemical orientation) of greater than about 55% to about 99.5%, greater than about 60% to about 99.5%, greater than about 75% to about 99.5%, greater than about 75% to about 99.5%, greater than about 75% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

Enantiomers can be isolated from racemic mixtures by any method known to those skilled in the art, including chiral high performance liquid chromatography (HPLC), chiral salt formation and crystallization, or non-synthetic synthesis.

The optical isomers can also be obtained by cleaving the racemic mixture in a conventional manner with an optically active acid or base, for example, by forming a diastereomeric salt. Examples of suitable acids include, but are not limited to, tartaric acid, diacetyl, dibenzoyl, dimethoyltartaric acid and camphorsulfonic acid. Separation of isomers from the mixture of optically active bases of these salts can be achieved by diastereomeric crystallization. Alternatively, the reaction of the open compound with the optically pure acid or optically pure isocyanate of the activated form involves the synthesis of covalent diastereomeric molecules. The synthetic enantiomers can be isolated by conventional methods such as chromatography, distillation, crystallization or sublimation, followed by hydrolysis to provide enantiomerically enriched compounds. The optically active compound can also be obtained by using an active material. In some embodiments, these isomers may be in the form of free acids, free bases, esters or salts.

In certain embodiments, the pharmaceutically acceptable form is a tautomer. As used herein, the term "tautomer" is a type of isomer that includes at least one form of migration and alteration of two or more interconverted compounds derived from hydrogen atoms and covalent bonds (e.g. a single bond to a double bond, a triple bond to a single bond, or vice versa). "Tautomerism" includes proton or proton migration tautomerism, which is considered a subset of acid-base chemistry. "Proton transfer tautomerism" involves proton migration accompanied by a bond change. The exact proportion of tautomer depends on several factors, including temperature, solvent and pH. Among them, tautomerism is possible (for example, in solution), and the chemical equilibrium of the tautomer can be reached. Tautomerism (i.e., the reaction to provide a tautomer pair) can be catalyzed by an acid or base, or presence or absence of an external agent can occur. Such as tautomeric additions include, but are not limited to, ketones to enol; amides to imides; enamines to imines; and one form of enamines to different enamines. Specific examples of ketone to enol tautomer are pentane-2,4-dione and 4-hydroxypent-3-en-2-one tautomer. Another example of tautomerism is phenol and ketone tautomerism. Specific examples of phenol and ketone tautomer are pyridine 4-phenols and pyridine-4-(1H)-one tautomer.

Unless otherwise indicated, it is meant that the structures described herein include compounds that exist only in one or more isotopically enriched atoms. For example, the compound has a structure in which one hydrogen is replaced by deuterium or tritium, or the carbon 13 or carbon 14 within the disclosed range is enriched.

The present disclosure also includes those "isotopically labeled derivatives" which are pharmaceutically acceptable forms of those compounds recited herein, except that one or more atoms are of a different atomic mass generally found in nature. Examples of isotopes that can be incorporated into the disclosed compounds include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{18}F$, and $^{36}Cl$. Certain isotopically labeled disclosed compounds (e.g., those labeled $^{3}H$ and $^{14}C$) are useful for the determination of compounds and/or substrate tissue distribution. Tritium (i.e., $^{3}H$) and carbon 14 (i.e., $^{14}C$) isotopes can be readily prepared and tested. In addition, substitutions with heavier isotopes such as deuterium (i.e., $^{2}H$ or D) may provide certain therapeutic advantages resulting from greater metabolic stability (e.g., increasing the half-life or reduced dose requirements in vivo). Isotope-labeled disclosed compounds can generally be prepared by replacing an isotopically labeled reagent with a non-isotope-labeled reagent. In some embodiments, provided herein may also contain one or more non-natural atomic isotopes to form such compounds. All isotopic variants of the disclosed compounds are used herein, whether radioactive or not, within the scope of this disclosure. In some embodiments, the radiolabeled compound may be used to study the metabolic and tissue distribution of the compound to alter the metabolic pathway, or rate or other biological function.

As used herein, the term "stereoisomer" refers to enantiomers and diastereomers.

The term "halo" or "halogen" as used herein refers to any radical of fluorine, chlorine, bromine or iodine.

As used herein, the term "alkyl" refers to a straight or branched chain consisting of carbon and hydrogen atoms, not including unsaturated, having from 1 to 10 carbon atoms, preferably from 1 to 8 carbon atoms hydrocarbon chain. "Lower alkyl" refers to an alkyl group (including 1 and 4 carbon atoms) of 1 to 4 carbon atoms.

The term "aryl alkyl" refers to a moiety in which an alkyl hydrogen atom is substituted with an aryl group.

The term "alkenyl" refers to a straight or branched hydrocarbon chain having from 2 to 10, preferably from 2 to 4 carbon atoms, having at least one double bond. When the alkenyl group is attached to the nitrogen atom, it is preferred not to directly link such groups through carbon with a double bond.

The term "alkoxy" refers to an —O-alkyl group comprising from 1 to 10 carbon atoms from linear, branched, saturated cyclic structures and combinations thereof, via oxygen to the parent molecular structure. For example, methoxy, ethoxy, propoxy, isopropoxy, butoxy, cyclopropyloxy, cyclobutyloxy, cyclohexyloxy and the like. "Lower alkoxy" refers to an alkoxy group containing from one to six carbons.

The term "alkynyl" refers to a straight or branched hydrocarbon chain containing at least one triple bond, from 2 to 10 carbon atoms (i.e., C2-10 alkynyl), preferably from 2 to 4 carbon atoms of a straight chain hydrocarbon group. When the alkynyl group is attached to a nitrogen atom, it is preferred not to directly link such groups through carbon having a triple bond.

The term "alkylene" refers to a divalent straight chain bridge of 1 to 5 carbon atoms (e.g., —(CH$_2$)$_x$— wherein x is 1-5) linked by a single bond, which may be substituted by 1-3 alkyl substitution.

The term "cycloalkyl" and "cycloalkenyl" as used herein include saturated and partially saturated cyclic hydrocarbon alkyl groups having from 3 to 12 carbon atoms, preferably from 3 to 8 carbon atoms, and more preferably from 3 to 6 carbon atoms.

The term "Ar" or "aryl" refers to an aromatic cyclic group containing 6 to 14 carbon atoms (e.g., 6 membered monocyclic, 10 membered bicyclic). Exemplary aryl groups include phenyl, naphthyl and biphenyl.

The term "heterocycle", "heterocycloed" or "heterocyclyl" refers to a fully saturated or partially unsaturated cyclic group such as 3-7 membered monocyclic, 7-12 membered bicyclic, 15 membered tricyclic ring system having at least one heteroatom in at least one ring, wherein 0, 1, 2 or 3 atoms of each ring may be substituted with a substituent. Each ring of a heterocyclic group containing a heteroatom may have 1, 2, 3 or 4 heteroatoms selected from the group consisting of a nitrogen atom, an oxygen atom and/or a sulfur atom, wherein the nitrogen and sulfur heteroatoms may optionally be oxidized, and the nitrogen heteroatom may be optionally quaternized. The heterocyclic group may be attached at any heteroatom or carbon atom of the ring or ring system.

The term "substituent" refers to a group that is "substituted" on any of the functional groups described herein, for example, alkyl, alkenyl, alkynyl, cycloalkyl, cycloalkenyl, aryl base, heterocyclyl, or heteroaryl group. Suitable substituents include, but are not limited to, halogen, CN, NO$_2$, OR, SR, S(O)$_2$OR, NRR', C1-C2 perfluoroalkyl, C1-C2 perfluoroalkoxy, (NR)NRR', N(NR)NRR', N(NR)NRR', N(NR)NRR', C(O)(O)R", S(O)$_2$R", R', C(O)R', C(O)R", N(R)(CH$_2$)$_n$OH, (CH$_2$)$_n$OR, (CH$_2$)$_n$C(O)NRR', NRS(O)$_2$R' wherein n is independently 0-6, including 0 and 6. Each R is independently hydrogen, C1-C4 alkyl or C3-C6 cycloalkyl. Each R' is independently hydrogen, alkenyl, alkynyl, C3-C6 cycloalkyl, aryl, heterocyclyl, heteroaryl, C1-C4 alkyl or substituted by C3-C5 cycloalkyl, aryl, Heterocyclyl or heteroaryl substituted C—C4 alkyl. Each R" is independently C3-C6 cycloalkyl, aryl, heterocyclyl, heteroaryl, C1-C4 alkyl or substituted by C3-C6 cycloalkyl, aryl, heterocyclyl or heteroaryl C1-C4 alkyl. Each C3-C5 cycloalkyl, aryl, heterocyclyl, heteroaryl and C1-C4 alkyl in each R, R' and R" may be optionally substituted with halogen, CN, C1-C4 alkyl, OH, C1-C4 alkoxy, NH$_2$, C1-C4 alkylamino, C1-C4 dialkylamino, C1-C2 perfluoroalkyl, C1-C2 perfluoroalkoxy or 1,2-methylenedioxy.

The term "oxo"; refers to an oxygen atom that forms a carboxyl group when attached to a carbon which forms an N-oxide when attached to nitrogen and which forms a sulfoxide or sulfone when attached to sulfur.

The term "acyl" refers to an alkylcarbonyl, cycloalkylcarbonyl, arylcarbonyl, heterocyclylcarbonyl or heteroarylcarbonyl substituent, any of which may be further substituted with a substituent.

The term "CDCl$_3$" refers to deuterated chloroform.

The term "DMSO-d$_6$" refers to deuterated dimethylsulfoxide

The term "LC-MS: (ESI)" refers to electrospray ionization liquid chromatography mass spectrometry The term "alteration" as used herein is defined as a change in the relative physiological state. Exemplary changes include mutations, deletions, fusion with other proteins, overexpression or low expression.

The description of the enumeration of chemical groups in any definition of the variables herein includes defining the variable as a combination of any single group or enumerated group. The description of the embodiments of the variables herein includes this embodiment as any single embodiment or in combination with any other embodiment or part thereof. The description of the embodiments of this embodiment includes this embodiment as any single embodiment or in combination with any other embodiment or part thereof.

The compounds of the present invention may contain one or more asymmetric centers and thus appear as racemates and racemic mixtures, single enantiomers, individual diastereomers and diastereomeric mixtures. All such isomeric forms of these compounds are expressly included in the present invention. The compounds of the present invention may also be presented in a variety of tautomeric forms, in which case the invention clearly includes all tautomeric forms of the compounds described herein. All such isomeric forms of such compounds are included in the present invention. All crystalline forms of the compounds described herein are expressly included in the present invention.

Figure 1B:
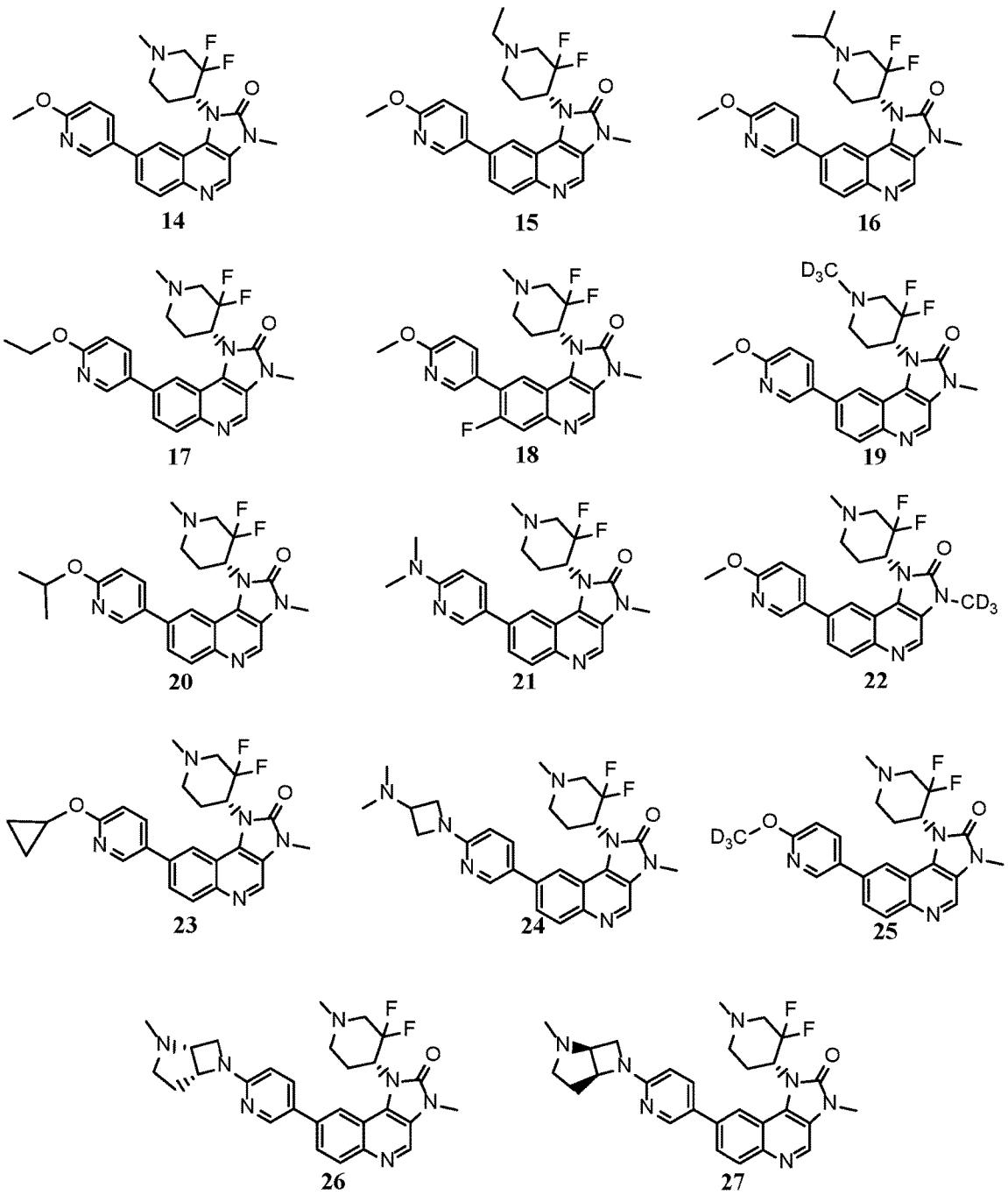
Figure 1C:
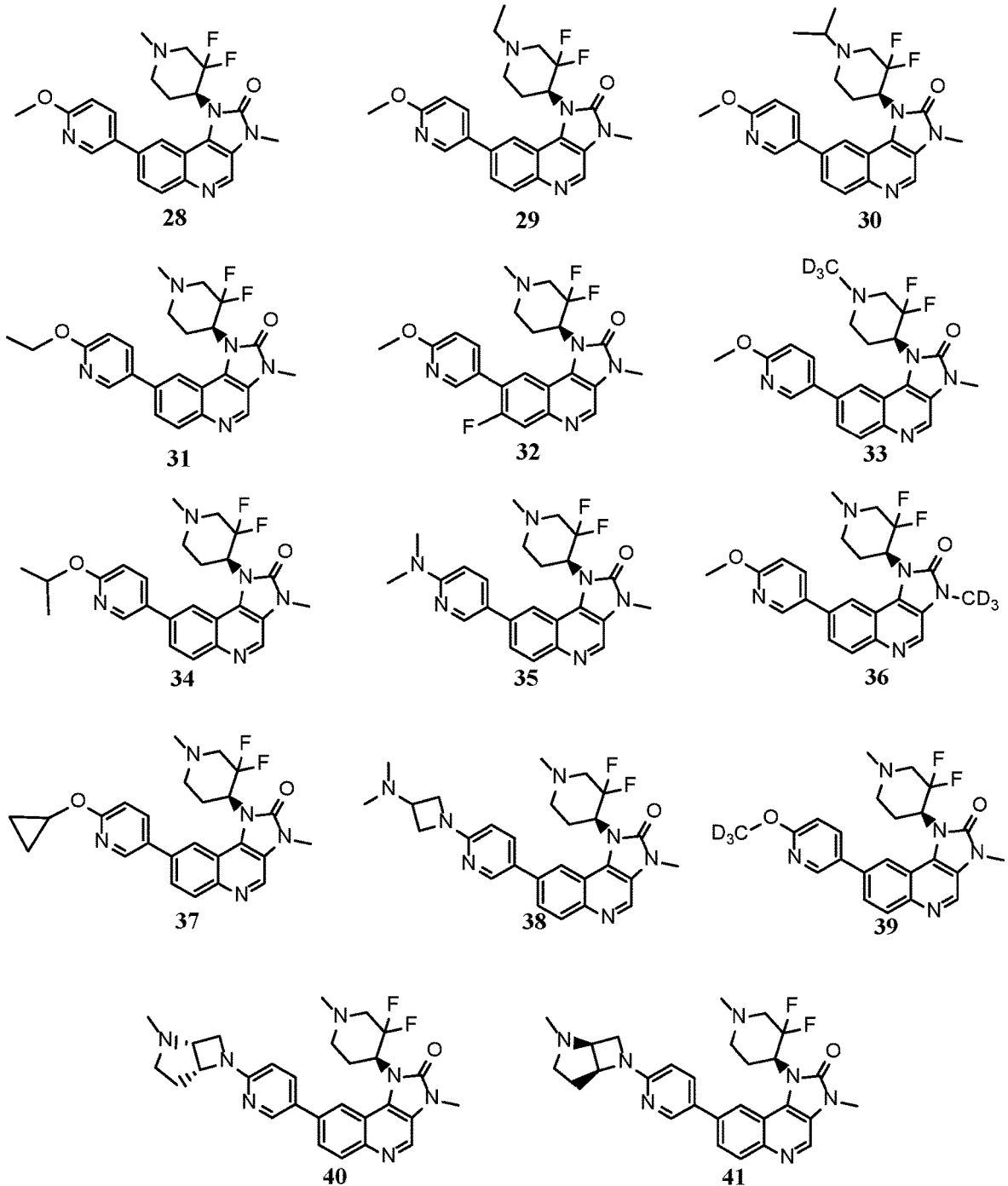

The compounds of the present invention:
In one aspect, the present invention provides compounds of formula (I):
  or a salt thereof; or a hydrate, solvate or polymorph thereof; wherein:
  Wherein R1 is independently selected from OC1-3 alkyl, OC3-5 cycloalkyl, OC1-C3 deuterated alkyl, dialkyl amine, substituted C4-C6 cycloamine or diazabicyclo amine;
  R2 is independently selected from hydrogen or fluoro;
  R3 is independently selected from methyl or deuterated methyl;
  R4 is independently selected from C1-C3 alkyl or C1-C3 deuterated alkyl In another embodiment, the present invention provides compounds of formula (II):
  or a salt thereof; or a hydrate, solvate or polymorph thereof; wherein:
  R1 is independently selected from OC1-3 alkyl, OC3-5 cycloalkyl, OC1-C3 deuterated alkyl, dialkyl amine, substituted C4-C6 cycloamine or diazabicyclo amine;

R2 is independently selected from hydrogen or fluoro;
R3 is independently selected from methyl or deuterated methyl;
R4 is independently selected from C1-C3 alkyl or C1-C3 deuterated alkyl;

In another embodiment, the present invention provides a compound of formula (III):
or a salt thereof; or a hydrate, solvate or polymorph thereof; wherein:
R1 is independently selected from OC1-3 alkyl, OC3-5 cycloalkyl, OC1-C3 deuterated alkyl, dialkyl amine, substituted C4-C6 cycloamine or diazabicyclo amine;
R2 is independently selected from hydrogen or fluoro;
R3 is independently selected from methyl or deuterated methyl;
R4 is independently selected from C1-C3 alkyl or C1-C3 deuterated alkyl;

Representative compounds of the present invention are compounds 1-41 shown in FIG. 1 A-C. In these examples, the stereochemistry at the chiral carbon atom is independently R/S, R or S, unless specifically indicated. The structures described herein include structures of the following compounds 1-41 with reference to FIG. 1 A-C, which may certain NH, NH$_2$ (amino) and OH (hydroxy) groups in which the corresponding hydrogen atoms are not clearly shown; however, they will be read as NH, NH$_2$ or OH as appropriate. In some structures, drawing a rod bond means a methyl group.

Representative compounds of the present invention are as followings:
(R/S)-1-(3,3-difluoro-1-methylpiperidin-4-yl)-8-(6-methoxypyridin-3-yl)-3-methyl-1,3-dihydro-2H-imidazo[4,5-c]quinolin-2-one (1)
(R/S)-1-(1-ethyl-3,3-difluoropiperidin-4-yl)-8-(6-methoxypyridin-3-yl)-3-methyl-1,3-dihydro-2H-imidazo[4,5-c]quinolin-2-one (2)
(R/S)-1-(3,3-difluoro-1-isopropylpiperidin-4-yl)-8-(6-methoxypyridin-3-yl)-3-methyl-1,3-dihydro-2H-imidazo[4,5-c]quinolin-2-one (3)
(R/S)-1-(3,3-difluoro-1-methylpiperidin-4-yl)-8-(6-ethoxypyridin-3-yl)-3-methyl-1,3-dihydro-2H-imidazo[4,5-c]quinolin-2-one (4)
(R/S)-1-(3,3-difluoro-1-methylpiperidin-4-yl)-7-fluoro-8-(6-methoxypyridin-3-yl)-3-methyl-1,3-dihydro-2H-imidazo[4,5-c]quinolin-2-one (5)
(R/S)-1-(3,3-difluoro-1-(methyl-d3)piperidin-4-yl)-8-(6-methoxypyridin-3-yl)-3-methyl-1,3-dihydro-2H-imidazo[4,5-c]quinolin-2-one (6)
(R/S)-1-(3,3-difluoro-1-methylpiperidin-4-yl)-8-(6-isopropoxypyridin-3-yl)-3-methyl-1,3-dihydro-2H-imidazo[4,5-c]quinolin-2-one (7)
(R/S)-1-(3,3-difluoro-1-methylpiperidin-4-yl)-8-(6-(dimethylamino)pyridin-3-yl)-3-methyl-1,3-dihydro-2H-imidazo[4,5-c]quinolin-2-one (8)
(R/S)-1-(3,3-difluoro-1-methylpiperidin-4-yl)-8-(6-methoxypyridin-3-yl)-3-(methyl-d3)-1,3-dihydro-2H-imidazo[4,5-c]quinolin-2-one (9)
(R/S)-8-(6-cyclopropoxypyridin-3-yl)-1-(3,3-difluoro-1-methylpiperidin-4-yl)-3-methyl-1,3-dihydro-2H-imidazo[4,5-c]quinolin-2-one (10)
(R/S)-1-(3,3-difluoro-1-methylpiperidin-4-yl)-8-(6-(3-(dimethylamino)azetidin-1-yl)pyridin-3-yl)-3-methyl-1,3-dihydro-2H-imidazo[4,5-c]quinolin-2-one (11)
(R/S)-1-(3,3-difluoro-1-methylpiperidin-4-yl)-8-(6-(methoxy-d3)pyridin-3-yl)-3-methyl-1,3-dihydro-2H-imidazo[4,5-c]quinolin-2-one (12)
(R/S)-1-(3,3-difluoro-1-methylpiperidin-4-yl)-3-methyl-8-(6-((1R,5R/1S,5S)-(2-methyl-2,6-diazabicyclo[3.2.0]heptan-6-yl)pyridin-3-yl)-1,3-dihydro-2H-imidazo[4,5-c]quinolin-2-one (13)
(R)-1-(3,3-difluoro-1-methylpiperidin-4-yl)-8-(6-methoxypyridin-3-yl)-3-methyl-1,3-dihydro-2H-imidazo[4,5-c]quinolin-2-one (14)
(R)-1-(1-ethyl-3,3-difluoropiperidin-4-yl)-8-(6-methoxypyridin-3-yl)-3-methyl-1,3-dihydro-2H-imidazo[4,5-c]quinolin-2-one (15)
(R)-1-(3,3-difluoro-1-isopropylpiperidin-4-yl)-8-(6-methoxypyridin-3-yl)-3-methyl-1,3-dihydro-2H-imidazo[4,5-c]quinolin-2-one (16)
(R)-1-(3,3-difluoro-1-methylpiperidin-4-yl)-8-(6-ethoxypyridin-3-yl)-3-methyl-1,3-dihydro-2H-imidazo[4,5-c]quinolin-2-one (17)
(R)-1-(3,3-difluoro-1-methylpiperidin-4-yl)-7-fluoro-8-(6-methoxypyridin-3-yl)-3-methyl-1,3-dihydro-2H-imidazo[4,5-c]quinolin-2-one (18)
(R)-1-(3,3-difluoro-1-(methyl-d3)piperidin-4-yl)-8-(6-methoxypyridin-3-yl)-3-methyl-1,3-dihydro-2H-imidazo[4,5-c]quinolin-2-one (19)
(R)-1-(3,3-difluoro-1-methylpiperidin-4-yl)-8-(6-isopropoxypyridin-3-yl)-3-methyl-1,3-dihydro-2H-imidazo[4,5-c]quinolin-2-one (20)
(R)-1-(3,3-difluoro-1-methylpiperidin-4-yl)-8-(6-(dimethylamino)pyridin-3-yl)-3-methyl-1,3-dihydro-2H-imidazo[4,5-c]quinolin-2-one (21)
(R)-1-(3,3-difluoro-1-methylpiperidin-4-yl)-8-(6-methoxypyridin-3-yl)-3-(methyl-d3)-1,3-dihydro-2H-imidazo[4,5-c]quinolin-2-one (22)
(R)-8-(6-cyclopropoxypyridin-3-yl)-1-(3,3-difluoro-1-methylpiperidin-4-yl)-3-methyl-1,3-dihydro-2H-imidazo[4,5-c]quinolin-2-one (23)
(R)-1-(3,3-difluoro-1-methylpiperidin-4-yl)-8-(6-(3-(dimethylamino)azetidin-1-yl)pyridin-3-yl)-3-methyl-1,3-dihydro-2H-imidazo[4,5-c]quinolin-2-one (24)
(R)-1-(3,3-difluoro-1-methylpiperidin-4-yl)-8-(6-(methoxy-d3)pyridin-3-yl)-3-methyl-1,3-dihydro-2H-imidazo[4,5-c]quinolin-2-one (25)
(R)-1-(3,3-difluoro-1-methylpiperidin-4-yl)-3-methyl-8-(6-((1R,5R)-(2-methyl-2,6-diazabicyclo[3.2.0]heptan-6-yl)pyridin-3-yl)-1,3-dihydro-2H-imidazo[4,5-c]quinolin-2-one (26)
(R)-1-(3,3-difluoro-1-methylpiperidin-4-yl)-3-methyl-8-(6-((1S,5S)-(2-methyl-2,6-diazabicyclo[3.2.0]heptan-6-yl)pyridin-3-yl)-1,3-dihydro-2H-imidazo[4,5-c]quinolin-2-one (27)
(S)-1-(3,3-difluoro-1-methylpiperidin-4-yl)-8-(6-methoxypyridin-3-yl)-3-methyl-1,3-dihydro-2H-imidazo[4,5-c]quinolin-2-one (28)
(S)-1-(1-ethyl-3,3-difluoropiperidin-4-yl)-8-(6-methoxypyridin-3-yl)-3-methyl-1,3-dihydro-2H-imidazo[4,5-c]quinolin-2-one (29)
(S)-1-(3,3-difluoro-1-isopropylpiperidin-4-yl)-8-(6-methoxypyridin-3-yl)-3-methyl-1,3-dihydro-2H-imidazo[4,5-c]quinolin-2-one (30)
(S)-1-(3,3-difluoro-1-methylpiperidin-4-yl)-8-(6-ethoxypyridin-3-yl)-3-methyl-1,3-dihydro-2H-imidazo[4,5-c]quinolin-2-one (31)
(S)-1-(3,3-difluoro-1-methylpiperidin-4-yl)-7-fluoro-8-(6-methoxypyridin-3-yl)-3-methyl-1,3-dihydro-2H-imidazo[4,5-c]quinolin-2-one (32)
(S)-1-(3,3-difluoro-1-(methyl-d3)piperidin-4-yl)-8-(6-methoxypyridin-3-yl)-3-methyl-1,3-dihydro-2H-imidazo[4,5-c]quinolin-2-one (33)

(S)-1-(3,3-difluoro-1-methylpiperidin-4-yl)-8-(6-isopropoxypyridin-3-yl)-3-methyl-1,3-dihydro-2H-imidazo[4,5-c]quinolin-2-one (34)

(S)-1-(3,3-difluoro-1-methylpiperidin-4-yl)-8-(6-(dimethylamino)pyridin-3-yl)-3-methyl-1,3-dihydro-2H-imidazo[4,5-c]quinolin-2-one (35)

(S)-1-(3,3-difluoro-1-methylpiperidin-4-yl)-8-(6-methoxypyridin-3-yl)-3-(methyl-d3)-1,3-dihydro-2H-imidazo[4,5-c]quinolin-2-one (36)

(S)-8-(6-cyclopropoxypyridin-3-yl)-1-(3,3-difluoro-1-methylpiperidin-4-yl)-3-methyl-1,3-dihydro-2H-imidazo[4,5-c]quinolin-2-one (37)

(S)-1-(3,3-difluoro-1-methylpiperidin-4-yl)-8-(6-(3-(dimethylamino)azetidin-1-yl)pyridin-3-yl)-3-methyl-1,3-dihydro-2H-imidazo[4,5-c]quinolin-2-one (38)

(S)-1-(3,3-difluoro-1-methylpiperidin-4-yl)-8-(6-(methoxy-d3)pyridin-3-yl)-3-methyl-1,3-dihydro-2H-imidazo[4,5-c]quinolin-2-one (39)

(S)-1-(3,3-difluoro-1-methylpiperidin-4-yl)-3-methyl-8-(6-((1R,5R)-(2-methyl-2,6-diazabicyclo[3.2.0]heptan-6-yl)pyridin-3-yl)-1,3-dihydro-2H-imidazo[4,5-c]quinolin-2-one (40)

(S)-1-(3,3-difluoro-1-methylpiperidin-4-yl)-3-methyl-8-(6-((1S,5S)-(2-methyl-2,6-diazabicyclo[3.2.0]heptan-6-yl)pyridin-3-yl)-1,3-dihydro-2H-imidazo[4,5-c]quinolin-2-one (41)

The synthesis of the compounds of the general formula herein can be readily carried out by ordinary synthetic chemical technicians, for example, the related methods and intermediates disclosed herein. Each patent, patent application and publication mentioned herein, whether in a traditional magazine or only on the Internet, is incorporated herein by reference in its entirety.

Other methods of synthesizing compounds of the general formula herein can be readily modified from the references cited herein. The variation of these procedures and their optimization are within the capabilities of ordinary technical personnel.

The specific modes and compounds shown above are not intended to be limiting. The chemical structure in this scheme depicts a number of variables in which the chemical groups defined in the corresponding positions of the compounds of the formula (partial, atomic, etc.) are used to disinfect them accordingly, whether or not they are represented by the same variable name (For example, R1, R2, R, R', R'', X, etc.) The suitability of the chemical groups in the compound structure for the synthesis of another compound structure is within the capabilities of those of ordinary skill in the art. Other methods of the compounds of the general formula and their synthetic precursors, including those not expressly shown in the present disclosure, are within the scope of the chemical means of one of ordinary skill in the art. To reduce the competitive by-product, the method of optimizing the reaction conditions is known in the art. The methods described herein may additionally include steps prior to or after the steps described herein specifically to incorporate or remove suitable protecting groups, thereby ultimately capable of synthesizing herein. In addition, the individual synthetic steps may be carried out in a variable order or sequence to obtain the desired compound.

The process described herein contemplates the conversion of a compound of formula to another compound of formula. The transformation process refers to one or more chemical transformations that can be carried out in situ or separated from the intermediate compound. The transformation may include the use of techniques and protocols known in the art to react the starting compound or intermediate with additional reagents, including those recited in the references cited herein. The intermediates can be purified (e.g., filtered, distilled, sublimed, crystallized, ground, solid phase extracted and chromatographed) or used without purification.

The combination of the intended substituents and variables of the present invention is only those that result in the formation of stable compounds.

The present invention also provides a composition comprising an effective amount of a compound of any of the general formulas herein, or, if applicable, a pharmaceutically acceptable salt, solvate, hydrate, or polymorph of said compound; and acceptable carrier. Preferably, the compositions of the present invention are formulated for pharmaceutical use (pharmaceutical compositions), wherein the carrier is a pharmaceutically acceptable carrier. In view of compatibility with other ingredients of the formulation and in the case of a pharmaceutically acceptable carrier, the carrier must be "acceptable" and does not impair its acceptor in amounts typically used in the drug.

"Pharmaceutically acceptable carrier"; or "pharmaceutically acceptable excipient" includes any and all solvents, dispersion media, coatings, antibacterial and antifungal agents, isotonic and absorption delay agents, and the like. Pharmaceutically acceptable carriers or excipients do not disrupt the pharmacological activity of the disclosed compounds and are non-toxic when administered at a dosage of the amount of the compound sufficient to deliver. The use of such media and reagents for pharmaceutically active substances is well known in the art. Unless any conventional medium or reagent is incompatible with the active ingredient, the use of the therapeutic composition as disclosed herein is contemplated. Examples and excipients of pharmaceutically acceptable carriers include, but are not limited to, sugars such as lactose, sucrose and glucose; starches such as potato starch and corn starch; cellulose and derivatives thereof, such as carboxymethylcellulose sodium, cellulose acetate and ethyl cellulose; gelatin; tragacanth powder; talc; malt; cocoa butter and suppository waxes; oils such as peanut oil, safflower oil, cottonseed oil, olive oil, sesame oil, corn oil and soybean oil; diols such as polyethylene glycol and propylene glycol; esters such as ethyl oleate and ethyl laurate; agar; buffers such as magnesium hydroxide and aluminum hydroxide; alginic acid; aldehyde; phosphate; phosphate buffer; non-toxic compatible lubricants, for example, sodium lauryl sulfate and magnesium stearate; colorants; coating agents; release agents; sweeteners, flavoring agents and fragrances; (SEDDS) such as vitamin E polyethylene glycol 1000 succinate; surfactants for pharmaceutical dosage forms, for example, Tweens or other similar polymer delivery matrix; serum protein, for example, human serum albumin; glycine; sorbic acid; potassium sorbate; partial glyceride mixture of saturated vegetable fatty acids; water, salt or electrolytes such as protamine sulfate, potassium hydrogen phosphate, disodium hydrogen phosphate, sodium chloride And zinc salts; colloidal silica; magnesium trisilicate; polyvinylpyrrolidone; cellulose based materials; polyacrylates; waxes; and polyethylene-polyoxypropylene-block polymers. Cyclodextrins, for example, alpha, beta and gamma-cyclodextrins, or chemically modified derivatives, for example, hydroxyalkyl cyclodextrins including 2- and 3-hydroxypropyl cyclodextrins or other solubilized derivatives to improve the delivery of compounds.

The pharmaceutical compositions of the present invention may be administered in solid or liquid form, including oral administration, for example, irrigation (aqueous or non-aqueous solutions or suspensions), tablets (e.g., those for oral subcutaneous and systemic absorption), hard or soft capsules, pills, syrups, powders, granules, pastes applied to the tongue, duodenal route; parenteral administration, including intravenous, intraarterial, subcutaneous, intramuscular, for example, as a cream, ointment, gelling agent, aqueous or oily solution or suspension, for example, as a cream, ointment, gelling agent, or vaginal suppositories, creams or scaffolds; sublingual; administered locally via catheters or stents; intrathecally, or nasally, (For example, as a fine powder) or by inhalation (e.g., as a fine powder or a liquid aerosol).

Examples of suitable aqueous and nonaqueous carriers in pharmaceutical compositions include water, ethanol, polyols (e.g., glycerol, propylene glycol, polyethylene glycol, etc.), and suitable mixtures thereof, vegetable oils such as olive oil, and organic esters, such as ethyl oleate, are injected. By using a coating material, for example, lecithin, by maintaining the desired particle size of the dispersion, and by using the surfactant to maintain proper fluidity. These compositions may also contain adjuvants such as preservatives, wetting agents, emulsifiers, dispersants, lubricants, and/or antioxidants. The action of the compounds described herein to prevent microbes can be ensured by the inclusion of different antimicrobial and antifungal agents, for example, p-hydroxybenzoates, chlorobutanol, phenol sorbic acid and the like. It may also be in compositions comprising isotonic agents such as sugars, sodium chloride and the like. In addition, prolonged absorption of the injectable drug form may be achieved by comprising a delayed absorbent, such as aluminum monostearate and gelatin.

Methods of making such formulations or compositions include the compounds described herein and/or the steps associated with a chemotherapeutic vehicle and optionally one or more accessory ingredients. In general, the formulation is formed by uniformly and structuring the compound disclosed herein with a liquid carrier, or a finely divided solid carrier or both, and then, if necessary, the product is shaped. Unless any conventional excipient medium is incompatible with the compounds provided herein, for example by interacting with any other component of a pharmaceutically acceptable composition to produce any undesirable biological effects or deleterious effects, excipients are also intended to be within the scope of the present disclosure.

In some embodiments, the concentration of one or more of the disclosed compounds may be less than about 100%, about 90%, about 80%, about 70%, about 60%, about 50%, about 40%, about 14%, about 13%, about 12%, about 11%, about 10%, about 10%, about 5%, about 4%, about 3%, about 2%, about 1%, about 0.5%, about 0.4%, about 0.3%, about 0.2% About 0.09%, about 0.08%, about 0.07%, about 0.06%, about 0.05%, about 0.04%, about 0.03%, about 0.02%, about 0.01%, about 0.009%, about 0.008%, about 0.007%, about 0.006%, about 0.005%, about 0.004%, about 0.003%, about 0.002%, about 0.001%, about 0.0009%, about 0.0008%, about 0.0007%, about 0.0006%, about 0.0005%, about 0.0004% 0.0003% 0.0002% or about 0.0001% weight/weight ratio, weight/volume ratio, or volume/volume ratio.

In some embodiments, the concentration of one or more of the compounds disclosed herein may be greater than about 90%, about 80%, about 70%, about 60%, about 50%, about 40%, about 30%, about 20%, about 18.5%, about 18.25%, about 17.5%, about 17.25%, about 17%, about 16.5%, about 16.25%, about 16, about 15.5%, about 15.25%, about 15%, about 14.5%, about 14.25%, about 14%, about 13.5%, about 13.25%, about 13%, about 12.5%, about 12.25%, about 12%, about 11.5%, about 11.25%, about 11%, about 10.75%, about 10.5%, about 10%, about 9.75%, about 9.5%, about 9.25%, about 9%, about 8.75%, about 8.5%, about 8.25%, about 8%, about 7.75%, about 7.5%, about 7.25%, about 7%, about 6.75%, about 6.5%, about 6.25%, about 6%, about 5.75%, about 5.5%, about 5.25%, about 5%, About 4.75%, about 4.5%, about 4.25%, about 4%, about 3.75%, about 3.5%, about 3%, about 2.75%, about 2.50%, about 2.25%, about 2%, about 1.75%, about 1.50%, about 1.25%, about 1%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.009%, about 0.008%, about 0.007%, about 0.006%, about 0.005%, about 0.004%, about 0.003%, about 0.002%, about 0.001%, about 0.0009%, about 0.0008%, about 0.0007%, about 0.0006%, about 0.0005%, about 0.0004%, about 0.0003%, about 0.0002%, or about 0.0001% weight/weight ratio, weight/volume ratio, or volume/volume ratio. In some embodiments, the concentrations of one or more compounds disclosed herein may range from about 0.0001% to about 50%, from about 0.001% to about 40%, from about 0.01% to about 30%, from about 0.02% to about 20%, about 0.09% to about 24%, about 0.08% to about 23%, about 0.07% to about 22%, about 0.06% to about 24%, about 0.2% to about 20%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12%, about 1% to about 10% weight/weight ratio, weight/volume ratio or volume/volume ratio. In some embodiments, the concentration of one or more of the compounds disclosed herein may range from about 0.001% to about 10%, from about 0.01% to about 5%, from about 0.02% to about 4.5%, from about 0.03% To about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% weight/weight ratio, weight/volume ratio or volume/volume ratio.

In some embodiments, the amount of one or more compounds disclosed herein may be equal to or less than about 10 g, about 9.5 grams, about 9.0 grams, about 8.5 grams, about 8.0 grams, about 7.5 grams, about 7.0 grams, about 6.5 grams, about 6 grams, about 5.5 grams, about 5 grams, about 4.5 grams, about 4 grams, about 3.5 grams, about 3 grams, about 2.5 grams, about 2.0 grams, about 1.5 grams, about 1.0 grams, about 0.95, about 0.9 grams, about 0.85 grams, about 0.8 g, about 0.75 g, about 0.7 g, about 0.65 g, about 0.6 g, about 0.55 g, about 0.5 g, about 0.45 g, about 0.4 g, about 0.35 g, about 0.3 g, about 0.25 g, about 0.2 g, about 0.15 g, about 0.1 g, about 0.09 g, about 0.08 g, about 0.07 g, about 0.06 g, about 0.05 g, about 0.04 g, about 0.03 grams, about 0.02 grams, about 0.01 grams, about 0.009 grams, about 0.008 grams, about 0.007 grams, about 0.006 grams, about 0.005 grams, about 0.004 grams, about 0.003 grams, about 0.002 grams, about 0.001 grams, about 0.0009 grams, 0.0008 grams, about 0.0007 grams, about 0.0006 grams, about 0.0005 grams, about 0.0004 grams, about 0.0003 grams, about 0.0002 grams, or about 0.0001 grams. In some embodiments, the amount of one or more of the compounds disclosed herein may be in excess of about 0.0001 g, about 0.0002 g, 0.0003 g, about 0.0004 g, about 0.0005 g, about 0.0006 g, about 0.0007 g, about 0.0008 g, about 0.0009 grams, about 0.001 grams, 0.0015 grams, about 0.002 grams, about 0.0025 grams, about 0.003 grams, about 0.0035 grams, about 0.004 g, about 0.0045 g, about 0.005 g, about 0.0055 g, about 0.006 g, about 0.0065 g, about 0.007 g, about 0.0075 g, about 0.008 g, about 0.0085 g, about 0.009 g, about 0.0095 g, about 0.01 grams, about 0.015 grams, about 0.02 grams, about 0.025 grams, about 0.03 grams, about 0.035 grams, about 0.04 grams, about 0.045 grams, about 0.05 grams, about 0.055 grams, about 0.06 grams, about 0.065 grams, about 0.07 grams, about 0.075 grams, about 0.08 grams, about 0.085 grams, about 0.09 grams, about 0.095 grams, about 0.1 grams, about 0.15 grams, about 0.2 grams, about 0.25 grams, about 0.3 grams, about 0.35 grams, about 0.4 grams, about 0.45 grams, about 0.5 grams, about 0.55 grams, about 0.6 grams, about 0.65 grams, about 0.7 grams, about 0.75 grams, about 0.8 grams, about 0.85 grams, about 0.9 grams, about 0.95 grams, about 1 grams, about 1.5 grams, about 2 grams, about 2.5 grams, about 3 grams, about 3.5 grams, about 4 grams, about 4.5 grams, about 5 grams, about 5.5 grams, about 6 grams, about 6.5 grams, about 7 grams, about 7.5 grams, about 8 grams, about 8.5 grams, about 9 grams, about 9.5 grams, or about 10 g.

In some embodiments, the amount of one or more compounds disclosed herein may range from about 0.0001 grams to about 10 grams, from about 0.0005 grams to about 9 grams, from about 0.001 grams to about 0.5 grams, from about 0.001 grams to about 8 grams, from about 0.005 g to about 7 g, from 0.01 g to about 6 g, about 0.05 g to about 5 g, from about 0.1 g to about 4 g, from about 0.5 g to about 4 g, or from about 1 g to about 3 g.

In certain preferred embodiments, a pharmaceutical composition comprising an oral administration of a compound as disclosed herein, and a pharmaceutical excipient suitable for oral administration. In some embodiments, there is provided herein a pharmaceutical composition for oral administration: (1) optionally an effective amount of a disclosed compound; (2) an effective amount of one or more second agents; and (3) One or more pharmaceutically acceptable excipients for oral administration. In some embodiments, the pharmaceutical composition further comprises: (4) an effective amount of a third reagent.

In some embodiments, the pharmaceutical composition may be a liquid pharmaceutical composition suitable for oral administration. Pharmaceutical compositions suitable for oral administration may be used as discrete dosage forms, such as capsules, cachets, or tablets, or liquids, solutions, aerosol sprays or suspensions of a predetermined amount of active ingredient containing powder or granules, water or non-aqueous liquid, the liquid emulsion in water or water in the liquid emulsion. Such dosage forms may be prepared by any pharmaceutical method, but all methods include the step of preparing the composition by uniformly and intimately associating the active ingredient with a liquid carrier, a liposome or a finely divided solid carrier, or both. In general, the pharmaceutical composition is formed by mixing the active ingredient homogeneously and intimately with a liquid carrier or a finely divided solid carrier or both, and if necessary, shaping the product into the desired form. For example, the tablet may be one or more components that may be pressed or molded. The tablet may be formed by mixing the free-flowing form such as the active ingredient of the powder or granule, optionally with an excipient such as, but not limited to, a binder, a lubricant, an inert diluent and/or a surfactant or dispersant mix, press in the right machine. The molded tablets may be prepared by molding a mixture of powdered compounds moistened with an inert liquid diluent in a suitable machine. The tablets may optionally be uncoated, coated or nicked and may be formulated to provide a slow or controlled release of the active ingredient therein, thereby providing a sustained effect over a longer period of time, such as, for example, glyceryl monostearate or glyceryl distearate. Formulations for oral use may also be hard gelatin capsules in which the active ingredient may be mixed with an inert solid diluent, for example, calcium carbonate, calcium phosphate or kaolin, or as a soft gelatin capsule in which the active ingredient may be mixed with water or an oil medium, for example, peanut oil, liquid paraffin or olive oil is mixed.

The active ingredient can be tightly combined with a pharmaceutically acceptable carrier by conventional drug mixing techniques. The carrier may take a variety of forms depending on the form of the desired formulation administration. In the preparation of pharmaceutical compositions for oral dosage forms, any of the usual pharmaceutical media can be used as carriers, for example, water, glycols, oils, ethanol, flavoring agents, preservatives, colorants, and oral liquid preparations (e.g., liquids, solutions, and elixirs) or aerosols, or carriers such as starch, sugar, microcrystalline cellulose, diluents, granules, lubricants, binders, and disintegrants can be used in oral solid preparations. The lactose is not used in some embodiments. In some embodiments, the compound may be mixed with lactose, sucrose, starch powder, cellulose ester of alkanoic acid, cellulose alkyl ester, talc, stearic acid, magnesium stearate, magnesium oxide, calcium phosphate, sodium phosphate, calcium sulfate, sodium sulfate, gelatin, gum arabic, sodium alginate, polyvinylpyrrolidone and/or polyvinyl alcohol for further formulation. For example, the preparation of solid oral preparations, suitable carriers also include powders, capsules and tablets. In some embodiments, the tablet may be coated by standard aqueous or non-aqueous techniques.

Suitable for use in pharmaceutical compositions and dosage forms, including, but not limited to, corn starch, potato starch, or other starches, gelatin, natural binders and synthetic gums such as gum arabic, sodium alginate, alginic acid, other alginic acid salts, powdered tragacanth, guar gum, cellulose and derivatives thereof (e.g., ethylcellulose, cellulose acetate, carboxymethylcellulose calcium, sodium carboxymethyl cellulose), polyvinylpyrrolidone, cellulose, pregelatinized starch, hydroxypropylmethyl cellulose, microcrystalline cellulose, and mixtures thereof.

Examples of suitable fillers for use in pharmaceutical compositions and dosage forms include, but are not limited to, talc, calcium carbonate (e.g., granules or powders), microcrystalline cellulose, powdered cellulose, glucose binders, kaolin, mannitol, silicic acid, sorbitol, starch, pregelatinized starch, and mixtures thereof.

The disintegrant may be used in a pharmaceutical composition as provided herein to provide a tablet that disintegrates when exposed to a water environment. Too much disintegrant can cause the tablet to disintegrate in the bottle. Too little may not be sufficient to disintegrate, and thus can change the release rate and extent of the active ingredient of the dosage form. Thus, the disintegrant should be sufficient, neither too little nor too much to detrimentally release the active ingredient. The amount of disintegrant will depend on the formulation and mode of administration, and may be readily implemented by one of ordinary skill in the art. About 0.5 to about 15% by weight of a disintegrant, or about 1 to about 5% by weight of a disintegrant, may be used in a pharmaceutical composition. To form disintegrants and dosage forms for pharmaceutical compositions including, but not limited to, agar, alginic acid, calcium carbonate, microcrystalline cellulose, croscarmellose, crospovidone, sodium acetate, potato or tapioca starch, other starches, preformed starch, clay, other algae, other cellulose, gums or mixtures thereof.

Lubricants may be used to form pharmaceutical compositions including, but not limited to, calcium stearate, magnesium stearate, mineral oil, light mineral oil, glycerol, sorbitol, mannitol, polyethylene glycol, other diols, stearic acid, sodium lauryl sulfate, talc, hydrogenated vegetable oils (e.g., peanut oil, cottonseed oil, sunflower oil, sesame oil, olive oil, corn oil and soybean oil), zinc stearate, ethyl oleate, Ethyl laurate, agar or mixtures thereof. Lubricants also include, for example, silica gel, coagulated aerosols, or mixtures thereof. The lubricant may optionally be added in an amount of less than about 1% by weight of the pharmaceutical composition.

When aqueous suspensions and/or elixirs are used for oral administration, the active ingredient may be combined with various sweetening or flavoring agents, coloring agents or dyes, for example, emulsifiers and/or suspending agents, diluents, for example, water, ethanol, propylene glycol, glycerol, and combinations thereof.

Surfactants that may be used to form pharmaceutical compositions and dosage forms include, but are not limited to, hydrophilic surfactants, lipophilic surfactants, and mixtures thereof. Suitable hydrophilic surfactants may generally have an HLB value of at least about 10, and suitable lipophilic surfactants may generally have an HLB value of less than about 10. The empirical parameter used to characterize the relative hydrophilicity and hydrophobicity is the hydrophilic lipophilic balance value HLB ("HLB" value). The lower HLB value of the surfactant is more lipophilic or hydrophobic and has a greater solubility in the oil while the active agent with a higher HLB value is more hydrophilic and has a greater aqueous solution of the solubility. Hydrophilic surfactants are generally considered to be those having HLB values greater than about 10, however, anions, cations or zwitterionic compounds, HLB scales are generally not applicable. Similarly, lipophilic (i.e., hydrophobic) surfactants are those having an HLB value equal to or less than about 10. However, the HLB value of the surfactant is only a rough guide for general use in industrial, pharmaceutical and cosmetic emulsions.

The hydrophilic surfactant may be ionic or nonionic. Suitable ionic surfactants include, but are not limited to, alkylammonium salts; fusidic acid salts; fatty acid derivatives of amino acids, oligopeptides and polypeptides; derivatives of amino acids, oligopeptides and glycerol esters of polypeptides; lecithin and Phospholipid and its derivatives; carnitine fatty acid ester salts; alkyl sulphates; fatty acid salts; docetyl sodium; acyl lactic acid salts; mono- and diacetylated mono- and diglycerides of tartaric acid esters; succinylated mono- and diglycerides; citrate esters of mono- and di-glycerides; and mixtures thereof. Ionic surfactants include, but are not limited to, for example, lecithin, lysolecithin, phospholipids, lysophospholipids and derivatives thereof, carnitine fatty acid ester salts; alkyl sulfates; fatty acid salts; acyl lactylates; diacylated tartaric acid esters of mono- and mono- and di- and diglycerides; succinylated mono- and diglycerides; citrate esters of mono- and di-glycerides; and mixtures thereof. Hydrophilic nonionic surfactants include, but are not limited to, alkyl glycosides; alkyl maltose; alkyl thiosides; lauroyl polyglycol glycerides; polyoxyalkylene alkyl ethers such as polyethylene glycol polyoxyalkylene alkyl phenols, for example, polyethylene glycol alkylphenols; polyoxyalkylene alkylphenol fatty acid esters such as polyethylene glycol fatty acid monoester and polyethylene glycol fatty acid diester; diol glycerol fatty acid esters; polyglycerol fatty acid esters; polyoxyalkylene sorbitan fatty acid esters, for example, polyethylene glycol sorbitol fatty acid esters; and glycerol esters, vegetable oils, hydrogenated vegetable oils, fatty acids and sterols polyoxyethylene sterols, derivatives thereof, and the like; polyoxyethylenated vitamins and derivatives thereof, polyoxyethylene-polyoxypropylene block copolymers; and mixtures thereof, hydrophilic transesterification products of polyethylene glycol sorbitan fatty acid esters and polyols of at least one triglyceride, vegetable oil and hydrogenated vegetable oil. The polyol may be glycerol, ethylene glycol, polyethylene glycol, sorbitol, propylene glycol, pentaerythritol or carbohydrates. Other hydrophilic nonionic surfactants include, but are not limited to, PEG-10 lauric acid, PEG-12 lauric acid, PEG-20 lauric acid, PEG-32 lauric acid, PEG-32 dilaurate, PEG-12 oleate, PEG-15 oleate. PEG-20 oleate, PEG-20 dioleate, PEG-32 oleate, PEG-200 oleate, PEG-40 oleate, PEG-15 stearate, PEG-32 distear lactone, PEG-40 stearate, PEG-100 stearate, PEG-20 dilaurate, PEG-25 glycerol trioleate, PEG-32 dioleate, PEG-20 glyceryl laurel Lactone, PEG-30 glyceryl laurate, PEG-20 glyceate, PEG-20 glyceryl oleate, PEG-30 glycerol, PEG-30 glyce, PEG-40 castor oil, PEG-40 castor oil, PEG-40 castor oil, PEG-40 castor oil, PEG-40 castor oil, PEG-40 castor oil, PEG-40 castor oil, PEG-40 castor oil, PEG-40 castor oil, PEG-40 castor oil, PEG-Hydrogenated castor oil, PEG-60 corn oil, PEG-6 glyceryl/capric acid glyceride, PEG-8 caprate/capillate glyceride, polyglyce 1 to 10 laureate, PEG-30 cholesterol, PEG-25 plant sterol, PEG-30 soybean sterol, PEG-20 trioleate, PEG-40 sorbitol oleate, PEG-80 sorbitan laurate, polysorbate 20, polysorbate 80, POE-9 dodecyl ether, POE-23 lauryl ether, POE-10 oleyl ether, POE-20 oleyl ether, POE-20 stearin, PEG-100 tocopherol succinate, PEG-24 cholesterol, Tween 40, Tween 60, sucrose monostearate, sucrose monolaurate, sucrose monopalmitate, PEG 10-100 nonylphenol series, PEG 15-100 octylphenol series and poloxamer. Suitable lipophilic surfactants include, but are not limited to, for example, fatty alcohols; glycerol fatty acid esters; acetylated glycerol fatty acid esters; lower alcohol fatty acid esters; propylene glycol fatty acid esters; sorbitol fatty acid esters; diol sorbitan fatty acid esters; sterols and sterol derivatives; polyoxyethylenated sterols and sterol derivatives; polyethylene glycol alkyl ethers; sugar esters; sugar ethers; lactic acid derivatives of mono- and diglycerides.

The pharmaceutical composition may include a solubilizing agent to ensure good solubilization and/or dissolution of the compound and to minimize the precipitation of the compound. This may be particularly useful for non-oral use, for example, pharmaceutical compositions for pharmaceutical compositions for injection. The solubilizing agent may also be added to increase the solubility of the hydrophilic drug and/or other components, such as the surfactant, or the maintenance of the pharmaceutical composition as a stable or homogeneous solution or dispersion. Examples of suitable solubilizing agents include, but are not limited to, for example, alcohols and polyols such as ethanol, isopropanol, butanol, benzyl alcohol, ethylene glycol, propylene glycol, butylene glycol and isomers thereof, glycerol, pentaerythritol Sorbitol, mannitol, dimethyl isosorbide, polyethylene glycol, polypropylene glycol, polyvinyl alcohol, and other cellulose derivatives, cyclodextrins and cyclodextrin derivatives; ethers of polyethylene glycol, having a molecular weight of about 200 to about 6000, such as tetrahydrofurfuryl alcohol PEG ether (tetrahydrofuran polyglycol ether) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidine, N-alkyl caprolactam, dimethylacetamide and polyvinylpyrrolidone; esters such as ethyl propionate, ester, acetyl triethyl citrate, triethyl citrate, triethyl citrate, ethyl oleate, ethyl octanoate, ethyl butyrate, glycerol triacetate, propylene glycol monoacetate, propylene glycol diacetate, ε-caprolactone and their isomers, delta-valine esters and their isomers, butyrolactones and their isomers; and other known solubilizing agents such as dimethylacetamide, dimethylisosorbide, N-methylpyrrolidone, diethylene glycol monoethyl ether and water. Mixtures of solubilizers may also be used.

The amount of the given solubilizing agent may be limited to a biologically acceptable amount, which can be readily determined by one of skill in the art. The solubilizing agent may be in a weight ratio of about 10%, about 25%, about 50%, about 100%, or at most about 200% by weight, based on the total weight of the drug, and other excipients. A small amount of solubilizing agent may also be used, if desired, such as about 5%, 2%, 1% or less. Typically, the solubilizing agent may be present in about 1% to about 100%, typically from about 5% to about 25% by weight.

The pharmaceutical compositions described may also include one or more pharmaceutically acceptable additives and excipients, flavoring agents, coloring agents, suspending agents, binders, fillers, plasticizers, lubricants, and mixtures thereof. Preservatives may include, but are not limited to, for example, antioxidants, chelating agents, antimicrobial preservatives, antifungal preservatives, alcohol preservatives, acid preservatives and other preservatives. Antioxidants include, but are not limited to, alpha-tocopherol, ascorbic acid, butylated hydroxyanisole, butylhydroxytoluene, monothioglycerol, potassium pyrosulfite, propionic acid, propyl gallate, sodium ascorbate, sodium bisulfate, and sodium sulfite. Chelating agents include, but are not limited to, for example, ethylenediaminetetraacetic acid (EDTA), citrate monohydrate, disodium ethylenediamine tetraacetate, dipotassium ethylenediamine tetraacetate, edetic acid, fumaric acid, malic acid, phosphoric acid, sodium edetate, tartaric acid, and triethylenediamine tetraethyl citrate. Antimicrobial preservatives include, but are not limited to, for example, benzalkonium chloride, benzethonium chloride, benzyl alcohol, bromonitropylene glycol, cetrimonium bromide, cetylpyridinium chloride, chlorocresol, cresol, Ethanol, glycerol, heptacidine, imidazolidine, phenol, phenoxyethanol, phenylethyl alcohol, phenylmercuric nitrate, and propylene glycol. Antifungal agents include, but are not limited to, for example, butyl p-hydroxybenzoate, methyl p-hydroxybenzoate, ethyl p-hydroxybenzoate, propyl p-hydroxybenzoate, benzoic acid, hydroxybenzoic acid, potassium benzoate, potassium sorbate, sodium benzoate, sodium propionate and sorbic acid. Preservatives include, but are not limited to, for example, ethanol, polyethylene glycol, phenol, phenol compounds, bisphenols, chlorobutanol, hydroxybenzoate, and phenylethanol. Acid preservatives include, but are not limited to, for example, vitamin A, vitamin C, vitamin E, beta-carotene, citric acid, acetic acid, dehydroacetic acid, ascorbic acid, sorbic acid and phytic acid. Other preservatives include, but are not limited to, for example, tocopherol acetate, cetrimonium bromide, butylated hydroxyanisole (BHA), butylhydroxytoluene (BHT), ethylenediamine, sodium lauryl sulfate (SLS), Sodium lauryl ether sulfate (SLES), sodium bisulfate, sodium metabisulfite, potassium sulfite, potassium pyrosulfite, methyl p-hydroxybenzoate. In certain embodiments, the preservative may be an antioxidant. In other embodiments, the preservative may be a chelating agent.

In some embodiments, provided herein are pharmaceutical compositions for parenteral administration: (1) an effective amount of a disclosed compound; optionally (2) an effective amount of one or more second reagent; (3) one or more pharmaceutical excipients suitable for parenteral administration and (4) an effective amount of a third reagent.

Wherein the pharmaceutical composition may be administered in the form of an aqueous or oily suspension, or an emulsion, sesame oil, corn oil, cottonseed oil, or peanut oil, and elixirs, mannitol, dextrose, or sterile aqueous solutions, similar drug carrier. Aqueous saline solution is also commonly used for injection. Ethanol, glycerol, propylene glycol, liquid polyethylene glycol, benzyl alcohol, etc. (and mixtures thereof suitable), cyclodextrin derivatives, sodium chloride, tragacanth, buffers, and vegetable oils may also be used. Proper fluidity can be maintained by using a coating, for example, lecithin, or in the case of a dispersion, by maintaining the desired particle size using a surfactant. The prevention of microbial action can be achieved by various antibacterial and antifungal agents, for example, p-hydroxybenzoic acid esters, chlorobutanol, phenol, sorbic acid, thimerosal and the like. The pharmaceutical compositions may also be injected by suitable carriers, including saline, glucose or water, or solubilized with cyclodextrins, co-solvents (e.g., propylene glycol) or micelles (e.g., Tween 80).

The sterile injectable solution may be prepared by filtration and sterilization by the desired amount of the compound disclosed herein with a suitable solvent for the various other ingredients described above. Typically, the dispersion is prepared by incorporating the various sterilized active ingredients into a sterile carrier containing the basal dispersion medium and the appropriate other components listed above. A sterile injectable solution is prepared with a sterile powder, and some of the methods of preparation are carried out by vacuum drying and freeze-drying techniques to produce the active ingredient and any other sterile filtered ingredients described above. The sterile injectable preparation may also be prepared by a solution of a non-toxic parenterally acceptable diluent or solvent, for example, a solution in 1,3-butanediol or a sterile injectable solution. Acceptable carriers and solvents that may be used include, but are not limited to, for example, water, Ringer's solution and isotonic sodium chloride solution. In addition, sterile, non-volatile oils are commonly used as solvents or suspending media, including, but not limited to, for example, synthetic mono- or diglycerides. In addition, fatty acids, for example, oleic acid, can also be used in the preparation of injections. The injectable preparation may be sterilized by, for example, a bacterial retention filter, or by adding a sterilizing agent incorporated into a sterile solid composition which may be dissolved or dispersed in sterile water or other sterile injectable medium. The injectable composition may be present in about 0.1 to about 5% by weight of the compounds disclosed herein.

In some embodiments, provided herein are compounds (or transdermal) containing pharmaceutical preparations containing one or more pharmaceutical excipients, such as those disclosed herein, suitable for topical administration. In some embodiments, there is provided a drug-containing composition for topical administration: (1) an effective amount of a disclosed compound; optionally (2) an effective amount of one or more second agents; (3) one or more pharmaceutical excipients suitable for topical administration and (4) an effective amount of a third agent.

The pharmaceutical compositions provided herein may be formulated in a solid, semi-solid or liquid form suitable for local or topical application such as gelling agents, water-soluble gels, liniments, creams, lotions, suspensions, foams, powders, ointments, ointments, solutions, oils, pastes, suppositories, sprays, emulsions, saline solutions, dimethylsulfoxide (DMSO) based solutions. In general, a carrier having a higher density can provide a region having a long-term exposure to the active ingredient. In contrast, the solution formulation may provide a more direct contact of the region selected by the active ingredient. For example, the ointment formulation may have paraffin or water miscibility. Alternatively, the active ingredient may be formulated as a cream with the cream base of the oil in water. The aqueous phase of the cream matrix may comprise, for example, at least about 30% by weight of polyols such as propylene glycol, butane-1,3-diol, mannitol, sorbitol, glycerol, polyethylene glycol and mixtures thereof. The pharmaceutical compositions described above may also contain suitable solid or gel phase carriers or excipients that may increase penetration or assist in delivery of the compound through the skin barrier layer of the stratum corneum. Examples, such as, urea (e.g., urea), (e.g., menthol), amines, amides, alkanes, alkanols, water, and the like, such as isopropyl myristate and sodium sulphate, pyrrolidone, glycerol monolaurate, sulfoxide, calcium carbonate, calcium phosphate, various sugars, starches, cellulose derivatives, gelatin and polymers such as polyethylene glycol.

Another exemplary formulation used in the disclosed method uses transdermal administration ("patch"). Such transdermal patches can be used to provide a controlled or discontinuous pharmaceutical composition in a continuous or discontinuous manner. If the active agent is absorbed by the skin, the controlled and scheduled flow of the active agent can be administered to the subject. In the case of microcapsules, the encapsulant may also be used as a film. The use of transdermal patches is well known in the art. See, for example, U.S. Pat. Nos. 5,023,252, 4,992,445 and 5,001,139.

The pharmaceutical compositions of the present invention may be administered in the form of suppositories for rectal administration. These compositions may be prepared by mixing the compounds of the present invention with a suitable non-irritating excipient which is solid at room temperature but is liquid at the rectal temperature and will melt in the rectum to release active ingredient. Such materials include, but are not limited to, for example, polyethylene glycol, beeswax and cocoa butter.

The pharmaceutical compositions of the present invention may be administered by nasal aerosols or inhalants. Such a composition is prepared according to techniques known in the pharmaceutical preparation art and can be prepared as a solution of brine and can be used with benzyl alcohol or other suitable preservatives to increase the bioavailability of absorption enhancers, fluorocarbons, and other solubilizing or dispersing agents known in the art.

The application of the subject therapeutic agent may be localized to be administered at the target site. Various techniques may be used to provide a host composition at a target site, such as injection, use of a catheter, gel, stent, trocar, propellant, drug release polymer, or other device for providing internal access.

According to another embodiment, the present invention provides an implantable medical device comprising a compound of the invention or a composition comprising a compound of the invention such that the compound is a therapeutically active.

According to another embodiment, the present invention provides a method of injecting an implantable drug delivery device comprising the step of contacting said drug delivery device with a compound or composition of the invention. Implantable drug delivery devices include, but are not limited to, biodegradable polymeric capsules or pills, non-degradable, dispersible polymer capsules and biodegradable polymer flakes.

In another embodiment, the compositions of the present invention further comprise a second therapeutic agent. The second therapeutic agent includes any compound or therapeutic agent which, when administered alone or in combination with any of the compounds of the general formula herein, is known to have or is of a favorable nature. Drugs that may be usefully combined with these compounds include other kinase inhibitors and/or other chemotherapeutic agents for the treatment of diseases and disorders discussed above. Such agents are described in detail in the art. Preferably, the second therapeutic agent is an agent that can be used for the treatment or prophylaxis of a disease or condition selected from cancer via DNA double breaks mechanism.

In another embodiment, the present invention provides an independent dosage form of a compound of the invention and a second therapeutic agent associated with each other. As used herein, the term "associated with each other" means that the individual dosage forms are packaged together or otherwise connected to each other so that the individual dosage forms are expected to be sold or administered together (less than 24 hours Inside, continuously or simultaneously).

In the pharmaceutical compositions of the present invention, the compounds of the present invention are present in an effective amount. As used herein, the term "effective amount" refers to the severity, duration, or development of a disorder that is sufficient to reduce or ameliorate the disorder to be treated when administered with a suitable dosing regimen, to prevent progression of the disorder, the disruption of the treatment disorder, or the enhancement or improvement of the prophylactic or therapeutic effect of another therapy.

The effective amount of the compound of the present invention may range from about 0.001 to 1 mg/kg to about 500 mg/kg, from about 0.01 mg/kg to about 50 mg/kg, from about 0.1 mg/kg to about 2.5 mg/kg. Effective dosages may also vary, as will be appreciated by those skilled in the art, depending on the disease being treated, the severity of the disease, the route of administration, the age, sex and general health of the patient, excipient usage, and other treatments method for common use (e.g., the use of other agents), and the judgment of the treatment physician.

For a pharmaceutical composition comprising a second therapeutic agent, the effective amount of the second therapeutic agent is between about 20% and 100% of the dose normally used in a single treatment regimen using only the agent. Preferably, the effective amount is between about 70% and 100% of the normal single therapeutic dose.

It is expected that some of the second therapeutic agents mentioned herein will act synergistically with the compounds of the present invention. When present, it will allow the effective dose of the second therapeutic agent and/or the compound of the invention to be less than the dosage required for single therapy. This has the advantage that the secondary side effects of the second therapeutic agent or the compound of the present invention are minimized, improved efficacy, improved ease of administration or use, and/or reduced overall cost of the compound preparation or formulation.

The treatment is as follows:

According to another embodiment, the present invention provides a method of treating a subject suffering from or susceptible to a disease or disorder or a symptom thereof (e.g., those described herein) comprising administering to said subject an effective amount of the inventive compounds or compositions are administered in a step. These diseases are well known in the art and are also disclosed herein.

The treatment involves the treatment of disorders mediated by protein kinases such as ATM.

In another aspect, the present invention provides a method of treating a disease in a subject comprising administering to a subject a composition comprising any compound of the general formula herein.

In certain embodiments, the disease is mediated by an ATM kinase.

In another embodiment, the disease is a cancer or a proliferative disease.

In another embodiment, as an inhibitor against the activating ATM, the compound of formula (I), and the pharmaceutically acceptable salt, is expected to be present in the activity of the ATM or partially mediated, such as the treatment of cancer or medical conditions. This may use the type of cancer treated with the compound of formula (I), or a pharmaceutically acceptable salt, including, but not limited to, ovarian cancer, cervical cancer, colorectal cancer, breast cancer, pancreatic cancer, glioma, glioblastoma, thymoma, melanoma, prostate cancer, leukemia, lymphoma, non-Hodgkin's lymphoma, gastric cancer, lung cancer, liver cancer, bone cancer, gastrointestinal stromal tumors (GIST), thyroid cancer, cholangiocarcinoma, uterus Endometrial cancer, renal cell carcinoma, anaplastic large cell lymphoma, acute myeloid leukemia (AML), multiple myeloma, melanoma, mesothelioma, brain cancer, adenocarcinoma, DIPG, skin cancer or head and neck squamous cell carcinoma.

In another embodiment, the disease is cancer resistant to treatment with radiation.

In another embodiment, the disease is cancer resistant to treatment with agent causing DNA double strand breaks.

In another embodiment, the disease is cancer with central nervous system metastases.

In another embodiment, the disease is glioma.

In another embodiment, the disease is glioblastoma.

In another embodiment, the disease is a diffuse intrinsic pontine glioma.

In one embodiment, the method of the invention is used to treat a subject suffering from or susceptible to a disease or condition. These diseases, disorders or their symptoms include, for example, those regulated by protein kinases (e.g., ATM protein kinases). The disease or disease symptoms may be, for example, cancer or proliferative diseases or disorders. The disease or disease symptoms may be ovarian cancer, cervical cancer, colorectal cancer, breast cancer, pancreatic cancer, glioma, glioblastoma, diffuse intrinsic pontine glioma, melanoma, prostate cancer, leukemia, lymphoma (GIST), thyroid cancer, cholangiocarcinoma, endometrial cancer, kidney cancer, anaplastic large cell lymphoma, acute myeloid leukemia (GIST), gastric cancer, lung cancer, liver cancer, AML), multiple myeloma, melanoma, mesothelioma, brain cancer, membranous adenocarcinoma, skin cancer or squamous cell carcinoma of the head and neck. The methods described herein include those subjects in which the subject is identified as requiring treatment that is specifically described. The identification of the subject requires that the treatment be within the judgment of the subject or health care specialist and may be subjective (e.g., opinion) or objective (e.g., measurable by test or diagnostic method).

In another embodiment, the compounds of the general formula (and compositions thereof) herein are useful for the treatment of diseases or disorders that have been treated with other therapeutic agents (e.g., anticancer agents, neurotrophic agents, psychotropic agents, a cardiovascular disease agent, an anti-obesity or diabetes agent) and to form a resistant subject. In one aspect, the methods herein include administering to a subject in which treatment is resistant (or identified as having resistance to treatment with radiation or chemotherapy causing DNA double strand breaks) in which the compound of formula (or its composition) of those methods. In other aspects, the subject is therefore responsive to the treatment, so that the disorder is regulated or improved prior to treatment with the compound of the present formula.

In another embodiment, the present invention provides a method of modulating the activity of a protein kinase in a cell (e.g., a protein kinase, a kinase as enumerated herein) comprising contacting the cell with one or more compounds of the general formula herein contact.

The anti-cancer treatment described above can be administered as a monotherapy or with conventional compounds or radiotherapy or chemotherapy or immunotherapy with the compounds of the present invention. Such chemotherapy may be co-administered, simultaneously, sequentially or separately, with the compounds of the present invention and may include, but are not limited to, one or more of the following categories of antineoplastic agents: for example, antiproliferative/antineoplastic agents, alkylation (e.g., cisplatin, oxaliplatin, carboplatin, cyclophosphamide, nitrogen mustard, melphalan, chlorambucil, busulfan, temozolomide and nitrosourea), antimetabolites (e.g., gemcitabine and antifungal acids such as 5-fluorouracil and tegafur, raltitrexed, methotrexate, cytarabine, and hydroxyurea); antitumor antibiotics (e.g., anthracycline drugs such as doxorubicin, bleomycin, adriamycin, daunorubicin, epirubicin, idarubicin, mitomycin C, gentamicin and gliramycin); antimitotic agents (e.g., vinca alkaloids such as vincristine, alkaloids such as paclitaxel and tacrolimus and polokinase inhibitors); and topoisomerase inhibitors (e.g., epipodophyllotoxin etoposide and dipyridine) glycosides, an acridine, topotecan and camptothecin); cell growth inhibitors such as anti-Hormones (e.g., tamoxifen, fulvestrant, toremifene, raloxifene, droloxifene and zifoxifene), antiandrogens (e.g., amylamine, flutamide, nilutamide acetate and cyclopropanone), LHRH antagonists or LHRH agonists (e.g., goserelin, leuprolide and bucorin, progesterone (e.g., megestrol acetate, Aromatase inhibitors (e.g., anastrozole, letrozole, buoxazole, and exemestane) and inhibitors of 5a reductase such as finasteride; anti-invasive agents (e.g., c-Src kinase family inhibition agents such as cetatinib; dasatinib and bosutinib and bosutiphene, and inhibitors of metalloproteinases such as equine, inhibitors of urokinase plasminogen activator receptor or antibody heparinase. Inhibitors of growth factor function: for example, such inhibitors include growth factor antibodies and growth factor receptor antibodies (e.g., anti-erbB2 antibody trastuzumab [Herceptin™], anti-EGFR antibody panitumumab, anti-ErbB antibody cetuximab (erbatide, C225) and by Stem et al. Critical reviews in oncology/haematology disclosed a growth factor receptor or a growth factor receptor antibody, 2005, Vol. 54, 11-29. Such inhibitors also include tyrosine kinase inhibitors such as epidermal growth factor family inhibitors (e.g., EGFR family inhibitors such as gefitinib, erlotinib, icotinib, afatinib, dacomitinib and Tagrisso, erbB2 tyrosine kinase inhibitors, such as lapatinib, neratinib); hepatocyte growth factor family Inhibitors; the platelet-derived growth factor family such as imatinib and/or nilotinib; inhibitors of serine/threonine kinases (e.g., RAS/RAF signaling Inhibitors such as feniyltransferase inhibitors such as sorafenib, tipifanib and lonafanib, by MEK and/or AKT kinase cell signaling inhibitors, c-kit inhibitors, abl fusion kinase inhibitors, PI3 kinase inhibitors, PLT3 kinase inhibitors, CSF-1R kinase inhibitors, IGF receptors (insulin-like growth factor) kinase inhibitors; aurora kinase inhibitors and cyclin-dependent kinase inhibitors such as CDK2 and/or CDK4 inhibitors; antiangiogenic agent, such as those that inhibit the effects of vascular endothelial growth factors, antibodies bevacizumab (Avastin™) and, for example, VEGF receptor tyrosine kinase inhibitors such as vandetanib, vatalanib, sunitinib, axitinib, cabozantinib, pazopanib and cediranib, compounds that work through other mechanisms (e.g., tricarboxyaminoquinoline, integrin αV3 functional inhibitors and angiogenesis inhibitors); antisense (nucleic acid) therapy, including, for example, the replacement of abnormal genes such as abnormal p53 or aberrant BRCA1 or BRCA2, as described above, such as ISIS 2503, anti-ras gene antisense (nucleic acid) (e.g., Olaparib, Niraparib, Rucaparib, Talazoparib), GDEPT (gene-directed prodrug therapy) methods such as enzymes using cytosine deaminase, thymidine kinase or bacterial nitro reductase, and those that increase patient resistant chemotherapeutic or radiotherapy such as multi-drug resistance gene therapy immunotherapy, including, for example, increasing the immunogenicity of tumor cells of a patient, e.g., using cytokines such as interleukin 2, 4 or granulocyte-macrophage stimulating factor transfection of the immunogenicity of the T cells to reduce the non-responsiveness of the method using transfected immune cells such as cytokine transfected dendritic cells, cytokine transfection anti-idiotypic antibody to reduce the function of immunosuppressive cells such as regulatory T cells, medullary inhibitory cells or IDO, TDO, and the use of antibodies derived from tumor-associated antigens such as NY-ES0-1, MAGE-3, WTI or HER2/neu derived protein or peptide or any other agent (e.g., antiemetic agent, anti-anemia agent, etc.) that is generally used as a base agent or adjuvant in a cancer treatment regimen.

As used herein, the term "co-administered" means that the second therapeutic agent may be administered in combination with a compound of the invention as a single dosage form (e.g., a composition comprising a compound of the invention and a second therapeutic agent as described above) in part or as an independent, multi-dose form. Alternatively, additional reagents may be administered prior to, or in connection with, or after the administration of the compounds of the invention. In such combination therapy, the compounds of the present invention and the second therapeutic agents are administered by conventional methods. The administration of the compositions of the invention comprising the compounds of the invention and the second therapeutic agent to the subject does not exclude the same therapeutic agent, any other second therapeutic agent or any of the compounds of the invention at other times during the course of treatment Independent administration of the subject. Wherein the continuous or separate administration, or delaying administration of the second component, should not lose the advantage of the effect produced from the use of the combination.

In one embodiment of the invention, when the second therapeutic agent is administered to the subject, the effective amount of the compound of the invention is lower than the effective amount of the second therapeutic agent when no second therapeutic agent is administered. In another embodiment, the effective amount of the second therapeutic agent is less than the effective amount of the second therapeutic agent when the compound of the invention is not administered. In this way, undesirable side effects associated with any of the high doses of the agent can be minimized. The potential advantages for those skilled in the art will be apparent (including, but not limited to, for example, improving the dosing regimen and/or reducing the cost of the drug).

In another aspect, the invention provides the use of any of the compounds of the general formula herein, either alone or in combination with one or more of the second therapeutic agents described herein, in the manufacture of a medicament as a single composition or as a separate dosage form, a medicament for the treatment or prevention of a disease, disorder or symptom listed herein in a subject. Another aspect of the invention is the use of a compound of the general formula herein for the treatment or prevention of a disease, disorder or symptom described herein in a subject.

In other aspects, the methods herein include further comprising those methods of monitoring the response of the subject to therapeutic administration. Such monitoring may include periodic sampling of subject tissue, body fluids, cerebrospinal fluid, samples, cells, proteins, chemical markers, genetic material, etc. as a marker or indicator of a therapeutic regimen. In other methods, by assessing the adaptability of the relevant marker or indicator to such treatment, the subject is pre-screened or identified as requiring such treatment.

In one embodiment, the present invention provides a method of monitoring the progression of therapy. The method comprises determining a diagnostic marker (marker) in a subject suffering from or susceptible to disorders or symptoms described herein (e.g., any target or cell type described herein regulated by the compounds herein) or diagnosed (e.g., screening, assay), wherein the subject has been administered a compound of the present invention sufficient to treat the therapeutic amount of the disease or its symptoms. The level of the marker determined in the method may be compared to a well-known level in a healthy normal control or other diseased patient to establish a disease condition of the subject. In a preferred embodiment, the second level of the marker in the subject is measured at a time point later than the first level of measurement and the two levels are compared to monitor the efficacy of the progression or therapy of the disease. In certain preferred embodiments, the level of the marker prior to treatment in the subject is measured prior to initiation of treatment according to the present invention; the pre-treatment level of the marker may be the same as the marker in the subject after treatment initiation Level to determine the effectiveness of treatment.

In certain method embodiments, the level of marker or marker activity in the subject is determined at least once. The marker level is compared with another measured value, for example, from the same patient, another patient, or another subject that was previously or subsequently acquired by the subject, to determine whether the therapy according to the present invention has the desired effect, and thus allow the dose level to be adjusted as appropriate. The determination of the level of the marker can be carried out using any suitable sampling/expression assay method known in the art or described herein. Preferably, the tissue or liquid sample is first removed from the subject. Examples of suitable samples include blood, urine, cerebrospinal fluid, tissue, mouth or buccal cells, and hair samples containing roots. Other suitable samples are known to those skilled in the art.

The determination of protein levels, ctDNA, cfDNA and/or mRNA levels (e.g., marker levels) in the sample can take advantage of any suitable technique known in the art including, but not limited to, enzyme immunoassays, ELISA, radioactive labeling techniques, western blot/chemiluminescence, real-time PCR, electrochemical signals, and the like.

The present invention also provides a kit for the treatment of diseases, disorders or symptoms of those described herein. Such kits include: 1) a pharmaceutical composition comprising any of the compounds of the general formula herein or salts thereof; or a salt thereof; or a pharmaceutical composition of a hydrate, solvate or polymorph thereof, in a container; and 2) describes a description of the use of the pharmaceutical composition for the treatment of a method comprising a disease, disorder or symptom described herein. The container may be any container or other sealed or sealable device capable of containing the pharmaceutical composition. Examples include a bottle, a separate or multi-chamber reservoir bottle, wherein each partition or compartment comprises a single dose of the composition; a separated foil package, wherein each partition comprises a single dose of the composition, which dispenses a single dose of said composition. The container may be any conventional shape or form known in the art and is made of a pharmaceutically acceptable material such as paper or cardboard boxes, glass or plastic bottles or cans, resealable bags (e.g., The "refill" of the tablet is used to be placed in a different container), or a single dose of blister pack is used to extrude the package from the treatment schedule. The containers used may depend on the exact dosage form involved, for example, conventional cardboard boxes will generally not be used to contain liquid suspensions. It is possible that more than one container can be used together in a single package to market a single dosage form. For example, the tablet may be contained in a bottle, which is then accommodated in the box. Preferably, the container is a blister pack.

The kit may additionally include information and/or instructions from a physician, pharmacist or subject. These memory aids include numbers printed on each compartment or partition containing the agent, which corresponds to the number of days the program or capsule should be ingested, or printed on each compartment or partition week number of days, or cards containing the same type of information.

Compounds described herein can be evaluated using their known regimens, including, for example, those described herein, to evaluate their biological activity. Some of the compounds described herein demonstrate surprisingly superior properties (e.g., metabolic stability, high selectivity, low efflux rate, high permeability, non-P glycoprotein and BCRP efflux substrate, non aldehyde oxidase substrate, low hERG liability, low drug-drug interaction liability etc.), making them excellent for potential therapeutic agents candidate.

All references cited herein, whether electronic, printed, computer-readable, or otherwise, are expressly incorporated herein by reference in their entirety, including, but not limited to, abstracts, articles, journals, publications, textbooks, papers, technical data sheets, internet sites, databases, patents, patent applications, and patent publications.

The present invention will now be described in detail with reference to the following examples. The following examples will aid the person skilled in the art in further understanding the present invention without limiting the invention in any way. It should be noted that many modifications and improvements may be made by those skilled in the art without departing from the spirit of the invention. All of which are within the scope of the present invention.

Example 1

Figure 2:
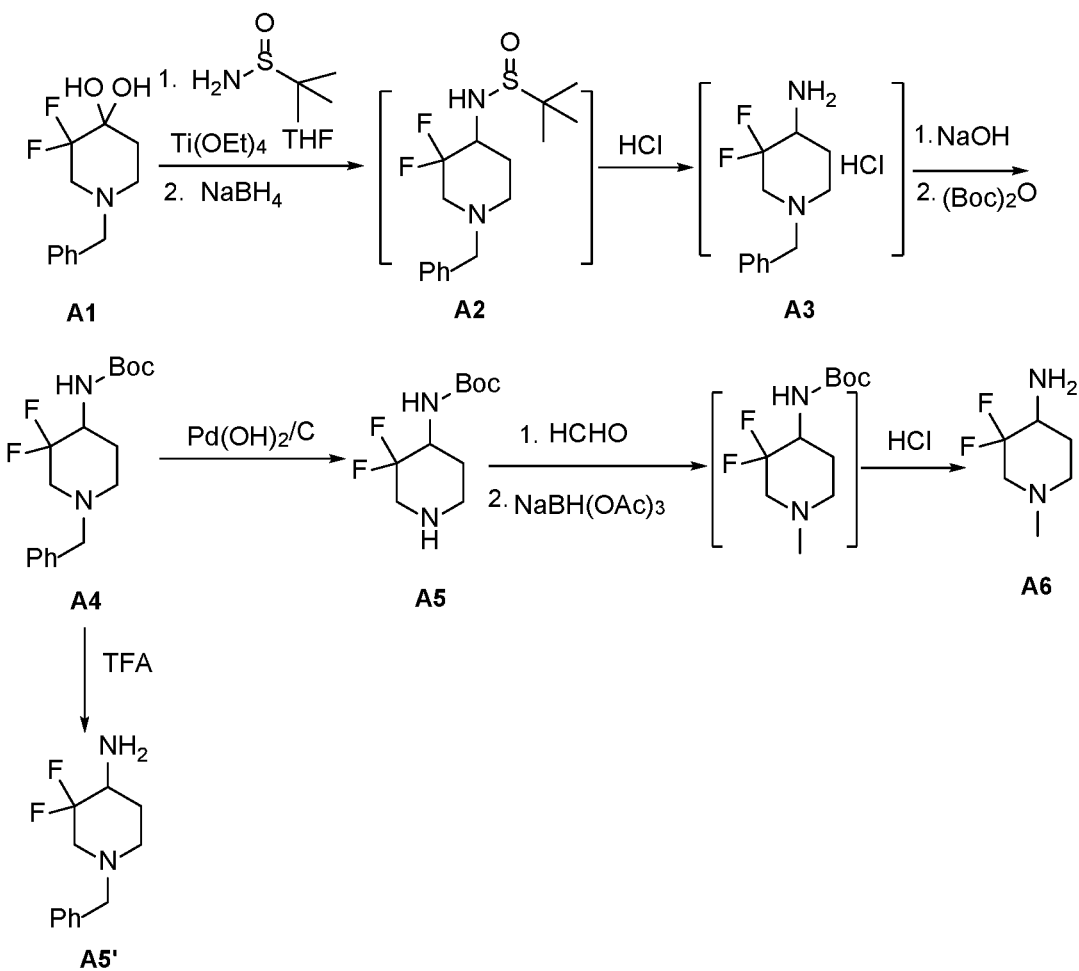
FIG. 2 illustrates the chemistry and synthesis of 3,3-difluoro-1-methylpiperidin-4-amine A6 and 1-benzyl-3,3-difluoropiperidin-4-amine A5'

Intermediate 3,3-difluoro-1-methylpiperidin-4-amine A6 and 1-benzyl-3,3-difluoropiperidin-4-amine A5' were synthesized shown in FIG. 2.

Step 1: To a solution of 2-methylpropane-2-sulfinamide (404 g, 3.33 mol) and Ti(OEt)$_4$ (1003 g, 4.44 mol) in THF (2.5 L) at 25° C. was added dropwise to a solution of A1 (500 g, 2.22 mol). The reaction mixture was stirred at 70° C. for 1 hour and then cooled to 0° C. The reaction mixture was then charged into NaBH$_4$ (166 g, 2.0 eq.) in THF (2.5 L) in another reactor at 0° C. The reaction mixture was stirred for 0.5 h at 0° C., then slowly warmed to 25° C. and continued to stir for 0.5 h. Methanol (2.5 L) was added and then stirred for 0.5 h. The mixture was added into a container containing saturated solution of NaCl (2.5 L) and stirred for 1 h at 25° C. The reaction mixture was extracted with DCM (2.5 L) twice. The organic layer was dried over anhydrous sodium sulfate, filtered and evaporated in vacuo to give product A2.

Step 2: A solution of crude A2 in ethyl acetate (1 L) at 25° C. was added HCl (5.0 eq, 4M in ethyl acetate), stirred for 1 h at 25° C. and then filtered to give A3.

Step 3: The filter cake A3 was added water (1.5 L) and then adjusted pH to 8-9 with 20% aq. NaOH solution at 25° C. The mixture was extracted with DCM (1.5 L) and the organic layer was dried over anhydrous sodium sulfate, filtered and concentrated. The crude was added triethylamine (267 g, 1.2 eq), followed by (Boc)$_2$O (577 g, 1.2 eq) and the mixture was stirred at 25° C. for 1 h. 10% citric acid solution (2 L) was added into the mixture, and then the organic layer was separated. The aqueous layer was extracted with DCM (1 L). The combined organic phases were dried over anhydrous sodium sulfate, filtered and concentrated to give A4 (430 g, 59.4%).

Step 4: To a solution of A2 ((380 g, 1.0 eq)) in MeOH (3.8 L) was added Pd(OH)$_2$/C (20%, w/w), the mixture was stirred for at least 1 h at 25° C. under 20 atm. The mixture was filtered and the filtrate was concentrated to give A5 (250 g, 91%).

Step 4': A mixture of A4 (4 g, 12.27 mmol) in TFA (20 mL) was stirred at room temperature for 2 hours. The mixture was concentrated in vacuo. The residue was further purified by column chromatography (DCM:MeOH=12:1) to give the compound A5' (2 g, 74.1%) as a yellow oil.

Step 5: To a solution of A5 (236 g, 1.0 eq) in MeOH (2.4 L) at 5° C. was added HCHO (37% in water, w/w). The reaction mixture was stirred at 5° C. for 1 h and then added NaBH(OAc)$_3$ portionwise until LC-MS indicated the disappearance of A5. The reaction mixture was added 10% aq. NaOH solution to adjust pH to 8-9 at 25° C. and stirred for 0.5 h at 25° C. The methanol was evaporated in vacuo and then the residue was extracted with ethyl acetate (1.2 L). The organic layer was separated and concentrated. HCl (5.0 eq, 4M in ethyl acetate) was added and then filtered. The filter cake was collected and dried at 45° C. under vacuo to give the HCl salt of A6 (125.1 g, 53.7%).

Figure 3:
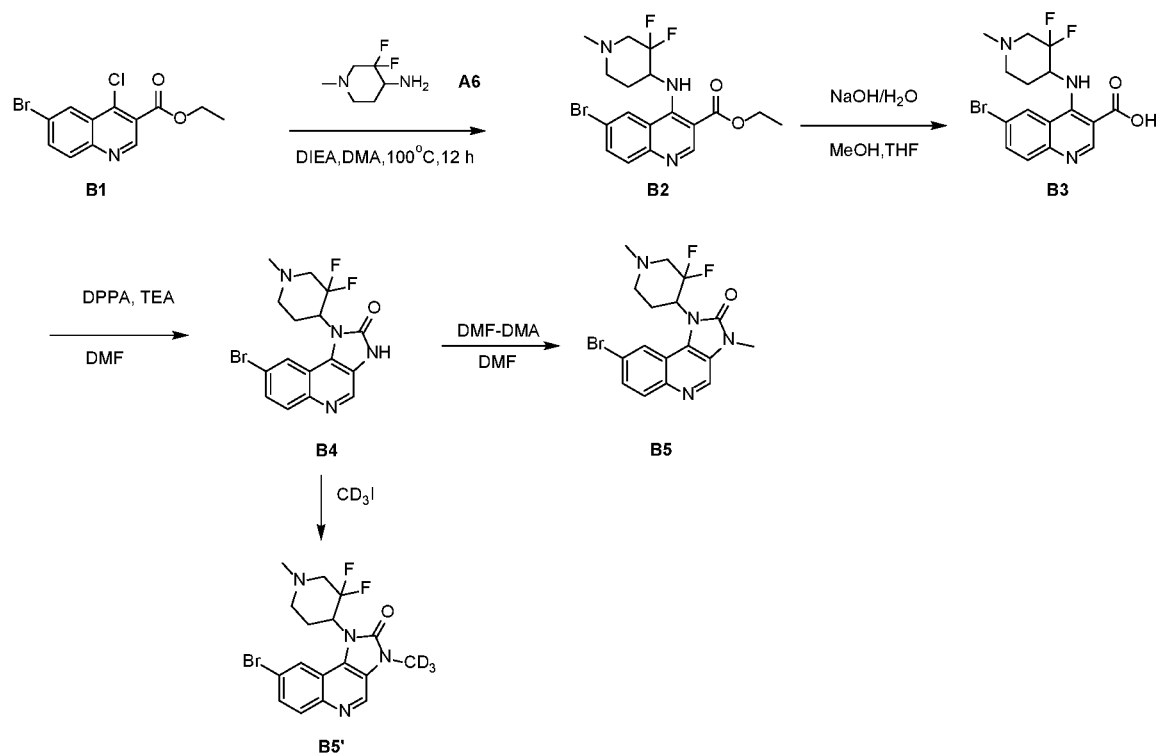
FIG. 3 illustrates the chemistry and synthesis of 8-bromo-1-(3,3-difluoro-1-methylpiperidin-4-yl)-3-methyl-1,3-dihydro-2H-imidazo[4,5-c]quinolin-2-one B5 and 8-bromo-1-(3,3-difluoro-1-methylpiperidin-4-yl)-3-(methyl-d3)-1,3-dihydro-2H-imidazo[4,5-c]quinolin-2-one B5'

Intermediate 8-bromo-1-(3,3-difluoro-1-methylpiperidin-4-yl)-3-methyl-1,3-dihydro-2H-imidazo[4,5-c]quinolin-2-one B5 and 8-bromo-1-(3,3-difluoro-1-methylpiperidin-4-yl)-3-(methyl-d3)-1,3-dihydro-2H-imidazo[4,5-c]quinolin-2-one B5' were synthesized shown in FIG. 3.

Step 1: A mixture of B1 (25 g, 79.48 mmol) in DMA (500 mL) was added 2 (14.92 g, 99.34 mmol) and DIEA (30 g, 238.744 mmol). The mixture was heated to 60° C. for 5 h.

The mixture was cooled to room temperature and poured into a mixture of DCM (500 mL) and H$_2$O (250 mL), the organic layer was separated and washed with brine, dried over anhydrous Na$_2$SO$_4$, filtered, concentrated in vacuo to give B2 (15 g, 44.09%) as an off-white solid. LC-MS: (ESI) m/z=404[M+H]$^+$ Step 2: A mixture of B2 (15 g, 33.35 mmol) in MeOH/H$_2$O/THF (300 mL/150 mL/150 mL) was added NaOH (8 g, 100 mmol) at room temperature and heated to 50° C. for 2 h. The mixture was cooled to room temperature, concentrated in vacuo to remove organic layer. The residue was added to H$_2$O (150 mL), adjusted to pH=4 by addition of 10% HCl, filtered to give B3 (11 g, 78.57%) as an off-white solid. $^1$H NMR (400 MHz, DMSO-d$_6$) δ 12-11.85 (m, 1H), 8.80-8.65 (m, 1H), 8.01-7.67 (m, 2H), 5.35-5.01 (m, 1H), 3.68-3.51 (m, 1H), 3.30-3.22 (m, 1H), 3.17 (d, J=8.0 Hz, 1H), 2.92 (d, J=12.0 Hz, 1H), 2.63-2.53 (m, 1H), 2.47-2.29 (m, 4H), 2.07-1.92 (m, 1H).

Step 3: To a solution of B3 (11 g, 27.5 mmol) and DPPA (7.12 mL, 33 mmol) in DMF (350 mL) was added TEA (28.2 mL, 82.5 mmol). The mixture was stirred at 60° C. for 2 h. The reaction was cooled to room temperature and then poured into H$_2$O (500 mL). The precipitate was filtered, washed with H$_2$O (50 mL), the filtered cake was dried to give B4 (10 g, 91.82%) as a brown solid.

Figure 4:
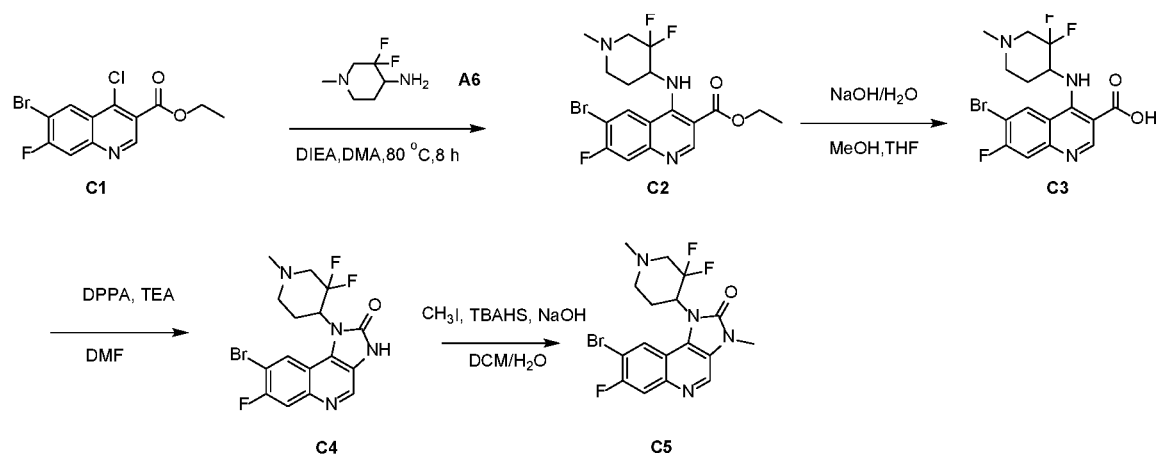
FIG. 4 illustrates the chemistry and synthesis of 8-bromo-1-(3,3-difluoro-1-methylpiperidin-4-yl)-7-fluoro-3-methyl-1,3-dihydro-2H-imidazo[4,5-c]quinolin-2-one C5

Step 4: To a mixture of B4 (10 g, 25.2 mmol) in DMF (250 mL) was added DMF-DMA (15.15 g, 126 mmol) at room temperature. After that the mixture was heated to 80° C. for 2 h, the mixture was cooled to room temperature, filtered. The filtrate was washed was H$_2$O, dried to give B5 (9 g, 86.95%) as an off-white solid. $^1$H NMR (400 MHz, DMSO-d) δ 9.05-8.95 (m, 1H), 8.75-8.36 (m, 1H), 8.04-7.71 (m, 2H), 5.37-5.16 (m, 1H), 3.67-3.55 (m, 1H), 3.50 (s, 2H), 3.30-3.23 (m, 1H), 2.93 (d, J=8.0 Hz, 1H), 2.74-2.53 (m, 1H), 2.48-2.32 (m, 4H), 2.07-1.93 (m, 1H). LC-MS: (ESI) m/z=411, 413 [M+H]$^+$ Step 4': A solution of B4 (400 mg, 1.01 mmol) in THF (20 mL) was cooled at −78° C., NaHMDS (221 mg, 1.21 mmol, 1M in THE solution) was added into the mixture and stirred at −78° C. for 30 min. Then CD$_3$I (87 mg, 1.21 mmol) was added dropwise into the mixture. The reaction mixture was stirred at room temperature for 16 hours. The mixture was added H$_2$O (10 mL), extracted with EtOAc (30 mL×3), then the organic layer was washed with brine, dried over anhydrous Na$_2$SO$_4$, filtered and concentrated in vacuo. The residue was purified by column chromatography (DCM:MeOH=30:1) to give the compound B5' (380 mg, 91.9%) as a yellow solid. LC-MS: (ESI) m/z=414, 416 [M+H]$^+$ Intermediate 8-bromo-1-(3,3-difluoro-1-methylpiperidin-4-yl)-7-fluoro-3-methyl-1,3-dihydro-2H-imidazo[4,5-c]quinolin-2-one C5 was synthesized shown in FIG. 4.

Figure 5:
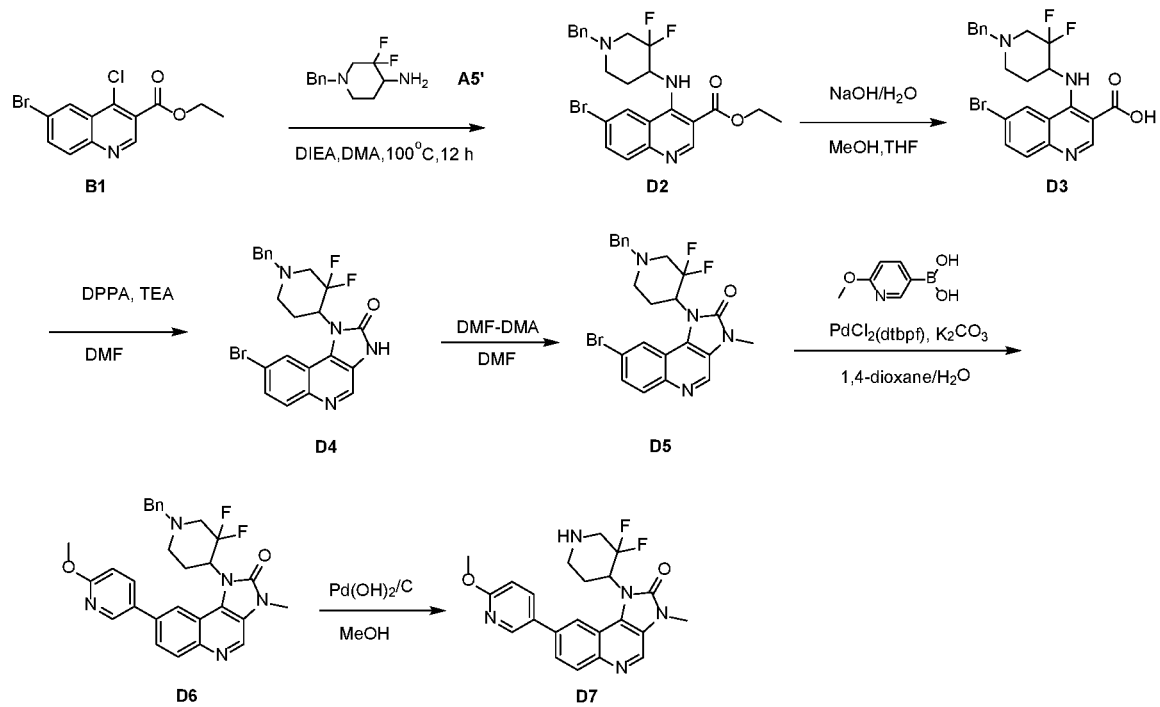
FIG. 5 illustrates the chemistry and synthesis of 1-(3,3-difluoropiperidin-4-yl)-8-(6-methoxypyridin-3-yl)-3-methyl-1,3-dihydro-2H-imidazo[4,5-c]quinolin-2-one D7

Step 1: A mixture of C1 (1.48 g, 4.45 mmol) in DMA (20 mL) was added A6 (1.09 g, 9.54 mmol) and DIEA (1.72 g, 13.35 mmol). The mixture was heated to 80° C. for 8 h. The mixture was cooled to room temperature and poured into a mixture of ethyl acetate (200 mL) and H$_2$O (100 mL), the organic layer was separated and washed with brine, dried over anhydrous Na$_2$SO$_4$, filtered, concentrated in vacuo to give C2 (2.2 g, 100%) as a brown solid. LC-MS: (ESI) m/z=448 [M+H]$^+$ Step 2: A mixture of C2 (2.2 g, 5 mmol) in MeOH/H$_2$O/THF (60 mL/20 mL/20 mL) was added NaOH (1 g, 25 mmol) at room temperature and heated to 60° C. for 2 h. The mixture was cooled to room temperature, concentrated in vacuo to remove organic layer. The residue was added to H$_2$O (50 mL), adjusted to pH=4 by addition of 10% HCl, filtered to give C3 (2 g, 92.4%) as a yellow solid. LC-MS: (ESI) m/z=420 [M+H]$^+$ Step 3: To a solution of C3 (1.93 g, 4.62 mmol) and DPPA (1.53 g, 5.55 mmol) in DMF (10 mL) was added TEA (1.4 g, 13.86 mmol). The mixture was stirred at 60° C. for 2 h. The reaction was cooled to room temperature and then poured into H$_2$O (80 mL), extracted with ethyl acetate (200 mL). The organic layer was separated and washed with brine, dried over anhydrous sodium sulfate, filtered and concentrated in vacuo. The residue was purified by silica gel column chromatography to give C4 (1.19 g, 61.7%) as a brown solid. $^1$H NMR (400 MHz, CD3OD_SPE) δ 9.04-8.73 (m, 1H), 8.69 (d, J=2.7 Hz, 1H), 8.54 (d, J=6.6 Hz, 1H), 7.80 (dd, J=9.7, 2.9 Hz, 1H), 5.20 (dd, J=23.7, 8.8 Hz, 1H), 3.80 (d, J=12.1 Hz, 1H), 3.21-2.83 (m, 2H), 2.66 (dd, J=28.4, 12.5 Hz, 1H), 2.54-2.41 (m, 4H), 2.07 (s, 1H). LC-MS: (ESI) m/z=417 [M+H]$^+$ Step 4: Methyl iodide (334 mg, 2.42 mmol) was added to a mixture of C4 (500 mg, 1.21 mmol), NaOH (73 mg, 1.82 mmol) and TBAHS (41 mg, 0.12 mmol) in DCM/H$_2$O (4 mL/3 mL). The resulting mixture was stirred at room temperature for 5 h. The cooled mixture was poured into a mixture of DCM (200 mL) and H2O (150 mL). The organic layer was separated and washed with brine, dried over anhydrous sodium sulfate, filtered, concentrated in vacuo. The residue was purified by Pre-TLC to give C5 (533 mg, 100%) as a brown solid. $^1$H NMR (400 MHz, DMSO) δ 9.09-8.95 (m, 1H), 8.89-8.53 (m, 1H), 8.03-7.96 (m, 1H), 5.31 (dd, J=25.6, 11.6 Hz, 1H), 3.73-3.60 (m, 1H), 3.54 (d, J=34.3 Hz, 3H), 3.28-3.12 (m, 3H), 2.71-2.54 (m, 2H), 2.48-2.29 (m, 4H), 1.98 (d, J=12.5 Hz, 1H). LC-MS: (ESI) m/z=431[M+H]$^+$ Intermediate 1-(3,3-difluoropiperidin-4-yl)-8-(6-methoxypyridin-3-yl)-3-methyl-1,3-dihydro-2H-imidazo[4,5-c]quinolin-2-one D7 was synthesized shown in FIG. 5.

Step 1: A mixture of B1 (5 g, 15.90 mmol), A5' (4.32 g, 19.07 mmol) and DIEA (3.54 g, 38.14 mmol) in DMA (50 mL) was heated to 100° C. for 12 hours. The mixture was poured into H$_2$O (100 mL), extracted with EtOAc (100 mL×3), the organic layer was washed with brine, dried over anhydrous Na$_2$SO$_4$, filtered and concentrated in vacuo. The residue was purified by column chromatography (DCM:MeOH=30:1) to give the compound D2 (3 g, 37.42%) as a yellow oil.

Step 2: A mixture of D2 (2.3 g, 4.56 mmol) in MeOH/H$_2$O/THF (20 mL/5 mL/5 mL) was added NaOH (0.65 g, 16.2 mmol) at room temperature and heated to 50° C. for 2 h. The mixture was cooled to room temperature, concentrated in vacuo to remove organic layer, and then the residue was added to H$_2$O (50 mL), adjusted to pH=4 by addition of 10% aqueous HCl, filtered to give D3 (2.0 g, 92.08%) as an off-white solid. LC-MS: (ESI) m/z=506.0 [M+H].

Step 3: A solution of D3 (2.0 g, 4.20 mmol), DPPA (1.7 g, 6.18 mmol), TEA (3.74 g, 25.1 mmol) in DMF (35 mL) was stirred at 60° C. for 2 h. The reaction mixture was cooled to room temperature. The mixture was poured into H$_2$O (50 mL), and then the precipitate was filtered. The solid was washed was H$_2$O once, and then the filtered cake was dried to give D4 (1.8 g, 90.57%) as a brown solid.

Step 4: To a mixture of D4 (1.80 g, 3.80 mmol) in DMF (25 mL) was added DMF-DMA (2.30 g, 19.2 mmol) at room temperature. After that the mixture was heated to 80° C. for 2 hours. The reaction mixture was cooled to room temperature and filtered. The filter cake was washed with H$_2$O, and dried to give D5 (1.0 g, 53.96%) as an off-white solid. LC-MS: (ESI) m/z=489.2 [M+H].

Step 5: A mixture of D5 (1.0 g, 2.05 mmol), (6-methoxypyridin-3-yl)boronic acid (377 mg, 2.46 mmol), PdCl$_2$(dtdppf) (240 mg, 0.21 mmol), K$_2$CO$_3$ (1.5 mg, 6.15 mmol) in 1,4-dioxane/H$_2$O (15 mL/4 mL) was degassed with N$_2$ for twice, and then heated to 80° C. for 3 h. The reaction mixture was poured into a mixture of DCM (50 mL) and H$_2$O (50 mL), and then the organic layer was washed with brine, dried over anhydrous Na$_2$SO$_4$, filtered and concentrated in vacuo. The residue was purified by column chromatography (DCM:MeOH=30:1) to give the compound D6 (1 g, 94.53%) as a white solid. 1H NMR (400 MHz, DMSO) δ 8.95 (d, J=32.8 Hz, 1H), 8.80 (s, 1H), 8.67 (s, J=43.2, 2.4 Hz, 1H), 8.37 (s, 1H), 8.23-8.09 (m, 2H), 8.00-7.90 (m, 1H), 7.40-7.23 (m, 5H), 7.01 (d, J=8.6 Hz, 1H), 5.59-5.23 (m, 1H), 3.98-3.90 (m, 3H), 3.79 (d, J=13.3 Hz, 1H), 3.73 (m, J=11.2, 4.4 Hz, 2H), 3.58 (m, J=32.0, 21.2 Hz, 4H), 3.11 (d, J=11.0 Hz, 1H), 3.03-2.87 (m, 1H), 2.74-2.55 (m, 1H), 2.40 (m, J=32.4, 18.1 Hz, 1H), 2.07-1.94 (m, 1H). LC-MS: (ESI) m/z=516.0 [M+H].

Step 6: The solution of D6 (400 mg, 0.78 mmol) in MeOH (10 mL) was added Pd(OH)$_2$/C (100 mg, 10% Pd, water <10%). The reaction mixture was stirred at 30° C. for 5 h. The reaction mixture was filtered, and the filtrate was concentrated in vacuo to give the compound D7 (300 mg, 90.89%) as a brown oil. LC-MS: (ESI) m/z=426.0 [M+H].

Figure 6:
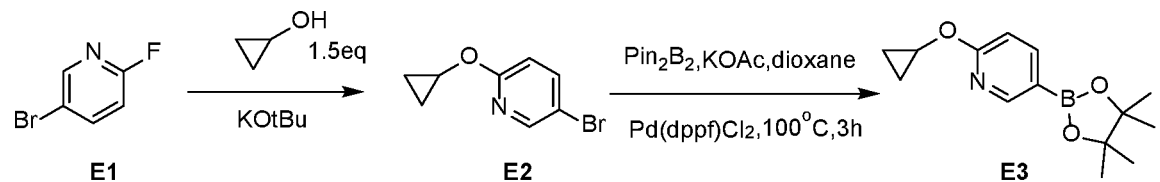
FIG. 6 illustrates the chemistry and synthesis of 2-cyclopropoxy-5-(4,4,5,5-tetramethyl-1,3,2-dioxaborolan-2-yl)pyridine E3

Intermediate 2-cyclopropoxy-5-(4,4,5,5-tetramethyl-1,3,2-dioxaborolan-2-yl)pyridine E3 was synthesized shown in FIG. 6.

Step 1: A mixture of E1 (1 g, 5.68 mmol), cyclopropanol (396 mg, 6.82 mmol) and KOtBu (2.1 g, 14.3 mmol) in THF (20 mL) was heated to 80° C. for 3 hours. The mixture was added H$_2$O (40 mL), extracted with EtOAc (40 mL×3), and then the organic layer was washed with brine, dried over anhydrous Na$_2$SO$_4$, filtered and concentrated in vacuo. The residue was purified by column chromatography (petroleum ether:EtOAc=4:1) to give the compound E2 (1.1 g, 90.4%) as a yellow oil.

Step 2: A mixture of E2 (1.1 g, 5.14 mmol), Pin$_2$B2 (1.57 g, 6.17 mmol) and KOAc (1.5 g, 15.42 mmol) in dioxane (20 mL) was heated to 100° C. for 8 hours. The mixture was added H$_2$O (40 mL), extracted with EtOAc (40 mL×3), and then the organic layer was washed with brine, dried over anhydrous Na$_2$SO$_4$, filtered and concentrated in vacuo. The residue was purified by column chromatography (petroleum ether:EtOAc=4:1) to give the compound E3 (700 mg, 52.23%) as a yellow oil.

Figure 7:
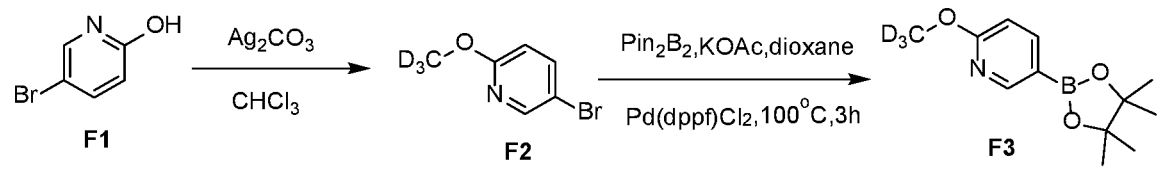
FIG. 7 illustrates the chemistry and synthesis of 2-(methoxy-d3)-5-(4,4,5,5-tetramethyl-1,3,2-dioxaborolan-2-yl)pyridine F3

Intermediate 2-(methoxy-d3)-5-(4,4,5,5-tetramethyl-1,3,2-dioxaborolan-2-yl)pyridine F3 was synthesized shown in FIG. 7.

Step 1: A mixture of F1 (1 g, 5.75 mmol) and Ag$_2$CO$_3$ (3.17 mg, 11.49 mmol) in CHCl$_3$ (15 mL) was stirred at 30° C. for 3 hours. The mixture was poured into a mixture of DCM (30 mL) and H$_2$O (30 mL), then the organic layer was washed with brine, dried over anhydrous Na$_2$SO$_4$, filtered and concentrated in vacuo to give the compound F2 (900 mg, 81.97%) as a colorless oil.

Step 2: A mixture of F2 (900 mg, 4.71 mmol), Pin$_2$B2 (1.44 g, 5.65 mmol) and KOAc (1.38 g, 14.51 mmol) in dioxane (20 mL) was heated to 100° C. for 8 hours. The mixture was added H$_2$O (40 mL), extracted with EtOAc (40 mL×3), then the organic layer was washed with brine, dried over anhydrous Na$_2$SO$_4$, filtered and concentrated in vacuo. The residue was purified by column chromatography (petroleum ether:EtOAc=4:1) to give the compound F3 (800 mg, 71.3%) as a yellow oil.

Figure 8:
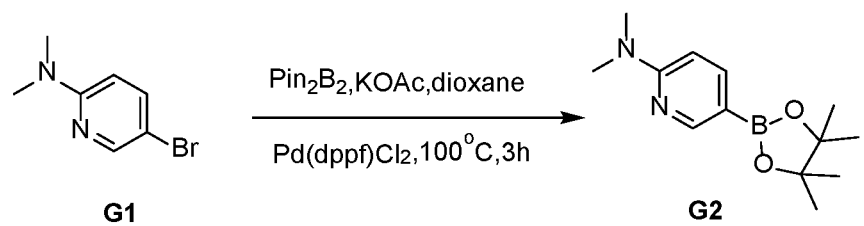
FIG. 8 illustrates the chemistry and synthesis of N,N-dimethyl-5-(4,4,5,5-tetramethyl-1,3,2-dioxaborolan-2-yl)pyridin-2-amine G2

Intermediate N,N-dimethyl-5-(4,4,5,5-tetramethyl-1,3,2-dioxaborolan-2-yl)pyridin-2-amine G2 was synthesized shown in FIG. 8.

Figure 9:
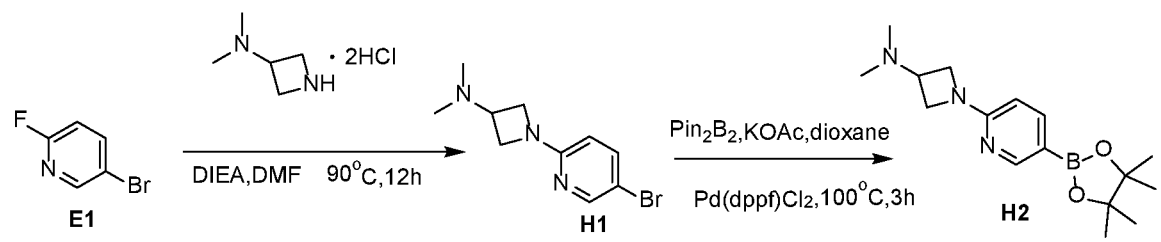
FIG. 9 illustrates the chemistry and synthesis of N,N-dimethyl-1-(5-(4,4,5,5-tetramethyl-1,3,2-dioxaborolan-2-yl)pyridin-2-yl)azetidin-3-amine H2

A mixture of G1 (550 mg, 2.74 mmol) and Pin$_2$B2 (835 mg, 3.288 mmol) in dioxane (20 mL) was added Pd(dppf)Cl$_2$ (201 mg, 0.274 mmol) and KOAc (807 mg, 8.22 mmol), the mixture was stirred at 100° C. for 3 h. The mixture was cooled to room temperature, filtered, concentrated in vacuo and purified by silica gel column chromatography (DCM:MeOH=10:1) to give G2 (300 mg, 44.1%). LC-MS: (ESI) m/z=248, 249[M+H]$^+$ Intermediate N,N-dimethyl-1-(5-(4,4,5,5-tetramethyl-1,3,2-dioxaborolan-2-yl)pyridin-2-yl)azetidin-3-amine H2 was synthesized shown in FIG. 9.

Figure 10:
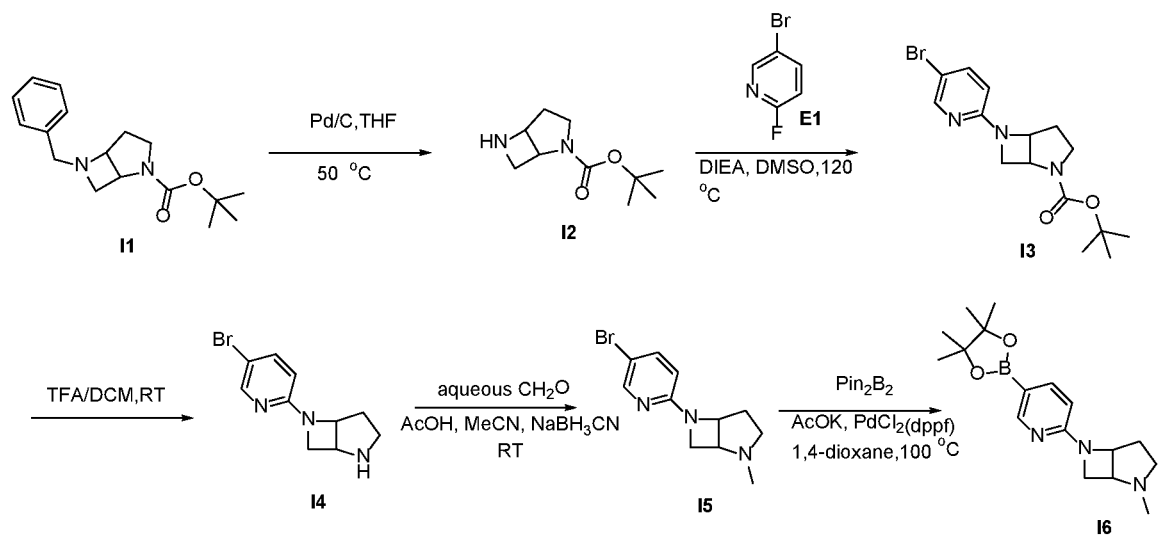
FIG. 10 illustrates the chemistry and synthesis of 2-methyl-6-(5-(4,4,5,5-tetramethyl-1,3,2-dioxaborolan-2-yl)pyridin-2-yl)-2,6-diazabicyclo[3.2.0]heptane I6

Step 1: A mixture of E1 (550 mg, 3.1 mmol) and N,N-dimethylazetidin-3-amine (805 mg, 4.65 mmol) in DMF (5 mL) was added DIEA (2003 mg, 15.5 mmol), the mixture was stirred at 90° C. for 12 h. The mixture was cooled to room temperature, poured into water and extracted with ethyl acetate. The organic layer was washed with brine, dried over anhydrous Na$_2$SO$_4$, concentrated in vacuo and purified by silica gel column chromatography (DCM:MeOH=10:1) to give H1 (438 mg, 55%). LC-MS: (ESI) m/z=257, 258[M+H]$^+$ Step 2: A mixture of H1 (438 mg, 1.71 mmol) and Pin$_2$B$_2$ (521 mg, 2.05 mmol) in dioxane (20 mL) was added Pd(dppf)Cl$_2$ (125 mg, 0.171 mmol) and KOAc (503 mg, 5.13 mmol), and then the mixture was stirred at 100° C. for 3 h. The mixture was cooled to room temperature, filtered, concentrated in vacuo and purified by silica gel column chromatography (DCM:MeOH=10:1) to give H2 (359 mg, 63.6%). LC-MS: (ESI) m/z=303, 304[M+H]$^+$ Intermediate 2-methyl-6-(5-(4,4,5,5-tetramethyl-1,3,2-dioxaborolan-2-yl)pyridin-2-yl)-2,6-diazabicyclo[3.2.0]heptane I6 was synthesized shown in FIG. 10.

Step 1: A mixture of I1 (50 mg, 0.174 mmol) in THF (5 mL) was added Pd/C (10 mg, 0.08 mmol). The mixture was heated to 50° C. for 12 h under H$_2$. The mixture was filter, the filtrate concentrated in vacuo to give I2 (30 mg, 90%) as an off-white solid. LC-MS: (ESI) m/z=198.9[M+H]$^+$ Step 2: A mixture of I2 (30 mg, 0.152 mmol) in DMSO (3 mL) was added E1 (40 mg, 0.5 mmol) and DIEA (28 mg, 0.3 mmol) at room temperature and heated to 120° C. for 2 h. The reaction was cooled to room temperature and then poured into H$_2$O (50 mL), the organic layer was washed with brine, dried over anhydrous Na$_2$SO$_4$, purified by column (DCM:MeOH=30:1) to give I3 (33 mg, 78.57%) as an off-white solid.

Step 3: To a solution of I3 (33 mg, 0.093 mmol) in DCM (3 mL) was added TFA (19 mg, 0.27 mmol). The mixture was stirred at rt for 1 h. The mixture was poured into a mixture of DCM (15 mL) and H$_2$O (15 mL), the organic layer was washed with brine, dried over anhydrous Na$_2$SO$_4$, filtered and concentrated in vacuo. The residue was purified by column (DCM:MeOH=30:1) to give I4 (20 mg, 91.82%) as a brown solid.

Step 4: To a solution of I4 (20 mg, 0.079 mmol) in AcOH (2 mL), MeCN (2 mL) was added NaBH$_3$CN (13 mg, 0.16 mmol) and aqueous CH$_2$O under N$_2$. The mixture was stirred at room temperature for 1 h. The mixture was poured into a mixture of DCM (15 mL) and H$_2$O (15 mL), the organic layer was washed with brine, dried over anhydrous Na$_2$SO$_4$, filtered and concentrated in vacuo. The residue was purified by column (DCM:MeOH=30:1) to give I5 (12 mg, 91.82%) an off-white solid.

Step 5: A mixture of I5 (12 mg, 0.045 mmol), Pin$_2$B$_2$ (20 mg, 0.13 mmol), PdCl$_2$(dppf) (3 mg, 0.004 mmol) and AcOH (6 mg, 0.08 mmol) in 1,4-dioxane (3 mL) was degassed with N₂ for twice, then heated to 100° C. for 3 h. The mixture was poured into a mixture of DCM (15 mL) and H₂O (15 mL), the organic layer was washed with brine, dried over anhydrous Na₂SO₄, filtered and concentrated in vacuo. The residue was purified by column (DCM:MeOH=30:1) to give I6 (15 mg, 56.07%) as a white solid.

Figure 11:
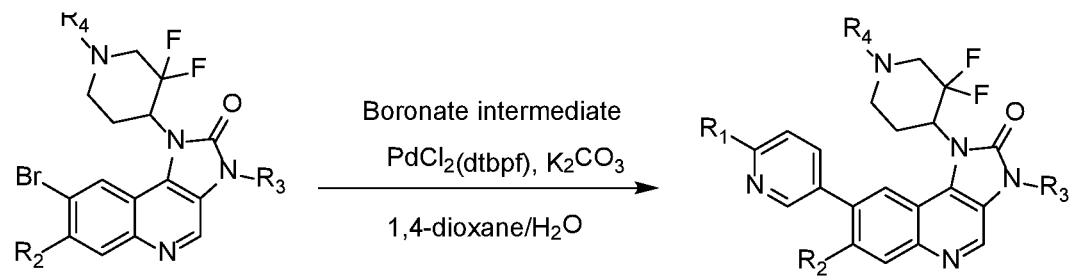
FIG. 11 illustrates the general synthetic method for the coupling of boronate intermediate with aryl bromide

General method for the coupling of boronate intermediate with aryl bromide shown in FIG. 11.

A mixture of starting material (1 eq.), boronate intermediate (1.2 eq.), PdCl₂(dtdppf) (1 eq.), K₂CO₃ (3 eq.)) in 1,4-dioxane/H₂O (2.5:1, v/v, 0.035 M) was degassed with N₂ for twice, then heated to 80° C. for 3 h. The mixture was poured into a mixture of DCM and H₂O, the organic layer was washed with brine, dried over anhydrous Na₂SO₄, filtered and concentrated. The residue was purified by column (DCM:MeOH=30:1) to give the desired coupling product.

Figure 12:
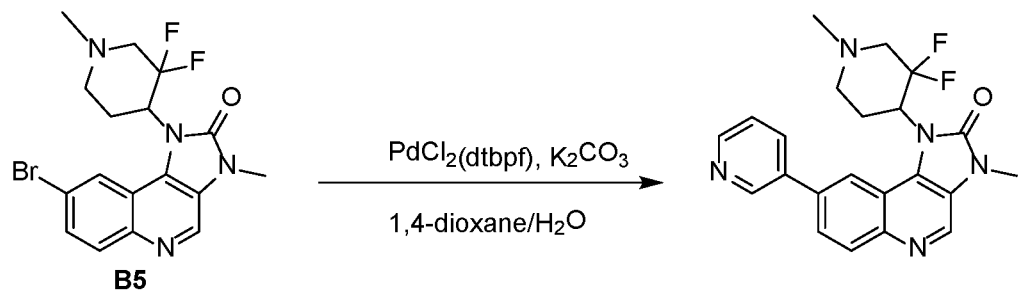
FIG. 12 illustrates the representative example using general synthetic method for the coupling of boronate intermediate with aryl bromide

Representative example using general method for the coupling of boronate intermediate with aryl bromide shown in FIG. 12.

A mixture of B5 (2 g, 4.87 mmol), pyridin-3-ylboronic acid (888 mg, 5.844 mmol), PdCl₂(dtdppf) (318 mg, 4.87 mmol), K₂CO₃ (2 g, 14.61 mmol) in 1,4-dioxane/H₂O (100 mL/40 mL) was degassed with N₂ for twice, then heated to 80° C. for 3 h. The mixture was poured into a mixture of DCM (500 mL) and H₂O (500 mL), the organic layer was washed with brine, dried over anhydrous Na₂SO₄, purified by column chromatography (DCM:MeOH=30:1) to give the product (1.22 g, 57.07%) as a white solid. ¹H NMR (400 MHz, DMSO) δ 9.09 (d, J=42.0, 1.9 Hz, 1H), 8.98 (d, J=26.8 Hz, 1H), 8.90 (s, 1H), 8.67-8.61 (m, 1H), 8.48 (s, 1H), 8.34-8.19 (m, 1H), 8.18 (d, J=8.8 Hz, 1H), 8.15-8.05 (m, 1H), 7.68-7.48 (m, 1H), 5.57-5.25 (m, 1H), 3.69 (d, J=4.0 Hz, 1H), 3.56 (d, J=33.2 Hz, 3H), 3.44-3.34 (m, 1H), 3.30 (s, 1H), 3.11 (d, J=11.2 Hz, 1H), 2.94 (d, J=12.0 Hz, 1H), 2.73-2.53 (m, 1H), 2.42 (dd, J=32.4, 16.4 Hz, 4H), 2.11-1.92 (m, 1H). LC-MS: (ESI) m/z=410.1 [M+H]⁺

Figure 13:
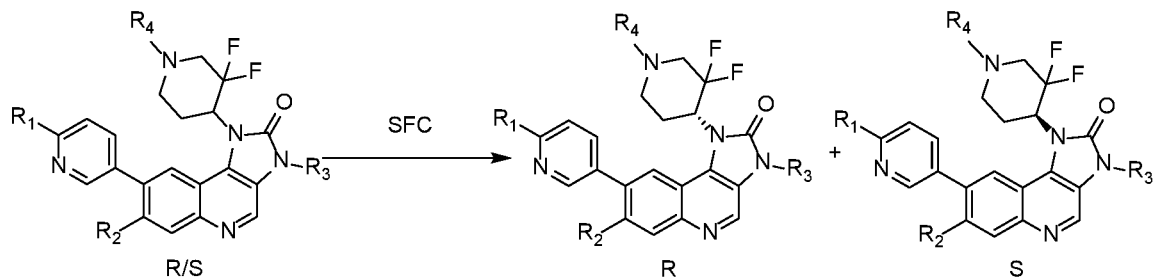
FIG. 13 illustrates the general method for the chiral separation of racemic product 1-13

General method for the chiral separation of racemic product 1-13 shown in FIG. 13.

The sample was dissolved in about 150 mL EtOH and injected every 7 mL using Chiral Pre-SFC column (Waters SFC 150, 250*25 mm 10 μm DAICELCHIRALPAK®AS SFC column) to separate the enantiomers (55:45 Supercritical CO₂:EtOH mobile phase at flow rate of 70 g/min and 214 nm wavelength to monitor).

Figure 14:
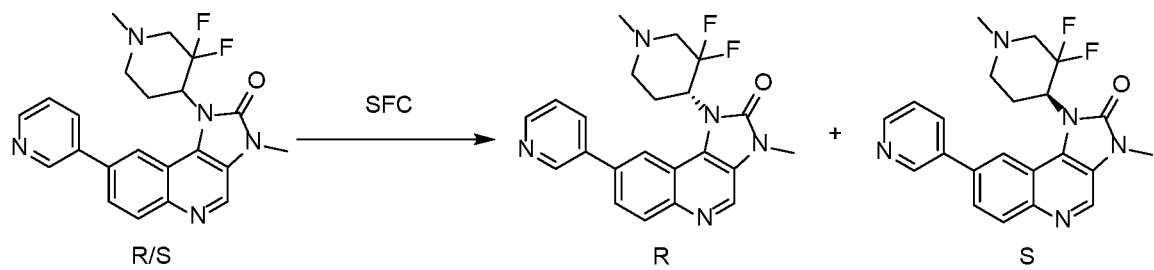
FIG. 14 illustrates the representative example using general method for the chiral separation of racemic product

Representative example using general method for the chiral separation of racemic product shown in FIG. 14.
Follow the general method for the chiral separation of racemic product, 1.22 g of 1-(3,3-difluoro-1-methylpiperidin-4-yl)-3-methyl-8-(pyridin-3-yl)-1,3-dihydro-2H-imidazo[4,5-c]quinolin-2-one gave (R)-1-(3,3-difluoro-1-methylpiperidin-4-yl)-3-methyl-8-(pyridin-3-yl)-1,3-dihydro-2H-imidazo[4,5-c]quinolin-2-one (500 mg, 99% yellow solids), ¹H NMR (400 MHz, DMSO) δ 9.09 (d, J=42.0, 1.9 Hz, 1H), 8.98 (d, J=26.8 Hz, 1H), 8.90 (s, 1H), 8.67-8.61 (m, 1H), 8.48 (s, 1H), 8.34-8.19 (m, 1H), 8.18 (d, J=8.8 Hz, 1H), 8.15-8.05 (m, 1H), 7.68-7.48 (m, 1H), 5.57-5.25 (m, 1H), 3.69 (d, J=4.0 Hz, 1H), 3.56 (d, J=33.2 Hz, 3H), 3.44-3.34 (m, 1H), 3.30 (s, 1H), 3.11 (d, J=11.2 Hz, 1H), 2.94 (d, J=12.0 Hz, 1H), 2.73-2.53 (m, 1H), 2.42 (dd, J=32.4, 16.4 Hz, 4H), 2.11-1.92 (m, 1H). LC-MS: (ESI) m/z=410.1 [M+H] SFC: 99% and (S)-1-(3,3-difluoro-1-methylpiperidin-4-yl)-3-methyl-8-(pyridin-3-yl)-1,3-dihydro-2H-imidazo[4,5-c]quinolin-2-one (504 mg, 99.03% yellow solid), 1H NMR (400 MHz, DMSO) δ 9.09 (d, J=42.0, 1.9 Hz, 1H), 8.98 (d, J=26.8 Hz, 1H), 8.90 (s, 1H), 8.67-8.60 (m, 1H), 8.48 (s, 1H), 8.34-8.19 (m, 1H), 8.18 (d, J=8.8 Hz, 1H), 8.15-8.05 (m, 1H), 7.68-7.48 (m, 1H), 5.57-5.24 (m, 1H), 3.71-3.62 (m, 1H), 3.56 (d, J=33.2 Hz, 3H), 3.44-3.34 (m, 1H), 3.30 (s, 1H), 3.10 (d, J=11.2 Hz, 1H), 2.94 (d, J=12.0 Hz, 1H), 2.73-2.53 (m, 1H), 2.42 (dd, J=32.4, 16.4 Hz, 4H), 2.11-1.93 (m, 1H). LC-MS: (ESI) m/z=410.1 [M+H] SFC: 99%.

Example 2

Figure 15:
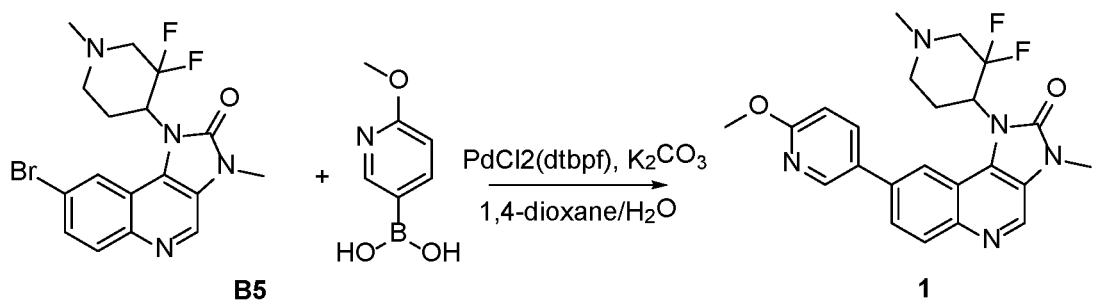
FIG. 15 illustrates the chemistry and synthesis of (R/S)-1-(3,3-difluoro-1-methylpiperidin-4-yl)-8-(6-methoxypyridin-3-yl)-3-methyl-1,3-dihydro-2H-imidazo[4,5-c]quinolin-2-one (1)

Synthesis of Compound 1 Shown in FIG. 15: Synthesis of (R/S)-1-(3,3-difluoro-1-methylpiperidin-4-yl)-8-(6-methoxypyridin-3-yl)-3-methyl-1,3-dihydro-2H-imidazo[4,5-c]quinolin-2-one Follow the general method for the coupling of boronate intermediate with aryl bromide, a mixture of B5 (2 g, 4.87 mmol), (6-methoxypyridin-3-yl)boronic acid (888 mg, 5.844 mmol), PdCl₂(dtdppf) (318 mg, 4.87 mmol) and K₂CO₃ (2 g, 14.61 mmol) in 1,4-dioxane/H₂O (100 mL/40 mL) gave the compound 1 (1.2 g, 56.07%) as a white solid. ¹H NMR (400 MHz, DMSO) δ 8.94 (d, J=25.6 Hz, 1H), 8.80 (s, 1H), 8.68 (dd, J=39.6, 2.0 Hz, 1H), 8.38 (s, 1H), 8.29-8.10 (m, 2H), 8.05-7.95 (m, 1H), 7.01 (dd, J=18.8, 8.8 Hz, 1H), 5.45-5.25 (m, 1H), 3.94 (d, J=4.8 Hz, 3H), 3.73-3.61 (m, 1H), 3.56 (d, J=33.2 Hz, 3H), 3.44-3.35 (m, 1H), 3.15-2.87 (m, 1H), 2.72-2.53 (m, 1H), 2.48-2.39 (m, 2H), 2.35 (s, 2H), 2.10-1.91 (m, 1H). LC-MS: (ESI) m/z=440.1 [M+H]⁺

Example 3

Figure 16:
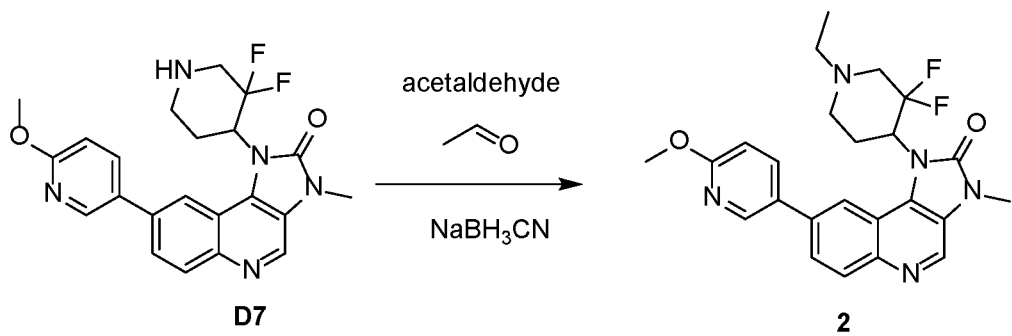
FIG. 16 illustrates the chemistry and synthesis of (R/S)-1-(1-ethyl-3,3-difluoropiperidin-4-yl)-8-(6-methoxypyridin-3-yl)-3-methyl-1,3-dihydro-2H-imidazo[4,5-c]quinolin-2-one (2)

Synthesis of Compound 2 Shown in FIG. 16: Synthesis of (R/S)-1-(1-ethyl-3,3-difluoropiperidin-4-yl)-8-(6-methoxypyridin-3-yl)-3-methyl-1,3-dihydro-2H-imidazo[4,5-c]quinolin-2-one To a mixture of D7 (100 mg, 0.24 mmol) in acetaldehyde (10 mL) was added NaBH₃CN (18 mg, 0.28 mmol). The mixture was stirred at 30° C. for 5 hours. The mixture was added H₂O (20 mL), extracted with EtOAc (20 mL×3), and then the organic layer was concentrated in vacuo. The residue was purified by column chromatography (DCM: MeOH=30:1) to give the compound 2 (10 mg, 9.38%) as a white solid. LC-MS: (ESI) m/z=454.0 [M+H]. ¹H NMR (400 MHz, DMSO-d₆) δ 8.99-8.89 (m, 1H), 8.80 (s, 0.4H), 8.75-8.61 (m, 1H), 8.39 (s, 0.5H), 8.25-8.11 (m, 2H), 8.04-7.91 (m, 1H), 7.05-6.90 (m, 1H), 5.55-5.24 (m, 1H), 3.93 (d, J=8.0 Hz, 3H), 3.70-3.62 (m, 0.3H), 3.60 (s, 1H), 3.52 (s, 2H), 3.49-3.35 (m, 1H), 3.20 (d, J=8.0 Hz, 0.7H), 3.04 (d, J=8.0 Hz, 1H), 2.66-2.59 (m, 1H), 2.58-2.53 (m, 1H), 2.46-2.38 (m, 2H), 2.10-1.93 (m, 1H), 1.16-1.04 (m, 3H).

Example 4

Figure 17:
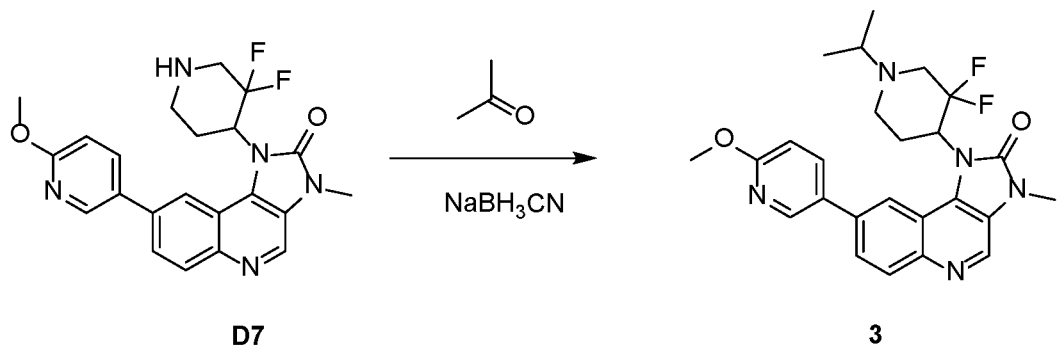
FIG. 17 illustrates the chemistry and synthesis of (R/S)-1-(3,3-difluoro-1-isopropylpiperidin-4-yl)-8-(6-methoxypyridin-3-yl)-3-methyl-1,3-dihydro-2H-imidazo[4,5-c]quinolin-2-one (3)

Synthesis of Compound 3 Shown in FIG. 17: Synthesis of (R/S)-1-(3,3-difluoro-1-isopropylpiperidin-4-yl)-8-(6-methoxypyridin-3-yl)-3-methyl-1,3-dihydro-2H-imidazo[4,5-c]quinolin-2-one To a solution of D7 (100 mg, 0.24 mmol) in propan-2-one (10 mL) was added NaBH₃CN (22 mg, 0.35 mmol). The reaction mixture was stirred at 30° C. for 5 hours. The mixture was added H₂O (20 mL), extracted with EtOAc (20 mL×3), and then the organic layer was concentrated. The residue was purified by column chromatography (DCM: MeOH=30:1) to give the compound 3 (10 mg, 9.74%) as a white solid. LC-MS: (ESI) m/z=468.2 [M+H]. $^1$H NMR (400 MHz, DMSO-d$_6$) δ 8.99-8.89 (m, 1H), 8.80 (s, 0.5H), 8.73-8.60 (m, 1H), 8.39 (s, 0.5H), 8.22-8.09 (m, 2H), 8.02-7.90 (m, 1H), 7.04-6.89 (m, 1H), 5.52-5.19 (m, 1H), 3.95-3.88 (m, 3H), 3.61-3.35 (m, 4H), 3.15-2.53 (m, 5H), 2.09-1.93 (m, 1H), 1.05 (d, J=8.0 Hz, 6H).

Example 5

Figure 18:
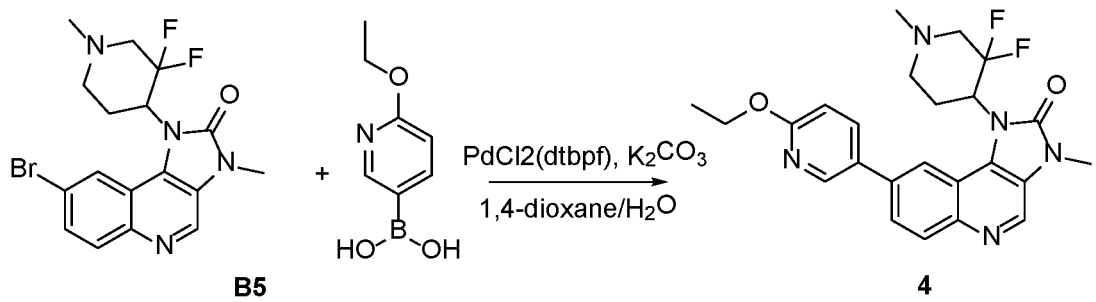
FIG. 18 illustrates the chemistry and synthesis of (R/S)-1-(3,3-difluoro-1-methylpiperidin-4-yl)-8-(6-ethoxypyridin-3-yl)-3-methyl-1,3-dihydro-2H-imidazo[4,5-c]quinolin-2-one (4)

Synthesis of Compound 4 Shown in FIG. 18: Synthesis of (R/S)-1-(3,3-difluoro-1-methylpiperidin-4-yl)-8-(6-ethoxypyridin-3-yl)-3-methyl-1,3-dihydro-2H-imidazo[4,5-c]quinolin-2-one Follow the general method for the coupling of boronate intermediate with aryl bromide, A mixture of B5 (2 g, 4.87 mmol), (6-ethoxypyridin-3-yl)boronic acid (970 mg, 5.844 mmol), PdCl$_2$(dtdppf) (318 mg, 0.49 mmol) and K$_2$CO$_3$ (2 g, 14.61 mmol) in 1,4-dioxane/H$_2$O (100 mL/40 mL) gave the compound 4 (1.3 g, 59.1%) as a white solid. LC-MS: (ESI) m/z=454.1 [M+H]$^+$, $^1$H NMR (400 MHz, DMSO-d$_6$) δ 9.03-8.95 (m, 1H), 8.79 (s, 0.35H), δ 8.74-8.53 (m, 1H), δ 8.44-8.33 (m, 1H), 8.30-8.06 (m, 2H), 8.05-7.85 (m, 1H), 7.05-6.96 (m, 1H), 5.58-5.20 (m, 1H), 4.39 (s, 2H), 3.74-3.62 (m, 0.57H), 3.62-3.42 (m, 3H), 3.45-3.36 (m, 0.47H), 3.17-2.93 (m, 2H), 2.74-2.56 (m, 1H), 2.49-2.29 (m, 4H), 2.13-1.96 (m, 1H), 1.36 (s, 3H).

Example 6

Figure 19:
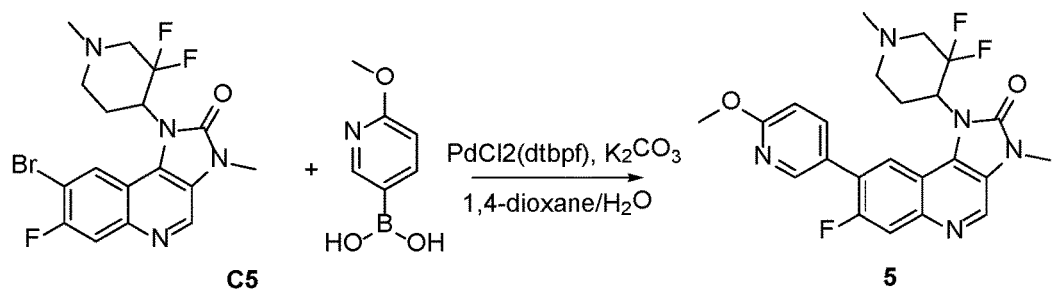
FIG. 19 illustrates the chemistry and synthesis of (R/S)-1-(3,3-difluoro-1-methylpiperidin-4-yl)-7-fluoro-8-(6-methoxypyridin-3-yl)-3-methyl-1,3-dihydro-2H-imidazo[4,5-c]quinolin-2-one (5)

Synthesis of Compound 5 Shown in FIG. 19: Synthesis of (R/S)-1-(3,3-difluoro-1-methylpiperidin-4-yl)-7-fluoro-8-(6-methoxypyridin-3-yl)-3-methyl-1,3-dihydro-2H-imidazo[4,5-c]quinolin-2-one Follow the general method for the coupling of boronate intermediate with aryl bromide, a mixture of C5 (150 mg, 0.35 mmol), (6-methoxypyridin-3-yl)boronic acid (70 mg, 0.46 mmol), PdCl$_2$(dtdppf) (14 mg, 0.02 mmol), K$_2$CO$_3$ (145 mg, 1.05 mmol) in 1,4-dioxane/H$_2$O (4 mL/0.8 mL) was degassed with N$_2$ for twice, then heated to 90° C. for 3 h. The mixture was poured into H$_2$O (20 mL), extracted with DCM (45 mL), the organic layer was washed with brine, dried over anhydrous Na$_2$SO$_4$, filtered and concentrated in vacuo. The residue was purified by Pre-HPLC(FA) to give compound 5 (79.2 mg, 49.4%) as a white solid. $^1$H NMR (400 MHz, DMSO) δ 8.98 (d, J=27.3 Hz, 1H), 8.72 (d, J=8.0 Hz, 1H), 8.63-8.13 (m, 2H), 8.17-7.95 (m, 1H), 7.93 (d, J=12.2 Hz, 1H), 7.11-6.86 (m, 1H), 5.49-5.24 (m, 1H), 3.94 (d, J=5.6 Hz, 3H), 3.68-3.35 (m, 4H), 3.08 (d, J=10.8 Hz, 1H), 2.99-2.57 (m, 2H), 2.48-2.17 (m, 4H), 2.08-1.79 (m, 1H). LC-MS: (ESI) m/z=458.3 [M+H]$^+$ Example 7

Figure 20:
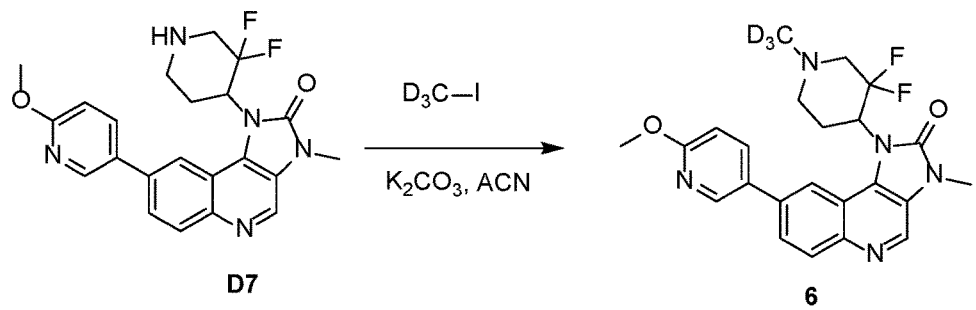
FIG. 20 illustrates the chemistry and synthesis of (R/S)-1-(3,3-difluoro-1-(methyl-d3)piperidin-4-yl)-8-(6-methoxypyridin-3-yl)-3-methyl-1,3-dihydro-2H-imidazo[4,5-c]quinolin-2-one (6)

Synthesis of Compound 6 Shown in FIG. 20: Synthesis of (R/S)-1-(3,3-difluoro-1-(methyl-d3)piperidin-4-yl)-8-(6-methoxypyridin-3-yl)-3-methyl-1,3-dihydro-2H-imidazo[4,5-c]quinolin-2-one To a solution of D7 (100 mg, 0.24 mmol) in ACN (20 mL) was stirred at 28° C., K$_2$CO$_3$ (71.4 mg, 0.52 mmol) was added into the mixture and stirred at 28° C. for 30 min. Then CD$_3$I (51 mg, 0.35 mmol) was added dropwise into the reaction mixture. The mixture was stirred at room temperature for 16 hours. The reaction mixture was added H$_2$O (10 mL), extracted with EtOAc (30 mL×3), and then the organic layer was washed with brine, dried over anhydrous Na$_2$SO$_4$, filtered and concentrated in vacuo. The residue was purified by column chromatography (DCM:MeOH=30:1) to give the compound 6 (2.6 mg, 2.5%) as a white solid. LC-MS: (ESI) m/z=442.2 [M+H]. $^1$H NMR (400 MHz, DMSO-d$_6$) δ 8.99-8.89 (m, 1H), 8.80 (s, 0.3H), 8.75-8.61 (m, 1H), 8.38 (s, 0.7H), 8.25-8.11 (m, 2H), 8.05-7.91 (m, 1H), 7.05-6.95 (m, 1H), 5.55-5.24 (m, 1H), 3.94 (d, J=4.0 Hz, 3H), 3.70-3.62 (m, 0.6H), 3.60 (s, 1H), 3.51 (s, 2H), 3.43-3.38 (m, 0.4H), 3.15-3.06 (m, 0.4H), 2.99-2.90 (m, 1H), 2.64-2.54 (m, 0.6H), 2.45-2.38 (m, 1H), 2.08-1.93 (m, 1H), 1.23 (s, 1H).

Example 8

Figure 21:
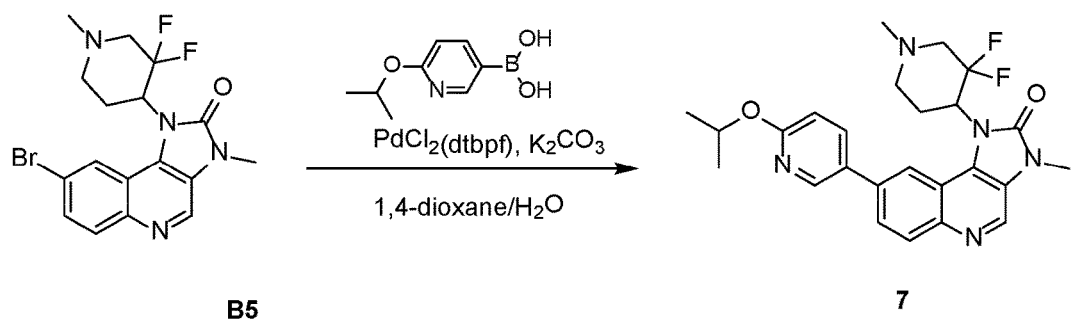
FIG. 21 illustrates the chemistry and synthesis of (R/S)-1-(3,3-difluoro-1-methylpiperidin-4-yl)-8-(6-isopropoxypyridin-3-yl)-3-methyl-1,3-dihydro-2H-imidazo[4,5-c]quinolin-2-one (7)

Synthesis of Compound 7 Shown in FIG. 21: Synthesis of (R/S)-1-(3,3-difluoro-1-methylpiperidin-4-yl)-8-(6-isopropoxypyridin-3-yl)-3-methyl-1,3-dihydro-2H-imidazo[4,5-c]quinolin-2-one Follow the general method for the coupling of boronate intermediate with aryl bromide, a mixture of B5 (100 mg, 0.24 mmol), (6-isopropoxypyridin-3-yl)boronic acid (52.8 mg, 0.29 mmol), PdCl$_2$(dtdppf) (16 mg, 0.02 mmol) and K$_2$CO$_3$ (89 mg, 0.73 mmol) in 1,4-dioxane/H$_2$O (10 mL/4 mL) gave the compound 7 (10.6 mg, 9.4%) as a white solid. LC-MS: (ESI) m/z=468.2 [M+H]$^+$. $^1$H NMR (400 MHz, DMSO-d$_6$) δ 8.99-8.89 (m, 1H), 8.91-8.77 (m, 0.35H), 8.73-8.57 (m, 1H), 8.36 (s, 1H), 8.27-8.07 (m, 2H), 8.05-7.90 (m, 1H), 6.99-6.94 (m, 1H), 5.52-5.26 (m, 2H), 3.66-3.62 (m, 0.5H), 3.61-3.49 (m, 3H), 3.45-3.37 (m, 0.5H), 2.99-2.87 (m, 1H), 2.47-2.39 (m, 3H), 2.36-2.31 (m, 2H), 2.10-1.91 (m, 1H), 1.36-1.31 (m, 6H).

Example 9

Figure 22:
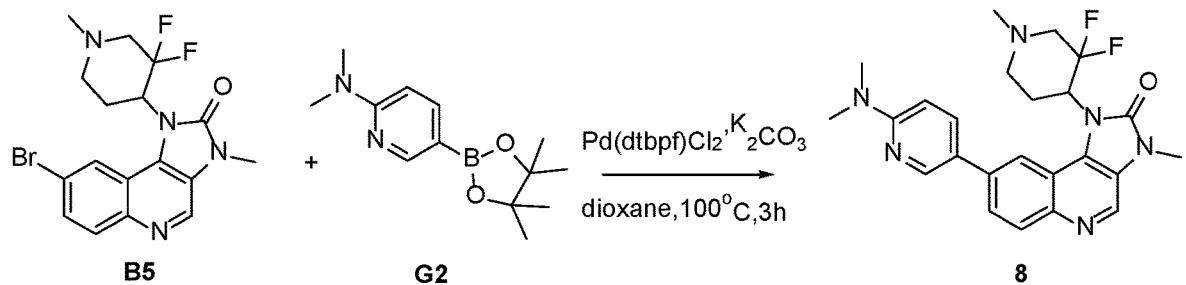
FIG. 22 illustrates the chemistry and synthesis of (R/S)-1-(3,3-difluoro-1-methylpiperidin-4-yl)-8-(6-(dimethylamino)pyridin-3-yl)-3-methyl-1,3-dihydro-2H-imidazo[4,5-c]quinolin-2-one (8)

Synthesis of Compound 8 Shown in FIG. 22: Synthesis of (R/S)-1-(3,3-difluoro-1-methylpiperidin-4-yl)-8-(6-(dimethylamino)pyridin-3-yl)-3-methyl-1,3-dihydro-2H-imidazo[4,5-c]quinolin-2-one Follow the general method for the coupling of boronate intermediate with aryl bromide, a mixture of B5 (300 mg, 0.73 mmol) and G2 (181 mg, 0.73 mmol) in dioxane/H$_2$O (10 mL/2 mL) was added Pd(dtbpf)Cl$_2$ (53 mg, 0.073 mmol) and K$_2$CO$_3$ (302 mg, 2.19 mmol) to give compound 8 (321 mg, 97%). $^1$H NMR (400 MHz, MeOD) δ 8.88-8.75 (m, 1H), 8.53 (dd, J=41.6, 2.4 Hz, 1H), 8.37 (s, 1H), 8.12 (t, J=8.9 Hz, 1H), 8.02-7.87 (m, 2H), 6.83 (dd, J=19.9, 9.0 Hz, 1H), 5.43 (dd, J=26.8, 8.8 Hz, 1H), 3.89-3.74 (m, 1H), 3.67 (s, 1H), 3.59 (s, 2H), 3.44 (d, J=29.6 Hz, 1H), 3.17 (d, J=4.9 Hz, 6H), 3.10 (d, J=15.9 Hz, 1H), 2.75-2.50 (m, 2H), 2.43 (d, J=18.8 Hz, 3H), 2.08 (d, J=13.5 Hz, 1H). LC-MS: (ESI) m/z=452, 453 [M+H]$^+$ Example 10

Figure 23:
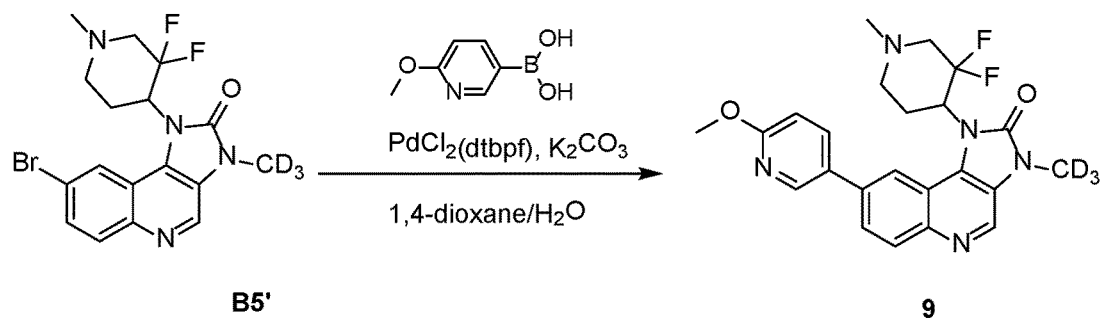
FIG. 23 illustrates the chemistry and synthesis of (R/S)-1-(3,3-difluoro-1-methylpiperidin-4-yl)-8-(6-methoxypyridin-3-yl)-3-(methyl-d3)-1,3-dihydro-2H-imidazo[4,5-c]quinolin-2-one (9)

Synthesis of Compound 9 Shown in FIG. 23: Synthesis of (R/S)-1-(3,3-difluoro-1-methylpiperidin-4-yl)-8-(6-methoxypyridin-3-yl)-3-(methyl-d3)-1,3-dihydro-2H-imidazo[4,5-c]quinolin-2-one Follow the general method for the coupling of boronate intermediate with aryl bromide, a mixture of B5' (100 mg, 0.24 mmol), (6-methoxypyridin-3-yl)boronic acid (44 mg, 0.29 mmol), PdCl$_2$(dtdppf) (31.8 mg, 0.02 mmol) and K$_2$CO$_3$ (200 mg, 1.46 mmol) in 1,4-dioxane/H$_2$O (100 mL/40 mL) gave the compound 9 (10 mg, 9.36%) as a white solid. LC-MS: (ESI) m/z=443.1 [M+H]+. $^1$H NMR (400 MHz, DMSO-d$_6$) δ 8.99-8.89 (m, 1H), 8.80 (s, 0.3H), 8.74-8.61 (m, 1H), 8.38 (s, 0.7H), 8.22-8.09 (m, 2H), 8.02-7.90 (m, 1H), 7.07-6.94 (m, 1H), 3.97-3.90 (m, 3H), 3.71-3.59 (m, 1H), 3.44-3.38 (m, 0.6H), 3.15-3.06 (m, 0.4H), 3.0-2.86 (m, 1H), 2.78-2.54 (m, 1H), 2.47-2.45 (m, 1H), 2.45-2.40 (m, 1H), 2.35 (s, 2H), 2.09-1.92 (m, 1H).

Example 11

Figure 24:
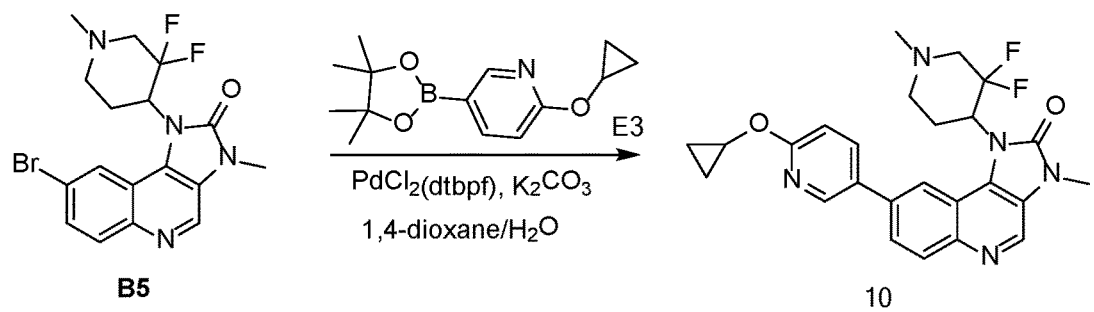
FIG. 24 illustrates the chemistry and synthesis of (R/S)-8-(6-cyclopropoxypyridin-3-yl)-1-(3,3-difluoro-1-methylpiperidin-4-yl)-3-methyl-1,3-dihydro-2H-imidazo[4,5-c]quinolin-2-one (10)

Synthesis of Compound 10 Shown in FIG. 24: Synthesis of (R/S)-8-(6-cyclopropoxypyridin-3-yl)-1-(3,3-difluoro-1-methylpiperidin-4-yl)-3-methyl-1,3-dihydro-2H-imidazo[4,5-c]quinolin-2-one Follow the general method for the coupling of boronate intermediate with aryl bromide, a mixture of B5 (200 mg, 0.47 mmol), E3 (152 mg, 0.58 mmol), PdCl$_2$(dtdppf) (32 mg, 0.02 mmol) and K$_2$CO$_3$ (130 mg, 1.2 mmol) in 1,4-dioxane/H$_2$O (10 mL/4 mL) gave the compound 10 (10 mg, 4.42%) as a white solid. LC-MS: (ESI) m/z=466.2 [M+H]+. $^1$H NMR (400 MHz, DMSO-d$_6$) δ 8.99-8.90 (m, 1H), 8.93-8.77 (m, 0.35H), 8.76-8.62 (m, 1H), 8.45-8.33 (m, 1.3H), 8.29-8.10 (m, 2H), 8.05-7.91 (m, 1H), 7.15-6.93 (m, 1H), 5.57-5.23 (m, 1H), 4.36-4.22 (m, 1H), 3.70-3.56 (m, 2H), 3.52 (s, 2H), 3.14-3.06 (m, 0.5H), 2.97-2.89 (m, 1H), 2.72-2.54 (m, 0.5H), 2.47-2.41 (m, 2H), 2.35 (s, 2H), 2.09-1.92 (m, 1H), 0.95-0.77 (m, 2H), 0.74-0.66 (m, 2H).

Example 12

Figure 25:
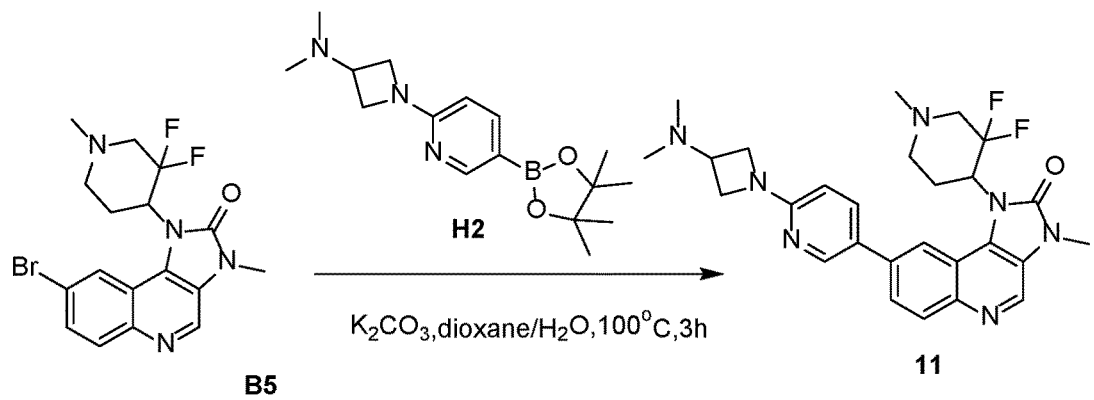
FIG. 25 illustrates the chemistry and synthesis of (R/S)-1-(3,3-difluoro-1-methylpiperidin-4-yl)-8-(6-(3-(dimethylamino)azetidin-1-yl)pyridin-3-yl)-3-methyl-1,3-dihydro-2H-imidazo[4,5-c]quinolin-2-one (11)

Synthesis of Compound 11 Shown in FIG. 25: Synthesis of (R/S)-1-(3,3-difluoro-1-methylpiperidin-4-yl)-8-(6-(3-(dimethylamino)azetidin-1-yl)pyridin-3-yl)-3-methyl-1,3-dihydro-2H-imidazo[4,5-c]quinolin-2-one Follow the general method for the coupling of boronate intermediate with aryl bromide, a mixture of H2 (359 mg, 1.18 mmol) and B5 (335 mg, 0.815 mmol) in dioxane/H$_2$O (10 mL/2 mL) was added K$_2$CO$_3$ (337 mg, 2.445 mmol) to give compound 11 (160 mg, 38.7%). $^1$H NMR (400 MHz, MeOD) δ 8.81 (dd, J=18.5, 3.4 Hz, 1H), 8.44 (dd, J=35.7, 33.3 Hz, 2H), 8.18-8.07 (m, 1H), 8.02-7.83 (m, 2H), 6.67-6.53 (m, 1H), 5.41 (dd, J=25.5, 11.6 Hz, 1H), 4.20 (t, J=7.1 Hz, 2H), 4.01-3.73 (m, 3H), 3.62 (dd, J=31.4, 2.3 Hz, 3H), 3.42-3.33 (m, 2H), 3.09 (d, J=11.9 Hz, 1H), 2.63 (dd, J=28.2, 12.3 Hz, 1H), 2.53-2.36 (m, 4H), 2.27 (s, 6H), 2.08 (d, J=13.7 Hz, 1H). LC-MS: (ESI) m/z=507, 508[M+H]+

Example 13

Figure 26:
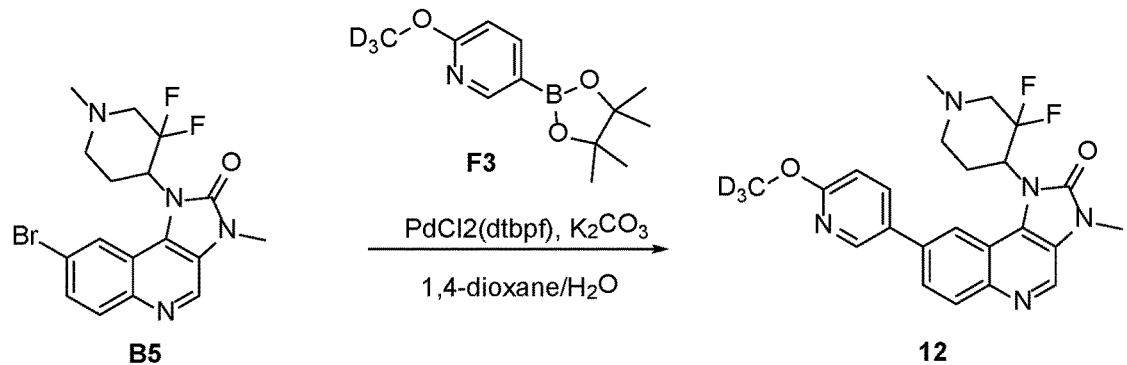
FIG. 26 illustrates the chemistry and synthesis of (R/S)-1-(3,3-difluoro-1-methylpiperidin-4-yl)-8-(6-(methoxy-d3)pyridin-3-yl)-3-methyl-1,3-dihydro-2H-imidazo[4,5-c]quinolin-2-one (12)

Synthesis of Compound 12 Shown in FIG. 26: Synthesis of (R/S)-1-(3,3-difluoro-1-methylpiperidin-4-yl)-8-(6-(methoxy-d3)pyridin-3-yl)-3-methyl-1,3-dihydro-2H-imidazo[4,5-c]quinolin-2-one Follow the general method for the coupling of boronate intermediate with aryl bromide, a mixture of F3 (200 mg, 0.84 mmol), B5 (287 mg, 0.70 mmol), PdCl$_2$(dtdppf) (31 mg, 4.87 mmol) and K$_2$CO$_3$ (347 mg, 2.52 mmol) in 1,4-dioxane/H$_2$O (10 mL/4 mL) gave the compound 12 (10 mg, 3.2%) as a white solid. LC-MS: (ESI) m/z=443.0 [M+H]+. $^1$H NMR (400 MHz, DMSO-d$_6$) δ 8.98-8.94 (m, 1H), 8.70-8.54 (s, 0.41H), 8.33-8.25 (m, 1H), 8.23 (s, 0.56H), 8.14-8.06 (m, 1H), 7.97-7.85 (m, 2H), 6.64-6.52 (m, 1H), 5.50-5.22 (m, 1H), 3.66-3.62 (m, 1H), 3.59 (s, 1H), 3.51 (s, 2H), 3.16-3.06 (m, 0.54H), 2.99-2.88 (m, 1H), 2.88-2.55 (m, 1.5H), 2.46 (s, 1H), 2.44-2.38 (m, 1H), 2.35 (s, 2H), 2.09-1.93 (m, 1H), 1.38 (s, 1H).

Example 14

Figure 27:
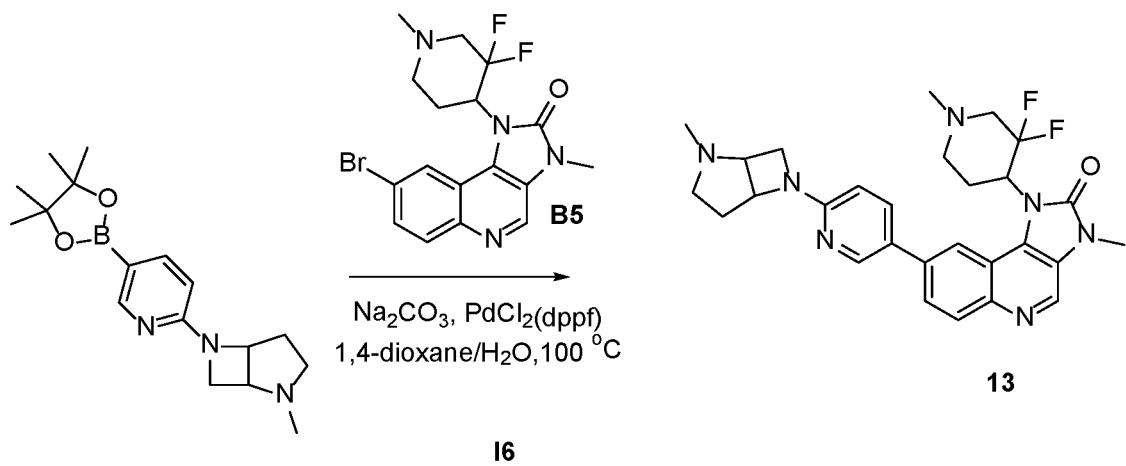
FIG. 27 illustrates the chemistry and synthesis of (R/S)-1-(3,3-difluoro-1-methylpiperidin-4-yl)-3-methyl-8-(6-((1R,5R/1S,5S)-(2-methyl-2,6-diazabicyclo[3.2.0]heptan-6-yl)pyridin-3-yl)-1,3-dihydro-2H-imidazo[4,5-c]quinolin-2-one (13)

Synthesis of Compound 13 Shown in FIG. 27: Synthesis of (R/S)-1-(3,3-difluoro-1-methylpiperidin-4-yl)-3-methyl-8-(6-((1R,5R/1S,5S)-(2-methyl-2,6-diazabicyclo[3.2.0]heptan-6-yl)pyridin-3-yl)-1,3-dihydro-2H-imidazo[4,5-c]quinolin-2-one Follow the general method for the coupling of boronate intermediate with aryl bromide, A mixture of I6 (15 mg, 0.038 mmol), B5 (12 mg, 0.058 mmol), PdCl$_2$(dppf) (3 mg, 0.0038 mmol), Na$_2$CO$_3$ (6 mg, 0.12 mmol) in 1,4-dioxane/H$_2$O (3 mL/0.5 mL) was degassed with N$_2$ for twice, then heated to 100° C. for 3 h. The mixture was poured into a mixture of DCM (15 mL) and H$_2$O (15 mL), the organic layer was washed with brine, dried over anhydrous Na$_2$SO$_4$, filtered and concentrated in vacuo. The residue was purified by column (DCM:MeOH=30:1) to give the compound 13 (2.8 mg, 47.1%) as a white solid. $^1$H NMR (400 MHz, DMSO) δ$^1$H NMR (400 MHz, MeOD) δ 8.80 (d, J=18.3 Hz, 1H), 8.46 (m, J=32.8, 2.4 Hz, 1H), 8.34 (s, 1H), 8.18-7.82 (m, 3H), 6.56 (d, J=18.0, 8.8 Hz, 1H), 5.40 (d, J=26.0, 10.4 Hz, 1H), 4.97 (t, J=4.8 Hz, 1H), 4.16-4.00 (m, 2H), 3.90-3.70 (m, 2H), 3.62 (d, J=31.2 Hz, 3H), 3.43-3.34 (m, 1H), 3.15-3.03 (m, 2H), 2.89 (d, J=10.8, 4.8 Hz, 1H), 2.64 (d, J=28.0, 12.4 Hz, 1H), 2.51 (s, 1H), 2.48 (s, 3H), 2.43 (d, J=10.8 Hz, 3H), 2.16 (d, J=12.8, 3.2 Hz, 1H), 2.11-2.00 (m, 1H), 1.98-1.85 (m, 1H). LC-MS: (ESI) m/z=520.6 [M+H]+

Example 14

Follow the general method for the chiral separation of racemic product 1-13 to give enantiopure product 14-41 below:

| Compound | | LC-MS: (ESI) |
|---|---|---|
| Compound 14 | (R)-1-(3,3-difluoro-1-methylpiperidin-4-yl)-8-(6-methoxypyridin-3-yl)-3-methyl-1,3-dihydro-2H-imidazo[4,5-c]quinolin-2-one (14) | m/z = 440.2 [M + H]+ |
| Compound 15 | (R)-1-(1-ethyl-3,3-difluoropiperidin-4-yl)-8-(6-methoxypyridin-3-yl)-3-methyl-1,3-dihydro-2H-imidazo[4,5-c]quinolin-2-one (15) | (LC-MS: ESI) m/z = 454.2 [M + H]+ |
| Compound 16 | (R)-1-(3,3-difluoro-1-isopropylpiperidin-4-yl)-8-(6-methoxypyridin-3-yl)-3-methyl-1,3-dihydro-2H-imidazo[4,5-c]quinolin-2-one (16) | LC-MS: (ESI) m/z = 468.2 [M + H]+ |

-continued

| | | |
|---|---|---|
| Compound 17 | (R)-1-(3,3-difluoro-1-methylpiperidin-4-yl)-8-(6-ethoxypyridin-3-yl)-3-methyl-1,3-dihydro-2H-imidazo[4,5-c]quinolin-2-one (17) | LC-MS: (ESI) m/z = 454.2 [M + H]$^+$ |
| Compound 18 | (R)-1-(3,3-difluoro-1-methylpiperidin-4-yl)-7-fluoro-8-(6-methoxypyridin-3-yl)-3-methyl-1,3-dihydro-2H-imidazo[4,5-c]quinolin-2-one (18) | LC-MS: (ESI) m/z = 457.2 [M + H]$^+$ |
| Compound 19 | (R)-1-(3,3-difluoro-1-(methyl-d3)piperidin-4-yl)-8-(6-methoxypyridin-3-yl)-3-methyl-1,3-dihydro-2H-imidazo[4,5-c]quinolin-2-one (19) | LC-MS: (ESI) m/z = 443.2 [M + H]$^+$ |
| Compound 20 | (R)-1-(3,3-difluoro-1-methylpiperidin-4-yl)-8-(6-isopropoxypyridin-3-yl)-3-methyl-1,3-dihydro-2H-imidazo[4,5-c]quinolin-2-one (20) | LC-MS: (ESI) m/z = 468.2 [M + H]$^+$ |
| Compound 21 | (R)-1-(3,3-difluoro-1-methylpiperidin-4-yl)-8-(6-(dimethylamino)pyridin-3-yl)-3-methyl-1,3-dihydro-2H-imidazo[4,5-c]quinolin-2-one (21) | LC-MS: (ESI) m/z = 453.2 [M + H]$^+$ |
| Compound 22 | (R)-1-(3,3-difluoro-1-methylpiperidin-4-yl)-8-(6-methoxypyridin-3-yl)-3-(methyl-d3)-1,3-dihydro-2H-imidazo[4,5-c]quinolin-2-one (22) | LC-MS: (ESI) m/z = 443.2 [M + H]$^+$ |
| Compound 23 | (R)-8-(6-cyclopropoxypyridin-3-yl)-1-(3,3-difluoro-1-methylpiperidin-4-yl)-3-methyl-1,3-dihydro-2H-imidazo[4,5-c]quinolin-2-one (23) | LC-MS: (ESI) m/z = 466.2 [M + H]$^+$ |
| Compound 24 | (R)-1-(3,3-difluoro-1-methylpiperidin-4-yl)-8-(6-(3-(dimethylamino)azetidin-1-yl)pyridin-3-yl)-3-methyl-1,3-dihydro-2H-imidazo[4,5-c]quinolin-2-one (24) | LC-MS: (ESI) m/z = 508.2 [M + H]$^+$ |
| Compound 25 | (R)-1-(3,3-difluoro-1-methylpiperidin-4-yl)-8-(6-(methoxy-d3)pyridin-3-yl)-3-methyl-1,3-dihydro-2H-imidazo[4,5-c]quinolin-2-one (25) | LC-MS: (ESI) m/z = 443.2 [M + H]$^+$ |
| Compound 26 | (R)-1-(3,3-difluoro-1-methylpiperidin-4-yl)-3-methyl-8-(6-((1R,5R)-(2-methyl-2,6-diazabicyclo[3.2.0]heptan-6-yl)pyridin-3-yl)-1,3-dihydro-2H-imidazo[4,5-c]quinolin-2-one (26) | LC-MS: (ESI) m/z = 520.3 [M + H]$^+$ |
| Compound 27 | (R)-1-(3,3-difluoro-1-methylpiperidin-4-yl)-3-methyl-8-(6-((1S,5S)-(2-methyl-2,6-diazabicyclo[3.2.0]heptan-6-yl)pyridin-3-yl)-1,3-dihydro-2H-imidazo[4,5-c]quinolin-2-one (27) | LC-MS: (ESI) m/z = 520.3 [M + H]$^+$ |
| Compound 28 | (S)-1-(3,3-difluoro-1-methylpiperidin-4-yl)-8-(6-methoxypyridin-3-yl)-3-methyl-1,3-dihydro-2H-imidazo[4,5-c]quinolin-2-one (28) | LC-MS: (ESI) m/z = 440.2 [M + H]$^+$ |
| Compound 29 | (S)-1-(1-ethyl-3,3-difluoropiperidin-4-yl)-8-(6-methoxypyridin-3-yl)-3-methyl-1,3-dihydro-2H-imidazo[4,5-c]quinolin-2-one (29) | LC-MS: (ESI) m/z = 454.2 [M + H]$^+$ |
| Compound 30 | (S)-1-(3,3-difluoro-1-isopropylpiperidin-4-yl)-8-(6-methoxypyridin-3-yl)-3-methyl-1,3-dihydro-2H-imidazo[4,5-c]quinolin-2-one (30) | LC-MS: (ESI) m/z = 468.2 [M + H]$^+$ |
| Compound 31 | (S)-1-(3,3-difluoro-1-methylpiperidin-4-yl)-8-(6-ethoxypyridin-3-yl)-3-methyl-1,3-dihydro-2H-imidazo[4,5-c]quinolin-2-one (31) | LC-MS: (ESI) m/z = 454.2 [M + H]$^+$ |
| Compound 32 | (S)-1-(3,3-difluoro-1-methylpiperidin-4-yl)-7-fluoro-8-(6-methoxypyridin-3-yl)-3-methyl-1,3-dihydro-2H-imidazo[4,5-c]quinolin-2-one (32) | LC-MS: (ESI) m/z = 457.2 [M + H]$^+$ |
| Compound 33 | (S)-1-(3,3-difluoro-1-(methyl-d3)piperidin-4-yl)-8-(6-methoxypyridin-3-yl)-3-methyl-1,3-dihydro-2H-imidazo[4,5-c]quinolin-2-one (33) | LC-MS: (ESI) m/z = 443.2 [M + H]$^+$ |
| Compound 34 | (S)-1-(3,3-difluoro-1-methylpiperidin-4-yl)-8-(6-isopropoxypyridin-3-yl)-3-methyl-1,3-dihydro-2H-imidazo[4,5-c]quinolin-2-one (34) | LC-MS: (ESI) m/z = 468.2 [M + H]$^+$ |
| Compound 35 | (S)-1-(3,3-difluoro-1-methylpiperidin-4-yl)-8-(6-(dimethylamino)pyridin-3-yl)-3-methyl-1,3-dihydro-2H-imidazo[4,5-c]quinolin-2-one (35) | LC-MS: (ESI) m/z = 453.2 [M + H]$^+$ |

-continued

| Compound 36 | (S)-1-(3,3-difluoro-1-methylpiperidin-4-yl)-8-(6-methoxypyridin-3-yl)-3-(methyl-d3)-1,3-dihydro-2H-imidazo[4,5-c]quinolin-2-one (36) | LC-MS: (ESI) m/z = 443.2 [M + H]$^+$ |
|---|---|---|
| Compound 37 | (S)-8-(6-cyclopropoxypyridin-3-yl)-1-(3,3-difluoro-1-methylpiperidin-4-yl)-3-methyl-1,3-dihydro-2H-imidazo[4,5-c]quinolin-2-one (37) | LC-MS: (ESI) m/z = 466.2 [M + H]$^+$ |
| Compound 38 | (S)-1-(3,3-difluoro-1-methylpiperidin-4-yl)-8-(6-(3-(dimethylamino)azetidin-1-yl)pyridin-3-yl)-3-methyl-1,3-dihydro-2H-imidazo[4,5-c]quinolin-2-one (38) | LC-MS: (ESI) m/z = 508.2 [M + H]$^+$ |
| Compound 39 | (S)-1-(3,3-difluoro-1-methylpiperidin-4-yl)-8-(6-(methoxy-d3)pyridin-3-yl)-3-methyl-1,3-dihydro-2H-imidazo[4,5-c]quinolin-2-one (39) | LC-MS: (ESI) m/z = 443.2 [M + H]$^+$ |
| Compound 40 | (S)-1-(3,3-difluoro-1-methylpiperidin-4-yl)-3-methyl-8-(6-((1R,5R)-(2-methyl-2,6-diazabicyclo[3.2.0]heptan-6-yl)pyridin-3-yl)-1,3-dihydro-2H-imidazo[4,5-c]quinolin-2-one (40) | LC-MS: (ESI) m/z = 520.3 [M + H]$^+$ |
| Compound 41 | (S)-1-(3,3-difluoro-1-methylpiperidin-4-yl)-3-methyl-8-(6-((1S,5S)-(2-methyl-2,6-diazabicyclo[3.2.0]heptan-6-yl)pyridin-3-yl)-1,3-dihydro-2H-imidazo[4,5-c]quinolin-2-one (41) | LC-MS: (ESI) m/z = 520.3 [M + H]$^+$ |

Example 12. Biological Data

Phosphorylation of ATM protein using MCF-7 cell was detected using ODYSSEY CLx (LI-COR); about 25 uL cells were seeded in each blank 384-well plate, 24 hours later, add the proportionally diluted compound and Etoposide using pin tool and incubated at 37° C. for 1 h and then cells were fixed by adding 25 ul of 8% paraformaldehyde for 20 minutes at room temperature. Cells were Permeabilized with 1×PBS containing 0.1% Triton X-100, blocked by adding 50 μl of Odyssey Blocking Buffer and shaked for 1.5 hours at room temperature. The blocking buffer was removed, 20 μl of anti-pKAP1 antibody was added and anti-pKAP1 antibodies were Incubated overnight at 4 degrees on gentle shaker. 20 μl of secondary antibody (IRDye 800CW Goat anti-Rabbit IgG) solution was added containing DNA stain DRAQ5 (1/4,000) to each plate well, diluted in blocking buffer with 0.1% Tween-20 (1/5000) and incubated secondary antibodies for 1 hour. Solution was washed and removed. Scan plate immediately using ODYSSEY CLx (LI-COR) for the inhibition of phosphorylation of ATM protein.

In the cell-based inhibition of phosphorylation of ATM, Compounds of the present invention are effective in inhibiting pATM signaling on MCF-7, and thus have the potential ability to overcome the resistance of radiotherapy or chemo by DNA damage reparation of ATM protein.

TABLE 1

| MCF-7 cell pATM inhibition (IC50 unit is nM) | | |
|---|---|---|
| | Compound 1-41 | Compound X |
| IC50 | <100 | <1 |

Blood-Brain Barrier Penetration

To determine whether the compound was able to cross the blood-brain barrier (BBB), the rats or mice were administered with the test compound. Four hours after dosing, rats or mice were sacrificed, blood and brain tissue were collected and the concentration of the test compound was analyzed. Brain permeation is defined as the ratio of the concentration of the compound in the brain tissue to the concentration in the plasma. P-glycoprotein and BCRP (Breast Cancer Resistance Protein) are the blood-brain barrier efflux proteins, the P-glycoprotein substrate (Efflux ratio>1.5) and/or BCRP substrate (Efflux ratio>1.5) is out of the brain.

TABLE 2

| Blood-brain barrier penetration | | |
|---|---|---|
| Compound | Compound 1-41 | Compound X |
| Blood-brain barrier penetration | >0.3 | 0.75 |
| P-glycoprotein efflux substrate | No Efflux ratio <1 | No Efflux ratio <1 |
| BCRP efflux substrate | No Efflux ratio <1 | No Efflux ratio <1 |

In the brain penetration assay, the ratio of the compound concentration of the compound of the present invention (compound 1-41) in the brain tissue to the concentration in plasma is more than 30% and is not a P-glycoprotein substrate and BCRP substrate, have crossed the blood-brain barrier, so they have the potential to achieve effective plasma concentrations in the brain for the treatment and/or prevention of cancer brain metastases, meningeal metastases, glioma, glioblastoma, DIPG and other central nervous system diseases.

Aldehyde Oxidase Susceptibility:

Human aldehyde oxidase (hAOX), a cytosolic drug-metabolizing enzyme expressed in human liver that, similarly to CYPs, contributes to significant amount of quinoline derivatives' oxidation, but acting in the absence of NADPH cofactor. Drugs that are substrates for AOX often exhibit high metabolic clearance, resulting in low exposure and hence in decreased drug efficacy in humans (Lepri et al. PNAS, 2017, pp. E3178-E3187). Compounds of the present invention (compound 1-41) are not substrate of human aldehyde oxidase with long half-life, so they have the potential to achieve effective drug efficacy in the brain with low metabolic clearance for the treatment and/or prevention of cancer brain metastases, meningeal metastases, glioma, glioblastoma, DIPG and other central nervous system diseases.

TABLE 3

Aldehyde oxidase susceptibility

| Compound | Compound 1-41 | Compound X |
|---|---|---|
| Aldehyde oxidase substrate | No | No $T_{1/2} > 20$ h |

While the present invention describes a number of embodiments, our underlying embodiments may be modified to provide other embodiments that utilize the compounds and methods of the present invention. Accordingly, the scope of the invention is defined by the appended claims rather than by the specific embodiments shown by way of example.

All references cited in this application (including, but not limited to, abstracts, articles, journals, publications, textbooks, papers, technical data sheets, Internet sites, databases, patents, patent applications, and patent publications) are expressly incorporated herein by reference in their entirety. Unless otherwise defined, all technical and scientific terms used herein have the same meaning as commonly understood by one of ordinary skill in the art.

What is claimed:

1. A compound comprising a structure of formula (I), said compound being

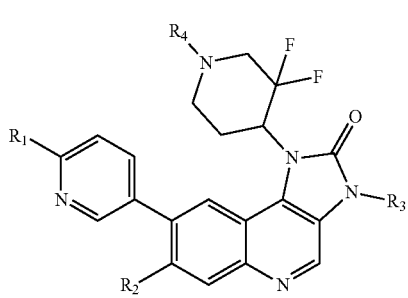

(I)

wherein R1 is independently selected from OC1-3 alkyl, OC3-5 cycloalkyl, OC1-C3 deuterated alkyl, dialkyl amine, substituted C4-C6 cycloamine or diazabicyclo amine;
R2 is independently selected from hydrogen or fluoro;
R3 is independently selected from methyl or deuterated methyl;
R4 is independently selected from C1-C3 alkyl or C1-C3 deuterated alkyl.

2. The compound according to claim 1, characterized in that,
R1 is independently selected from methoxy, ethoxy, isopropoxy, cyclopropoxy, deuterated methoxy, dimethyl amine, N,N-dimethylazetidine-3-amine or 2-methyl-2, 6-diazabicyclo[3.2.0]heptane;
R2 is independently selected from hydrogen or fluoro;
R3 is independently selected from methyl or deuterated methyl;
R4 is independently selected from methyl, ethyl, isopropyl or deuterated methyl.

3. A pharmaceutical composition comprising a compound according to claim 1, a salt thereof, a solvate thereof, a hydrate thereof or a polycrystal thereof type, and pharmaceutically acceptable excipients or adjunct ingredients.

4. The compound according to claim 1 for use as an ATM inhibitor.

5. The compound according to claim 1 or a pharmaceutically acceptable salt thereof for use in a method for treating cancer, wherein a therapeutically effective amount of the compound of Formula (I), or the pharmaceutically acceptable salt thereof is administrated simultaneously, separately or sequentially with other treatment.

6. A pharmaceutical composition for treating or preventing ATM protein activation mediated by ATM, wherein the compound according to claim 1 is employed in the manufacture of the pharmaceutical composition.

7. The pharmaceutical composition according to claim 6, wherein the ATM protein is an Ataxia-telangiectasia mutated kinase.

8. The pharmaceutical composition according to claim 6, wherein the pharmaceutical composition is used for treatment of a proliferative disease, or a cancer, and wherein the compound of Formula (I) is administered simultaneously, separately or sequentially with radiotherapy.

9. The pharmaceutical composition according to claim 8, wherein the pharmaceutical composition is used for treatment of cancer, and wherein the compound of Formula (I) is administered simultaneously, separately or sequentially with at least one additional anti-tumor substance selected from the group consisting of cisplatin, oxaliplatin, carboplatin, valrubicin, idarubicin, doxorubicin, pirarubicin, irinotecan, topotecan, amrubicin, epirubicin, etoposide, mitomycin, bendamustine, chlorambucil, cyclophosphamide, ifosfamide, carmustine, melphalan, bleomycin, olaparib, rucaparib, niraparib, talazoparib, pamiparib, pembrolizumab, nivolumab, cemiplimab, spartalizumab, sintilimab, tislelizumab, dostarlimab, atezolizumab, avelumab, durvalumab, AZD1775, VX-970, BAY1895344 and AZD6738.

10. The pharmaceutical composition according to claim 8, wherein the proliferative disease is glioblastoma, diffuse intrinsic pontine glioma, astrocytoma, oligodendroglioma, ependymoma, meningioma, pituitary adenoma, vestibular schwannoma and medulloblastoma.

* * * * *